(12) United States Patent
Delaveau et al.

(10) Patent No.: US 8,822,528 B2
(45) Date of Patent: Sep. 2, 2014

(54) MONENSIN DERIVATIVES FOR THE TREATMENT AND PREVENTION OF PROTOZOAL INFECTIONS

(75) Inventors: Jean Delaveau, Saint Nicolas de Macherin (FR); Emile Vialle, Beauregard l'Eveque (FR); Marc Lemaire, Villeurbanne (FR); Stephane Pellet-Rostaing, Villeurbanne (FR); Bruno Andrioletti, Miribel (FR)

(73) Assignees: Merial Limited, Duluth, GA (US); Universite Claude Bernard Lyon 1, Paris (FR); Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 13/297,367

(22) Filed: Nov. 16, 2011

(65) Prior Publication Data

US 2012/0128722 A1    May 24, 2012

Related U.S. Application Data

(60) Provisional application No. 61/414,234, filed on Nov. 16, 2010.

(51) Int. Cl.
  *A61K 31/35*    (2006.01)
  *A61K 31/366*   (2006.01)
  *A61K 31/365*   (2006.01)
  *C07D 493/22*   (2006.01)
  *C07D 493/10*   (2006.01)

(52) U.S. Cl.
  USPC ............ 514/450; 514/456; 549/343; 549/264; 549/265

(58) Field of Classification Search
  USPC ........ 424/269.1; 549/343, 264, 265; 514/456, 514/450
  See application file for complete search history.

(56) References Cited

U.S. PATENT DOCUMENTS

| 3,832,358 A | 8/1974 | Chamberlin |
| 5,725,894 A | 3/1998 | Toyomizu et al. |

FOREIGN PATENT DOCUMENTS

| EP | 2 070 522 | 6/2009 |
| FR | 2 605 221 | 4/1988 |

OTHER PUBLICATIONS

Cox et al. *J. Am. Chem*, Soc. 1984, 106,5965-5969.
Sakakibara et al. *Chem. Pharm. Bull*. 1988, 36, 4776-4784.
Gaboyard et al. *Agric. Chem*. 1990,54, 1149-1155.
Nagatsu et al. *Chem. Pharm. Bull*. 1997, 45, 966-970.
Rochdi et al. *J. Med. Chem*. 1996, 39,588-595.
Tsukube et al. *J. Org. Chem*.1991, 56,875-878.
Suzuki et al. *J. Chem. Soc. Chem*. Commun.1987, 932-934.
Tohoa et al. *Analytical Chemistry* 1990, 62, 936-942.
Murayama et al. *Tetrahedron*1992, 42,805-818.
Oosio et al. *Biochemical Pharmacology*1996, 52, 157-166.
Huczynski et al. *Journal of Molecular Structure* 2006, 797, 99-11 0.
Huczynski et al. *Journal of Molecular Structure* 2007, 829, 111-11 9.
Huczynski et al. *Bioorg. Med. Chem. Lett*. 2008, 18, 2585-2589.
Huczynski et al. *Journal of Molecular Structure* 2008, 874, 89-1 00.
Lowicki et al. *Journal of Molecular Structure* 2009, 923, 53-59.
Nagatsu et al. *Chem. Pharm. Bull*. 1994,42,2269-2275.
Gumila 1996 Differential in vitro activities of ionophores against *falciparum*. Antimicrobial Agents and Chemotherapy, Mar. 1996, p. 602-608.
Cane 1982—Polyether biosynthesis. J. Am. Chem. Soc. 1982, 104, 7274-7281.
Kappe et al. Science May 14, 2010. That Was Then but This is Now: Malaria Research in the Time of an Eradication Agenda.
Mackinnon et al.Science May 14, 2010. The Selection Landscape of Malaria Parasites.
Enserink. Science May 14, 2010. If Artemisinin Drugs Fail, What's Plan B?.

*Primary Examiner* — Kristin Vajda
(74) *Attorney, Agent, or Firm* — Judy Jarecki-Black; Chad Kitchen; Merial Limited

(57) ABSTRACT

This invention relates to novel polyether ionophores, formulations comprising same, and to methods of making and using these compounds and formulations for the treatment and/or prevention of parasitic infection in animals and humans. These compounds exhibit improved safety profiles and/or efficacies as compared to parent compounds.

13 Claims, 28 Drawing Sheets

Monensin A

Monensin A – complexed around sodium ion

| Chemical shift δ (ppm) | Carbon |
|---|---|
| 8.56 | C(31) |
| 10.84 | C(33) |
| 11.39 | C(34) |
| 14.91 | C(29) |
| 16.40 | C(27) |
| 17.04 | C(36) |
| 17.15 | C(28) |
| 27.60 | C(14) |
| 27.78 | C(32) |
| 30.16 | C(15) |
| 30.99 | C(30) |
| 32.18 | C(22) |
| 33.53 | C(11) |
| 33.59 | C(19) |
| 33.87 | C(8) |
| 34.66 | C(18) |
| 35.18 | C(6) |
| 35.97 | C(23) |

| Chemical shift δ (ppm) | Carbon |
|---|---|
| 36.86 | C(24) |
| 37.80 | C(4) |
| 39.57 | C(10) |
| 45.35 | C(2) |
| 58.26 | C(35) |
| 65.20 | C(26) |
| 68.68 | C(5) |
| 70.78 | C(7) |
| 74.81 | C(21) |
| 76.75 | C(20) |
| 82.86 | C(13) |
| 83.33 | C(3) |
| 85.32 | C(17) |
| 85.54 | C(12) |
| 86.16 | C(16) |
| 98.62 | C(25) |
| 107.30 | C(9) |
| 181.58 | C(1) |

FIG. 2B

| N° Réaction | Amide | R' | R'' | Rendement isolé | LogP* |
|---|---|---|---|---|---|
| EV 01082 | 6a | ethyl-C6H4-COOH | - | 57% | 5,62 |
| EV 01113 | 6b | R''—CH—COOH | indole (3-yl) | 92% | 6,03 |
| EV 02028 | 6c | R''—CH—COOH | 4-F-C6H4 | 14% | 5,79 |
| EV 02062 | 6d | R''—CH—COOH | —S—C(Ph)3 | 0% Obtention of [M-CH2] | 9,56 |

| Reaction No. | Conditions | Rxn. Time | % Isolated | Purification |
|---|---|---|---|---|
| EV 01073 | 2,2'-dipyridinyl disulfide, PPh$_3$ | 67h | 64% | 2 Columns |
| EV 02032 | DCC, DMAP, DMAP·HCL | 15h | 80% | Extraction |

Schizont (maturation)

Mature schizont =
release of merozoites

| Reaction No. | Name | Molecule | IC$_{50}$ |
|---|---|---|---|
| EV 01066 | Monensine acide 1a | | 25.0 µg/ml |
| EV 01051 | Amide 3a | | 11.9 µg/ml |
| EV 01069 | Amide 3b | | 18.5 µg/ml |
| EV 01082 | Amide 6a | | 38.9 µg/ml |
| EV 03031 | Amide 3c | | > 50 µg/ml |
| EV 02066 | Amide 4c | | > 50 µg/ml |
| EV 01060 | Lactone 7 | | 9.0 µg/ml |
| EV 02121 | Lactone 14a | | > 50 µg/ml |
| EV 02058 | Monensine éthérifiée 8a | | > 50 µg/ml |
| EV 02127 | Monensine oxydée 19 | | > 50 µg/ml |

| Reaction No. | Name | Molecule |
|---|---|---|
| EV 02079 | Oxidised lactone 18 |  |
| EV 02171 | Oxodioxane monensin 12 |  |
| EV 03105 | Saponified oxodioxane monensin 27 |  |
| EV 03109 | Saponified oxidised monensin 31 |  |
| EV 03130 | Oxidised oxodioxane monensin 26 |  |

MONENSIN DERIVATIVES FOR THE TREATMENT AND PREVENTION OF PROTOZOAL INFECTIONS

INCORPORATION BY REFERENCE

This application claims priority to U.S. provisional patent application No. 61/414,234, filed Nov. 16, 2010, the disclosure of which is herein incorporated by reference in its entirety.

FIELD OF THE INVENTION

The present invention relates to novel monensin derivatives, a method for making such compounds, and a method of preventing, treating, or otherwise controlling protozoans or bacteria, including for example coccidia, plasmodium, and mycoplasma in animals. The present invention has particular, though not sole, application to controlling coccidia in animals or animal surroundings and controlling malaria in humans.

BACKGROUND

Coccidiosis caused by obligate intracellular protozoan parasite of the genus *Eimeria* is a major constraint for modern poultry production. It is considered as one of the most expensive and common diseases of poultry and costs the world's commercial chicken producers at least US$ 1.5 billion annually. Among various *Eimeria* species, *Eimeria tenella*, which causes caecal coccidiosis, is highly pathogenic. To date, control of coccidiosis is largely limited to good husbandry and prophylactic chemotherapy using a range of drugs against which resistance is rapidly acquired. Few if any new drugs are in the pipeline to fill this unmet need.

A similar problem is evolving around a human protozoal parasite, *plasmodium falciparum*, which is the causative agent of malaria. The current generation of anti-malarial therapy includes primarily artemisinin-based combination therapies (ACTs) (Enserink, SCIENCE 2010). Current ACTs that are reasonably far along in the development pipeline are merely variations on the artemisinin theme. Their efficacy in killing parasites is untested. The three artemisinin derivatives currently used in ACTs are so closely related chemically that parasites resistant to one will probably be resistant to all. One drug, called artemisone, has been through a phase II trial for nonresistant malaria but failed to offer major benefits over existing derivatives.

One compound that has been used in combating coccidia is Monensin. This compound is an antibiotic of the spiroacetal family of polyether ionophores, obtained by fermentation of *streptomyces cinnamonensin* and *albus* (FIG. 1A-D). Monensin contains seventeen stereogenic centres, a spiroacetal, three tetrahydrofuran rings and two tetrahydropyran rings. For additional background see Cox F. E. G., Int. J. Parasitol., 1998, 28, 165-179; Yadav A. et al. Vet. Parasitol., 2001, 102, 69-75; and Agtarap A. et al. J. Chem. Am. Soc., 1967, 89 (22), 5737-5739. As most polyether receptors of the same family forming pseudo-macrocyclic complexes with the mono- and divalent cations, this compound acts as an ion exchanger, creating a ionic unbalance between the cell and its surrounding environment, unbalance which is at the origin of cell apoptosis. These remarkable pharmacological properties make it a first-rate pharmaceutical or veterinary antiparasitic, particularly active against Coccidia, plasmodia, Gram-positive organisms, and mycoplasmas.

Monensin has been used, for example, to improve milk and meat production in the cattle industry (e.g. RUMENSIN®, Elanco Products). However, toxicity of Monensin in some mammals, like equines (T. Matsuoka et al., "Review of monensin toxicosis in horses", J. Equine Veterinary Science, 16, 1996, 8-15) has been observed, indicating Monensin derivatives having improved safety profiles could be useful—In addition, monensin and derivatives thereof could be useful against babesiosis, which is a disease caused by a protozoan parasite carried by a tick. Recently, the US Agricultural Research Service (ARS) began working on new ways of protecting cattle in Texas from babesiosis. Babesiosis caused considerable harm to the US cattle industry until the early 20th century, when the parasites were largely eradicated within the United States. The ticks continue to thrive across the border in Mexico, however, and are now found in increasing numbers in southern Texas, due in part to growing populations of wild hoofed animals, such as deer, along the border. ARS researchers in Kerrville, Tex., are testing several ways of eliminating the ticks and mitigating the impact of babesiosis on the local livestock industry. The researchers have also developed a slow-release injectable formulation of the antiparasitic doramectin. Currently, producers with infested pastures have to round up and dip their cattle every two weeks for nine months to clear the infestation, so new treatment options promise to save them considerable effort and expense. Improved monensin derivatives would could be useful in combatting babesiosis, and would almost certainly be more cost-effective and easier to administer, as compared to the slow-release doramectin formulation. Monensin exerts its effect during the development of first-generation trophozoites into first-generation schizonts within the intestinal epithelial cells. It does not interfere with hosts' development of acquired immunity to the majority of coccidial species. However, the emergence of resistance phenomena has become a major problem and up to now, little or no consideration in terms of the structural modification of the given ionophores was assigned to restore their activity. To date, a few modified analogues of monensin have been synthesized primarily for structure-activity relation (SAR) studies, though little if any efficacy data has been generated.

Recently, EP02070522A1 (Mazier et al.) disclosed monensin derivatives modified at several positions, some of which showed efficacy in mice against *P. yoelii*. However, only several of the recited possible compounds appear to have been synthesized and/or tested. Further, applicants indicate the medicaments preferably further comprise at least one compound having anti-malarial activity, possibly contra-indicating use of the disclosed monensin derivatives as stand-alone anti-malarial agents. No anti-coccidal activity was contemplated.

Other references disclosing synthesis of monensin derivatives include:

| Reference Name | Reference ID | Monensin Modification(s)/Site(s) | Organism(s) |
| --- | --- | --- | --- |
| Rochdi et al. | J. Med. Chem. 1996, 39, 588-595 | C25-C26 | *P. falciparum* |
| Jeminet | FR2605221 | De(hydroxymethyl)-25 deoxy-25 oxo-25 monensin | *Eimeria* |
| Gumila et al. | Antimicrobial Agents and Chemotherapy, Mar. 1996, p. 602-608 Vol. 40, No. 3 | Methyl ester, lactone | *P. falciparum* |

-continued

| Reference Name | Reference ID | Monensin Modification(s)/Site(s) | Organism(s) |
|---|---|---|---|
| Gaboyard et al. | Agric. Biol. Chem., 54 (5), 1149-1155, 1990 | C25-C26 | *B. cereus* |

The emergence of organisms resistant to classical anti-coccidiosis agents ("coccistats") and anti-malarial agents, coupled with the scarcity of novel replacement drugs, urges the development of novel active compounds. Rotation of drugs has not proven completely effective in overcoming the resistance problem, and almost no new anticoccidians are being developed for the avian market. There are clearly long-felt and unmet needs for new coccistats having improved resistance profiles.

It is expressly noted that citation or identification of any document in this application is not an admission that such document is available as prior art to the present invention. Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

SUMMARY OF THE INVENTION

A first aspect of the invention is to provide novel compounds that are based upon the polyether ionophore Monensin and are active against protozoal parasites of animals including humans. In some embodiments, the compounds are active against bacteria, for example, but not solely, mycoplasmas and gram-positive organisms.

The invention is also directed toward a method of treating an animal (e.g. a mammal or bird) against parasitic infection by administering a parasiticidally effective amount of the compositions of the invention. Animals which can be treated include but are not limited to chickens/avians, humans, cats, dogs, cattle, cows, deer, goats, horses, llamas, pigs, sheep and yaks. In one embodiment of the invention, the animals treated are chickens/avians, humans, sheep, or goats.

In one embodiment, the present invention provides polyether ionophore compounds of formula (I) shown below:

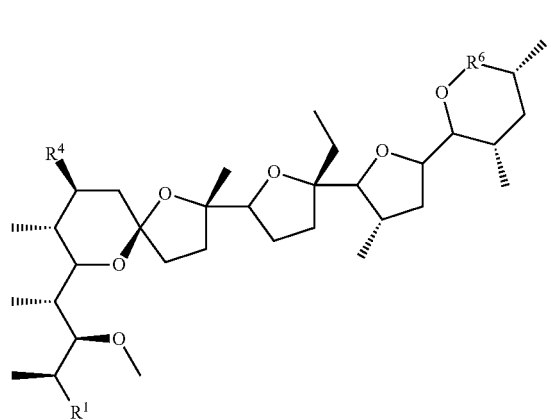

(I)

or a veterinarily or pharmaceutically acceptable salt thereof.

In another embodiment, the present invention provides macrocyclic polyether ionophore compounds of formula (II) shown below:

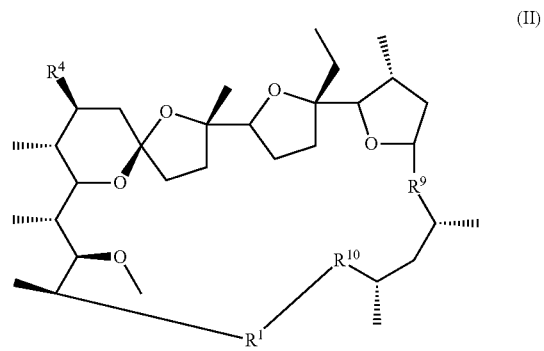

(II)

wherein $R^1$ includes $C(=O)OR^2$ or $C(=O)NR^3$; $R^4$ includes $OR^S$; and $R^6$ includes $C(R^7)R^8$; and wherein additional meanings of variables $R^1$, $R^2$, $R^3$, $R^4$, $R_5$, $R^6$, $R^7$, $R^8$, $R^9$, and $R^{10}$ are as described below. The invention also provides veterinary and pharmaceutical compositions comprising the inventive compounds, or salts thereof, in combination with a veterinarily or pharmaceutically acceptable carrier or diluent.

The inventive compounds and compositions comprising the compounds are highly effective for the treatment or prophylaxis of parasites in or on mammals, fish and birds, and in particular, cats, dogs, horses, chickens, pigs, sheep and cattle with the aim of ridding these hosts of all the parasites commonly encountered by mammals, fish and birds. The invention also provides for effective and long-lasting defense against protists, such as coccidia and plasmodia, and against bacteria, such as mycoplasma in animals and humans.

Accordingly, the present invention provides methods for preventing and treating parasites in or on animals, comprising administering a parasiticidally effective amount of a compound of formula (I) or (II), or a veterinarily acceptable salt thereof, to the animal.

It is an object of the invention to not encompass within the invention any previously known product, process of making the product, or method of using the product such that the Applicants reserve the right to this invention and hereby disclose a disclaimer of any previously known product, process, or method.

It is noted that in this disclosure and particularly in the claims, terms such as "comprises", "comprised", "comprising" and the like can have the meaning attributed to such terms in U.S. patent law; e.g., they can mean "includes", "included", "including", and the like; and that terms such as "consisting essentially of" and "consists essentially of" have the meaning ascribed to them by U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF DRAWINGS

A full and enabling disclosure of the present invention, including the best mode thereof, to one of ordinary skill in the art, is set forth more particularly in the remainder of the specification, including reference to the accompanying figures, wherein:

FIG. 2B provides tabular NMR data;

FIG. 28 summarizes IC$_{50}$ values, as measured by toxicity assay, for the indicated compounds;

DETAILED DESCRIPTION OF THE INVENTION

Figure 1A:
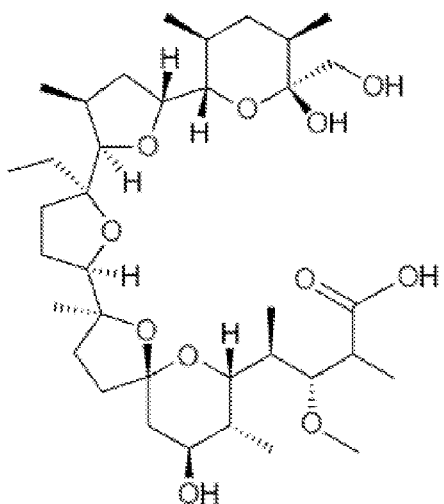
FIG. 1A provides the structure of Monensin A.
Figure 1B:
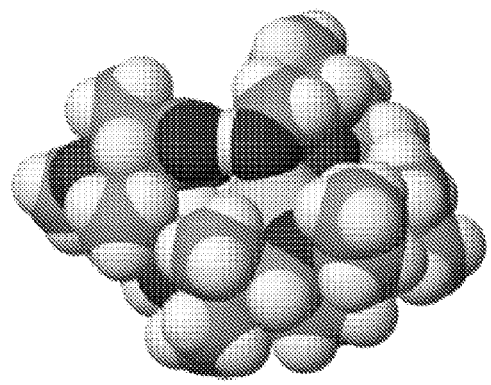
FIG. 1B provides a space-filled model with Monensin A surrounding a sodium ion.
Figure 1C:
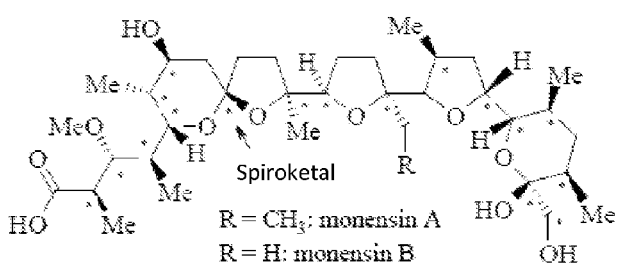
FIG. 1C illustrates spiroacetal centers of Monensin A/B.
Figure 1D:
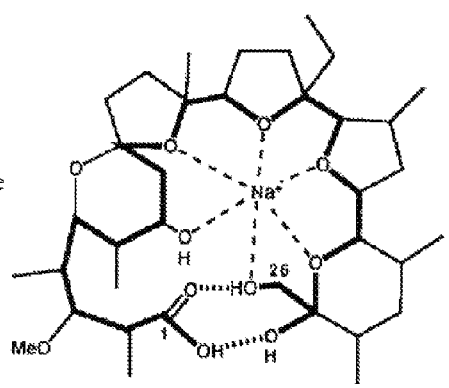
FIG. 1D provides monensin XR structure.
Figure 2A:
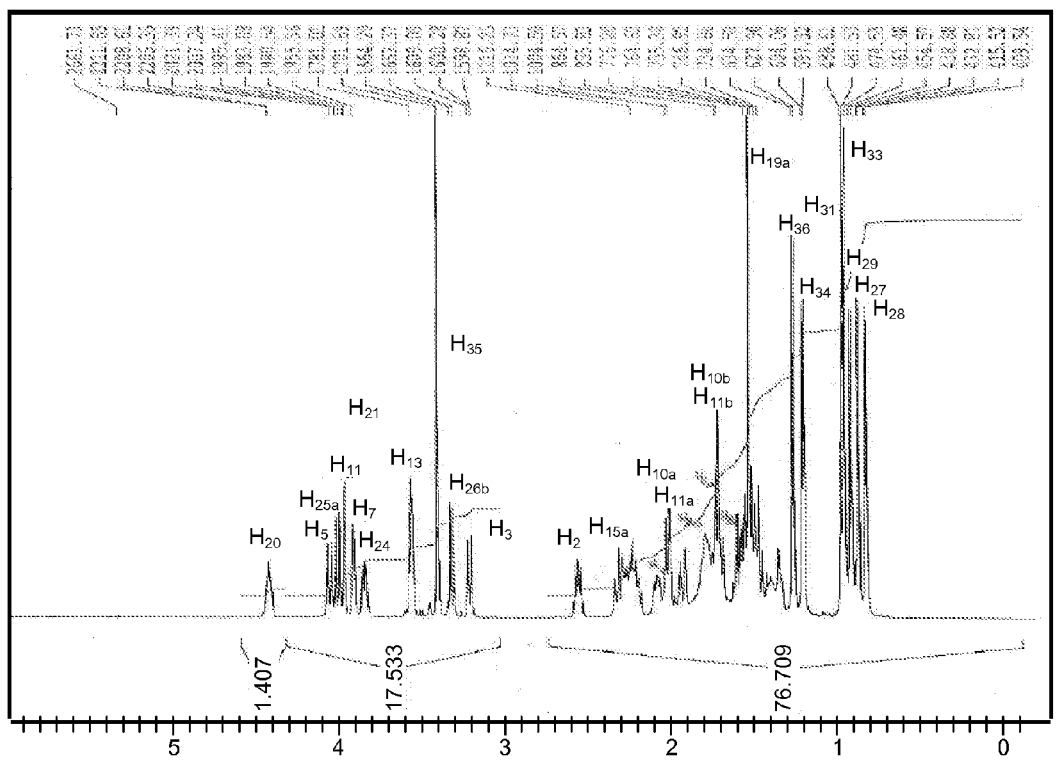
FIG. 2A provides NMR data.
Figure 2A:
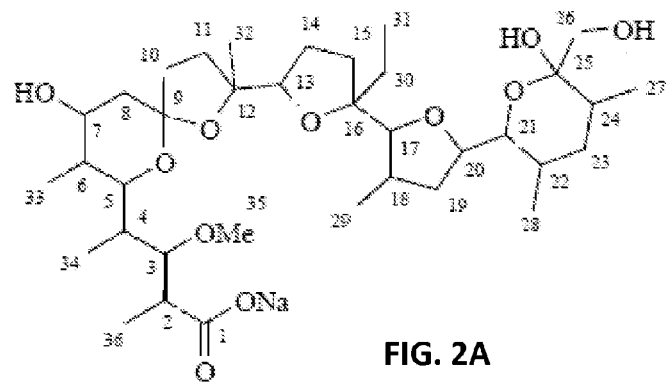
Figure 3:
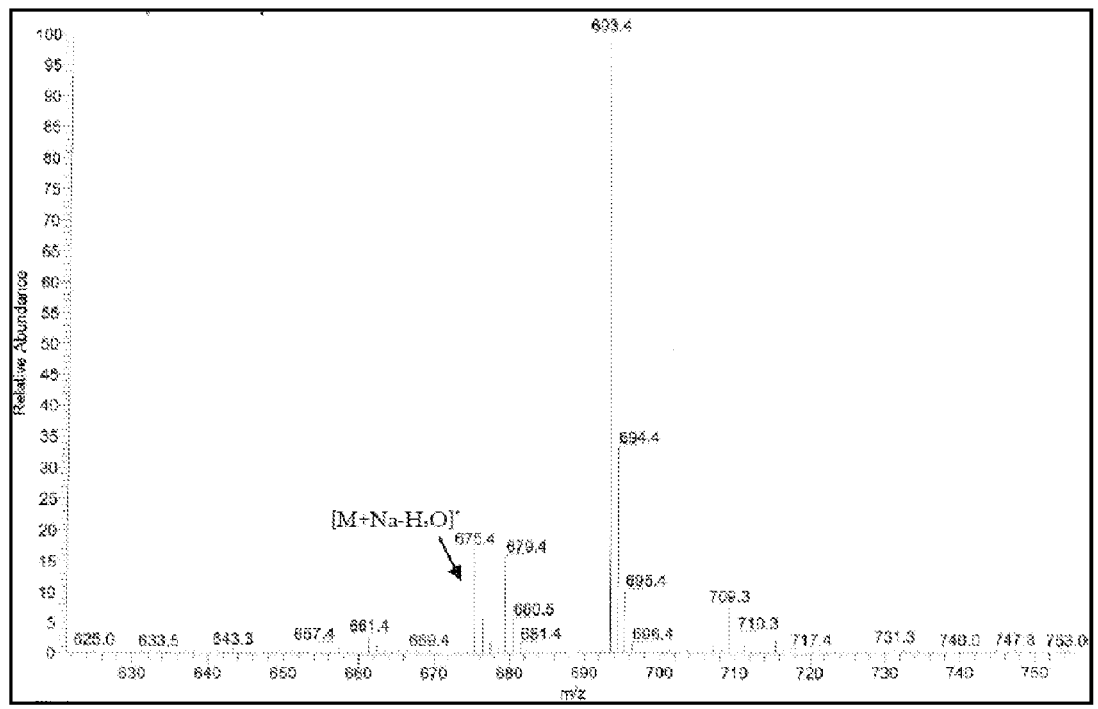
FIG. 3 provides monensin mass spectrum showing predominant presence of sodium adducts and the absence of protonated molecular ions. The monensin sodium salt has a mass of 693.4. Therefore, monensin entraps sodium in the mass chamber, showing thus the sodium adduct.
Figure 4:
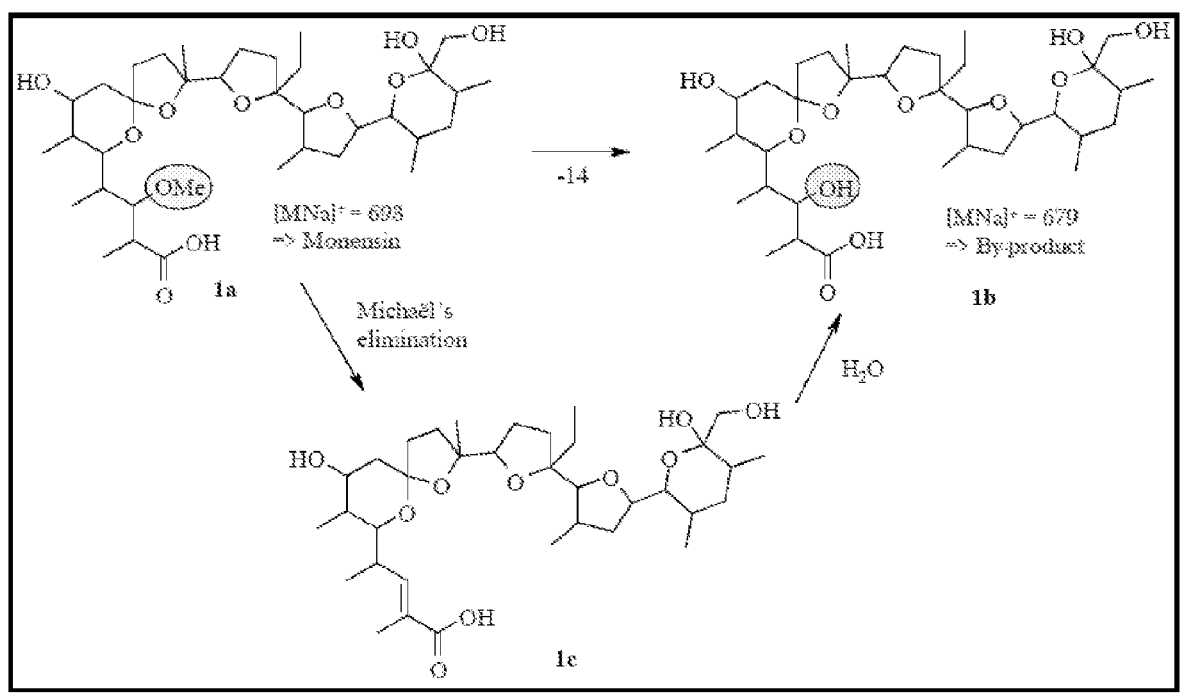
FIG. 4 provides mechanism whereby monensin impurity/by-product is formed. The first species has a mass of 679 and the second species of 693. The 693 mass corresponds to the sodium-coupled monensin. The 679 mass corresponds to monensin. The (1b) structure can result from (1c), beginning with Michael's elimination of the methoxy group, followed by the hydration of the intermediate acrylic residuum.
Figure 5:
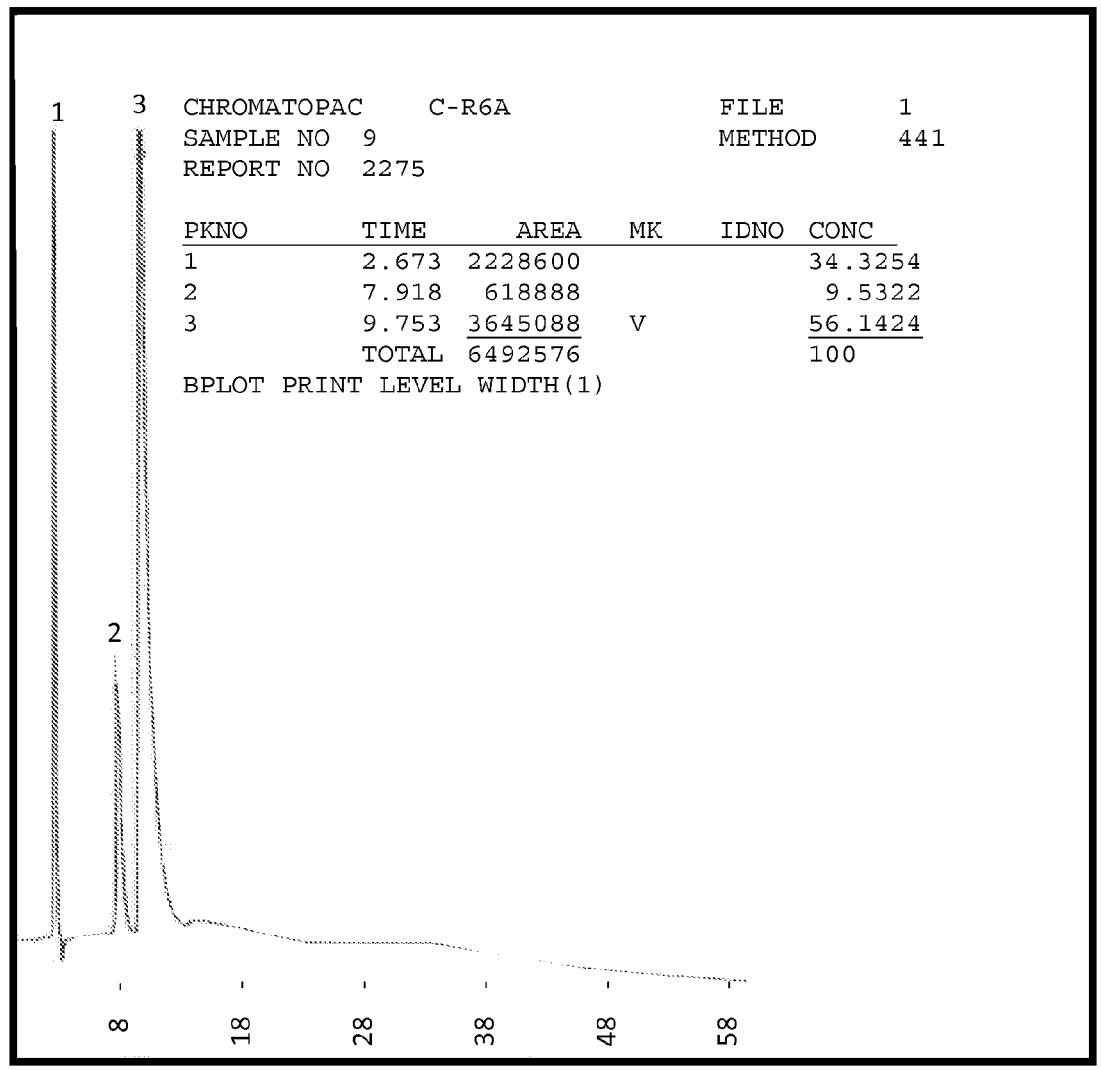
FIG. 5 provides monensin HPLC results. The 9.75 min. signal is the product present at 85%, whereas the 7.75 min. signal represents 15% of the mixture. This minority signal was an impurity of the marketed monensin sodium salt.
Figure 6A:
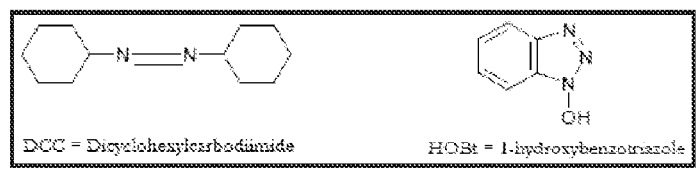
FIG. 6A schematizes the amidation reactions.
Figure 6A:
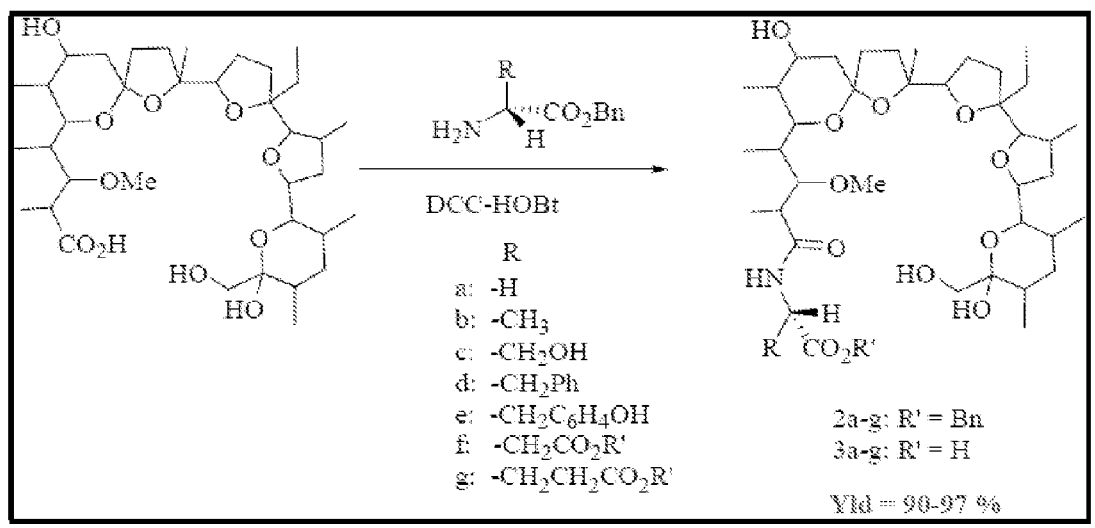
Figure 6B:
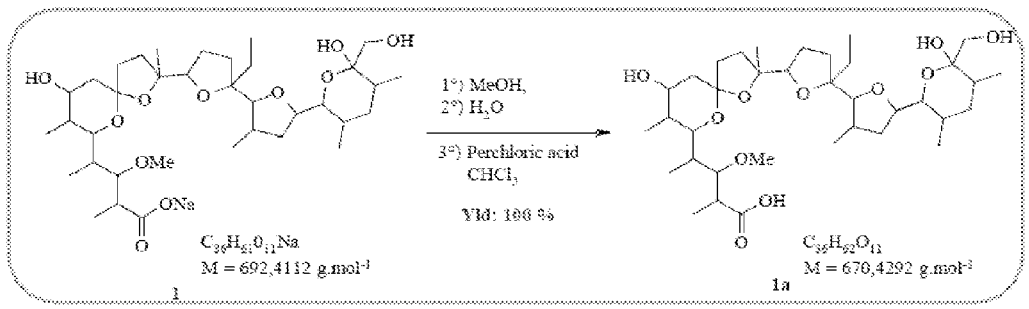
FIG. 6B illustrates synthesis of monensin acid (1a) from monensin (1)
Figure 6C:
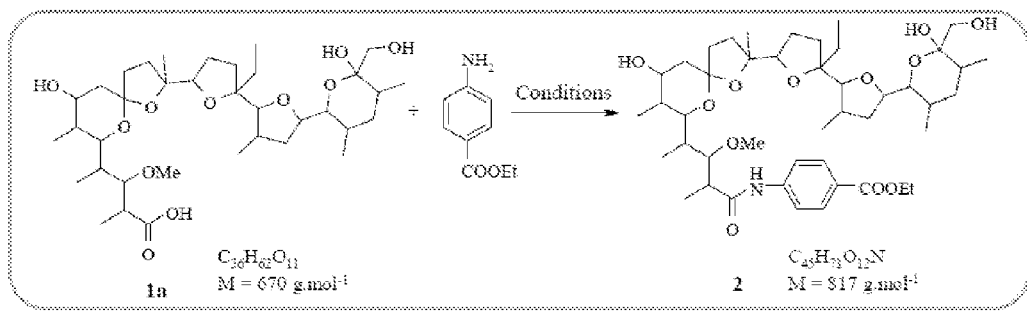
FIG. 6C illustrates amidation of monensin acid (1a) with ethyl-4-aminobenzoate to yield (2)
Figure 6D:
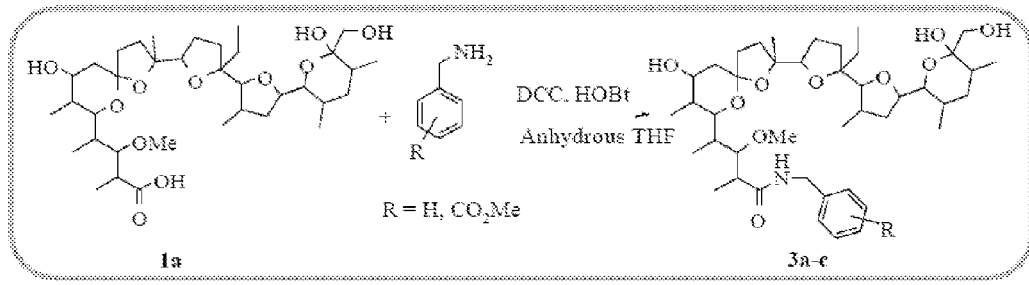
FIG. 6D illustrates amidation of monensin acid (1a) with benzylamine and its derivatives to yield (3a-c)
Figure 7:
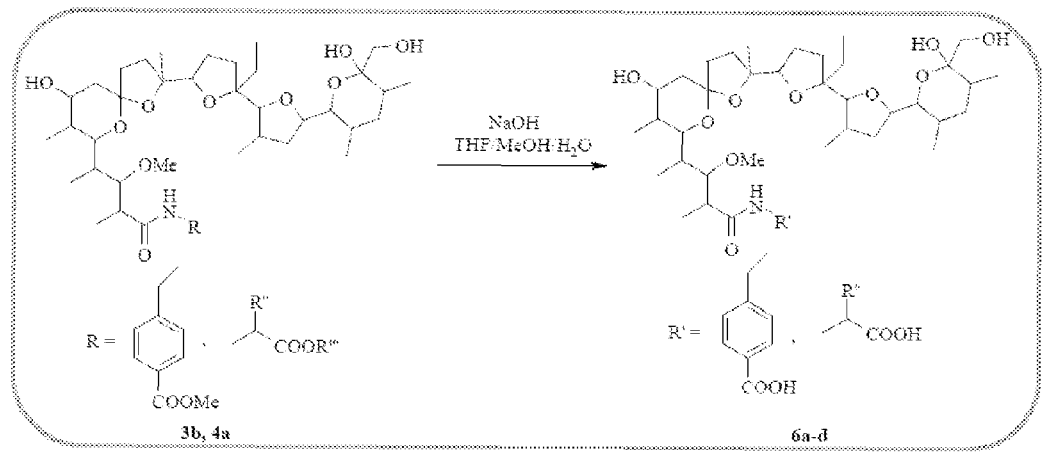
FIG. 7 provides the saponification reaction whereby structures (3b, 4a) were converted into structures (6a-d)
Figure 8:
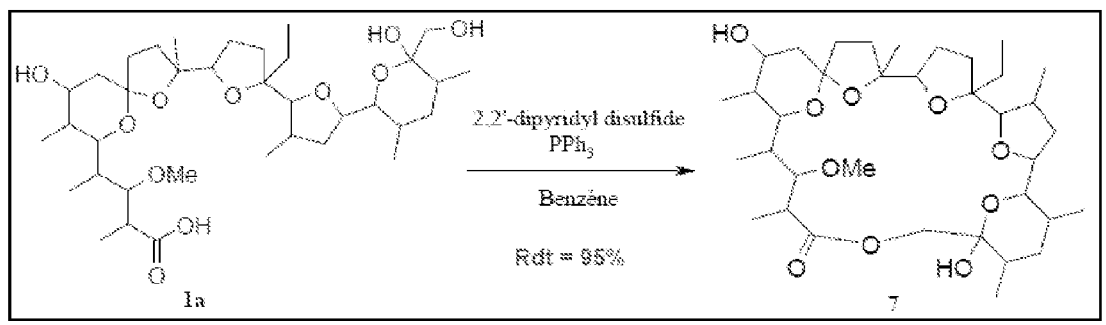
FIG. 8 provides a lactonization reaction.
Figure 9A:
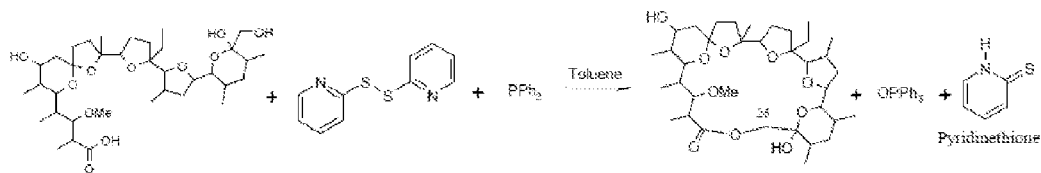
FIG. 9A provides another lactonization reaction.
Figure 9B:
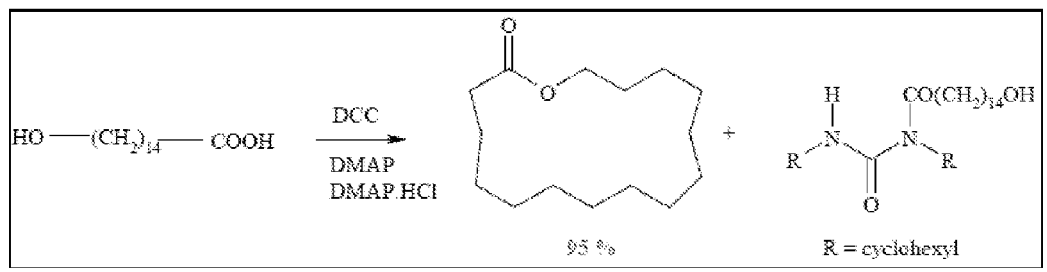
FIG. 9B provides an alternate lactonization reaction.
Figure 9C:
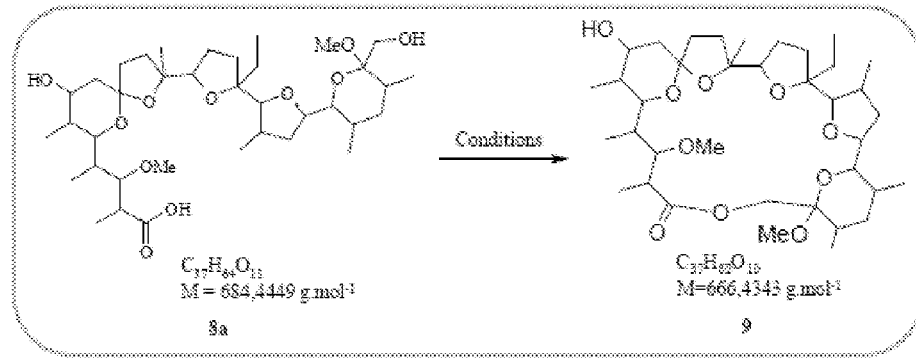
FIG. 9C schematizes lactonization of methylated monensin.
Figure 10A:
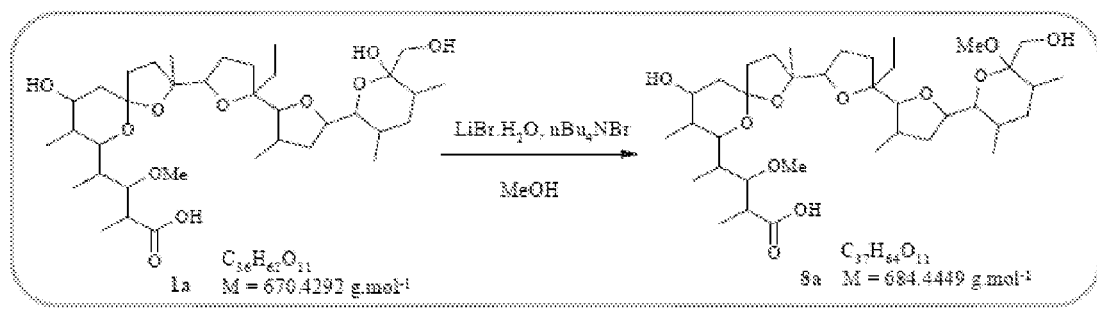
FIG. 10A schematizes etherification of monensin with methanol.
Figure 10B:
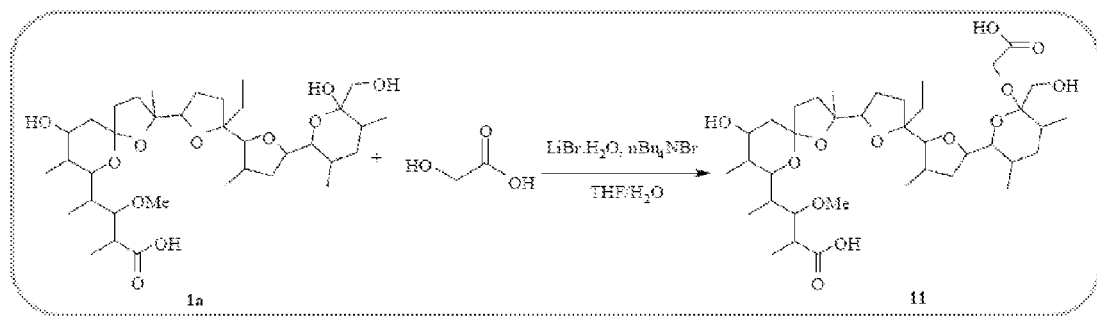
FIG. 10B schematizes etherification of monensin with glycolic acid.
Figure 10C:
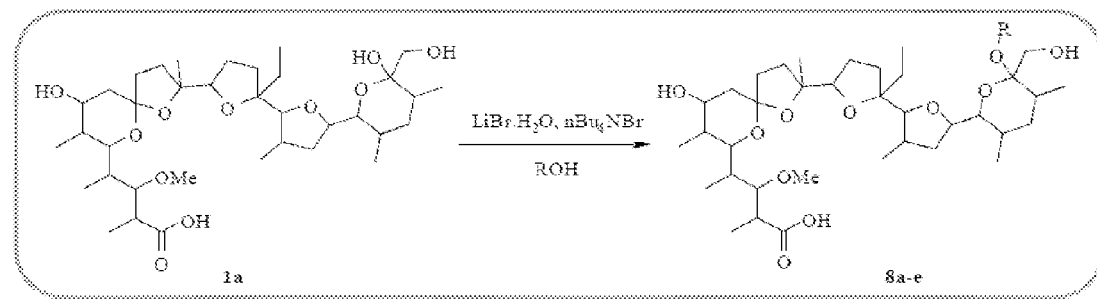
FIG. 10C schematizes etherification of monensin in C25 with alcohols.
Figure 11:
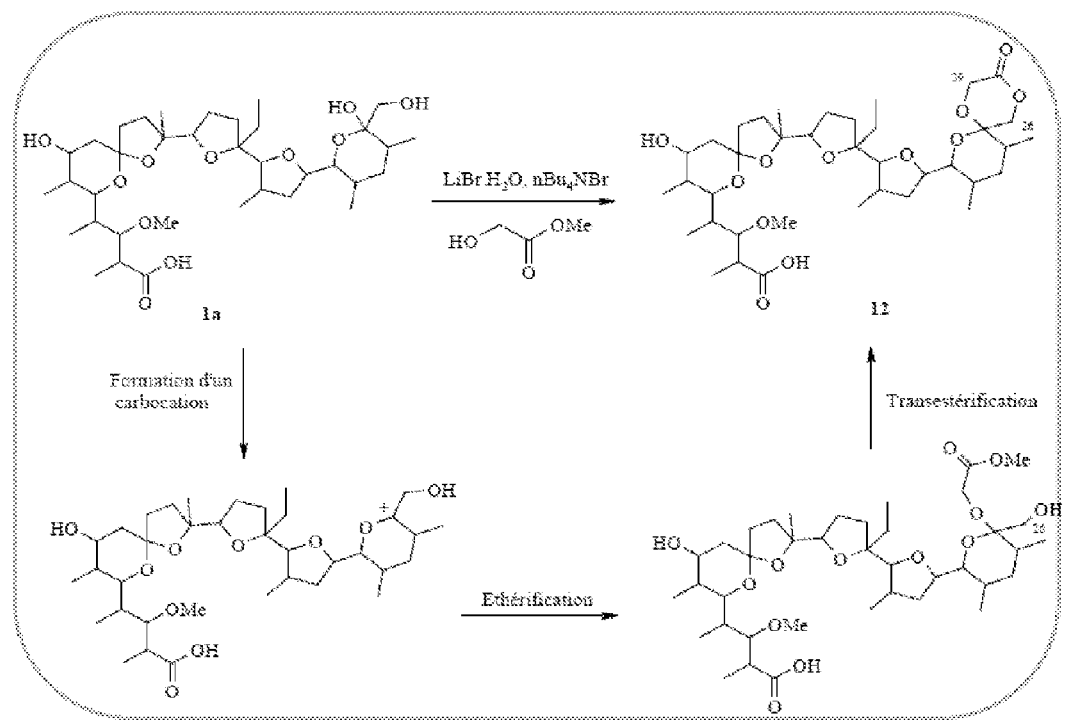
FIG. 11 schematizes probable mechanism whereby (12) is formed from methyl glycolate in the presence of LiBr, water, nBu$_4$Br.
Figure 12:
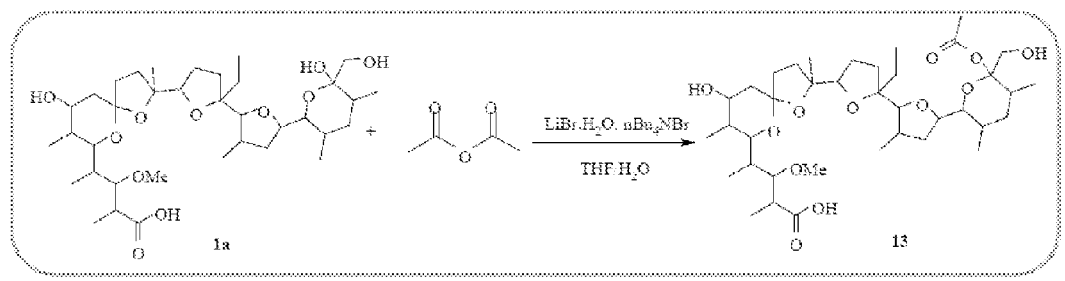
FIG. 12 schematizes acetylation of monensin.
Figure 13:
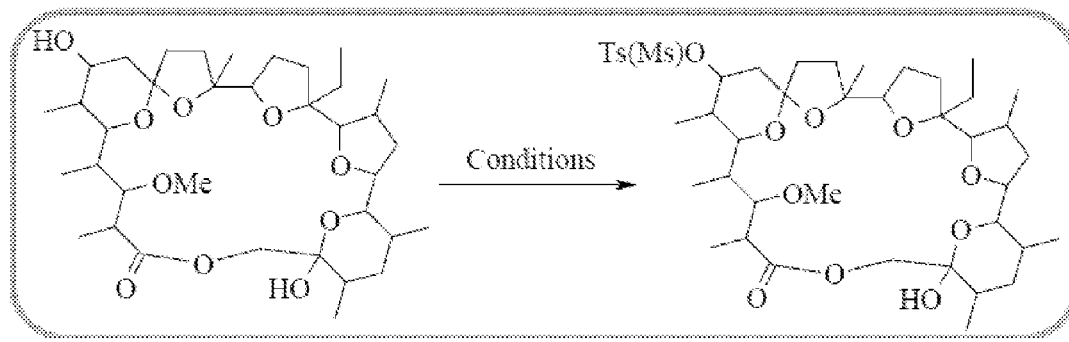
FIG. 13 schematizes tosylation/mesylation of monensin.
Figure 14:
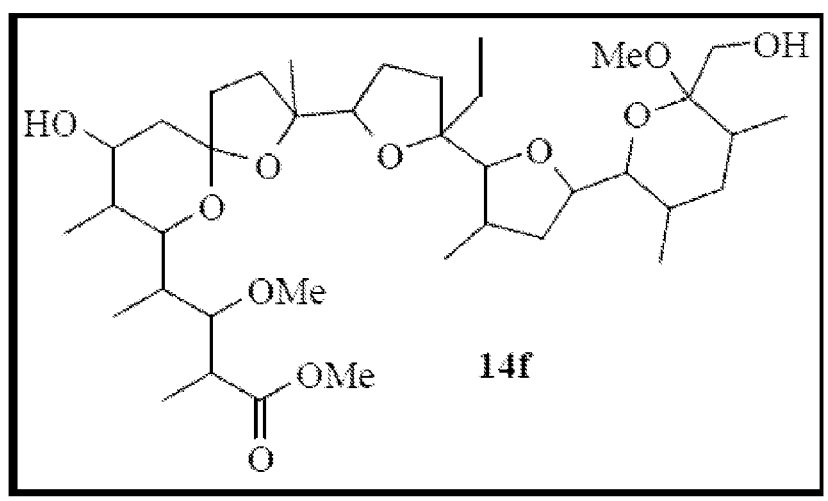
FIG. 14 provides the structure of compound (141)
Figure 15A:
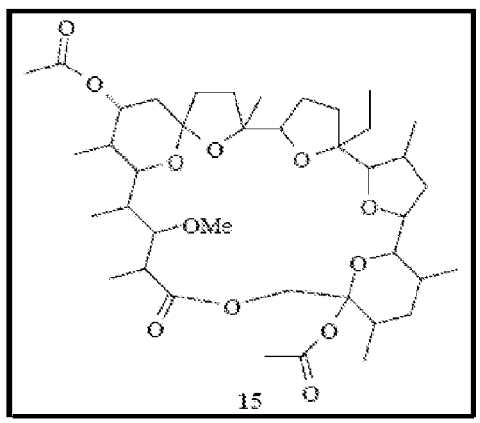
FIG. 15A provides the structure of compound (15)
Figure 15B:
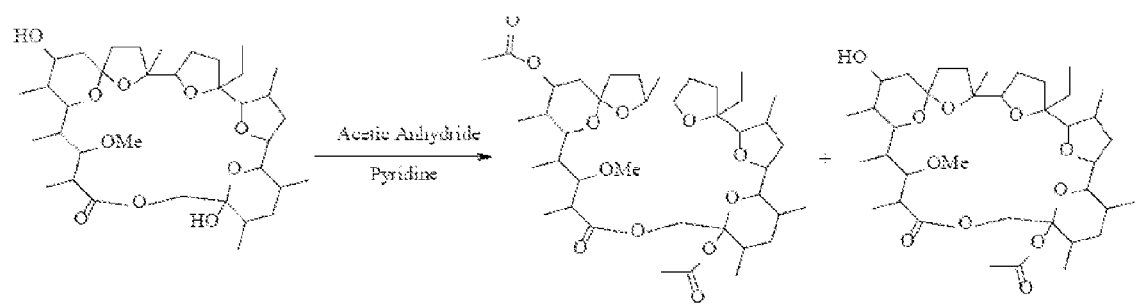
FIG. 15B schematizes acetylation reaction that results in acetylated and diacetylated product.
Figure 16:
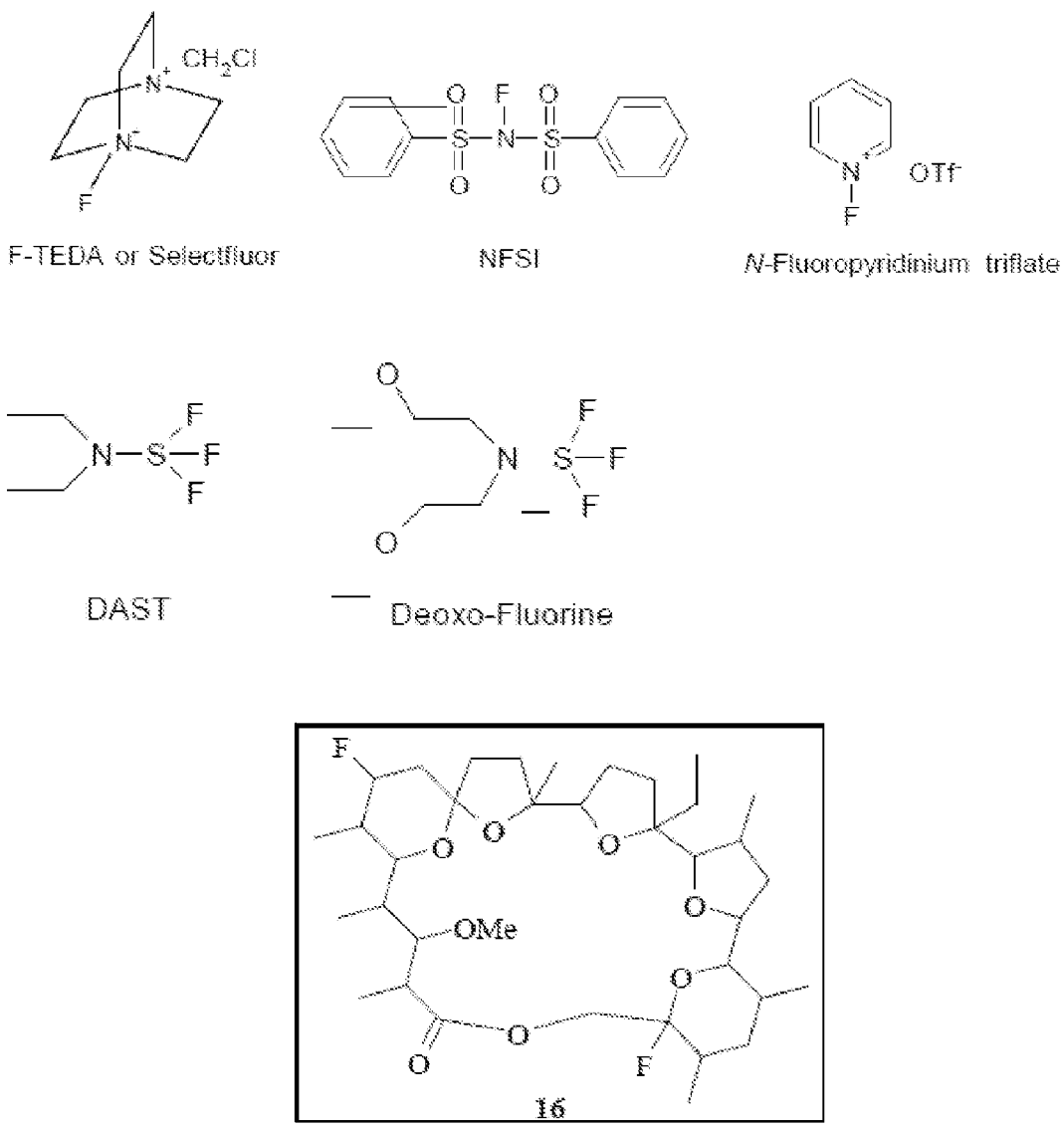
FIG. 16 schematizes monensin lactone fluorinated at C7 and C25 (difluorinated lactone)
Figure 17:
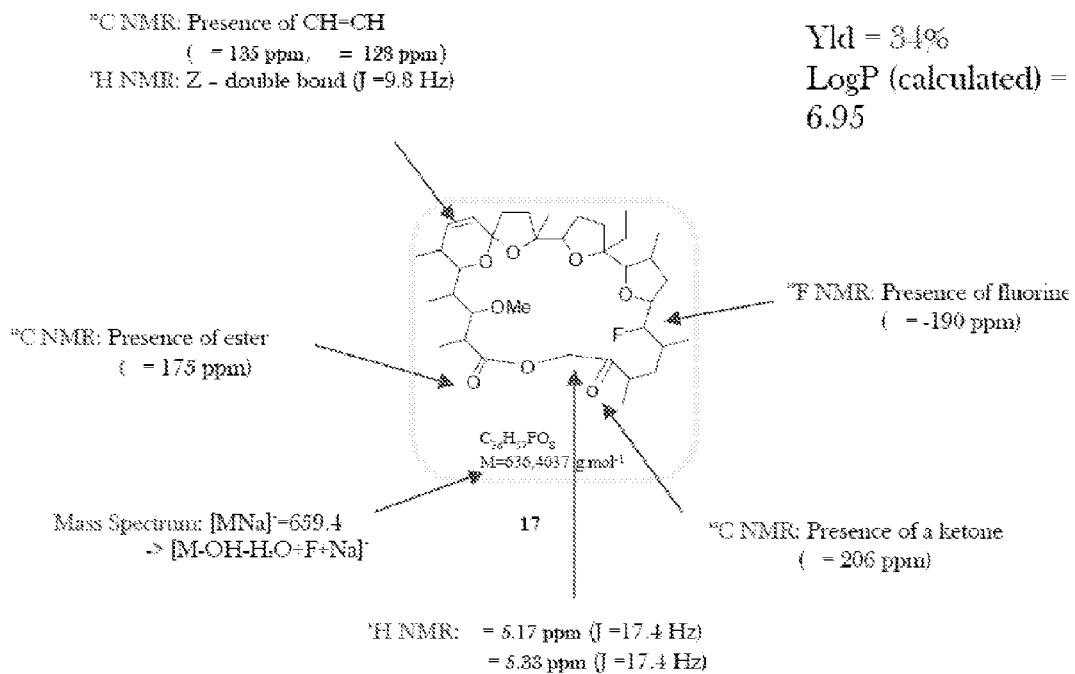
FIG. 17 schematizes compound (17), which is the monofluorinated product.
Figure 18:
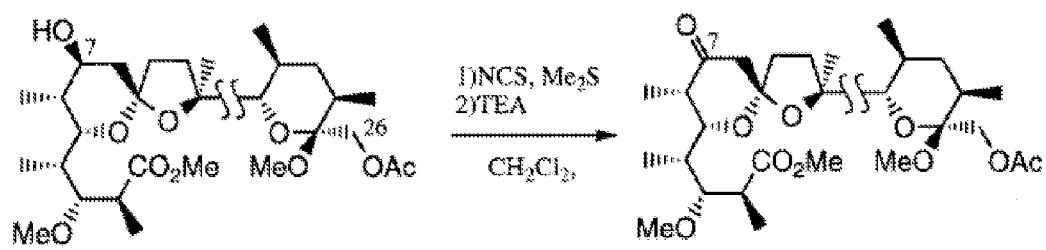
FIG. 18 schematizes oxidation in C7 of the monensin shielded in C1, C25 and C26.
Figure 19:
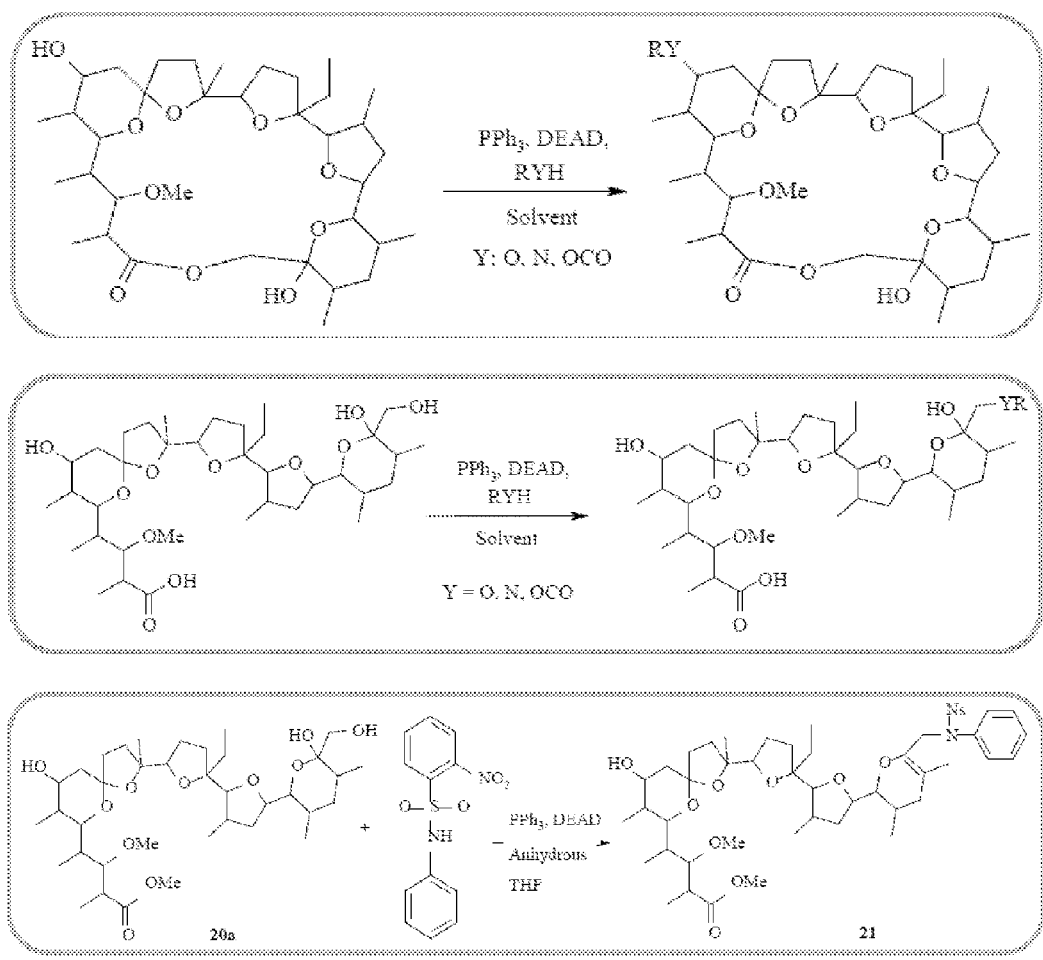
FIG. 19 schematizes the Mitsunobu reaction, which was performed on the lactone (7), monensin (1a), and on esterified monensin (20a)
Figure 20:
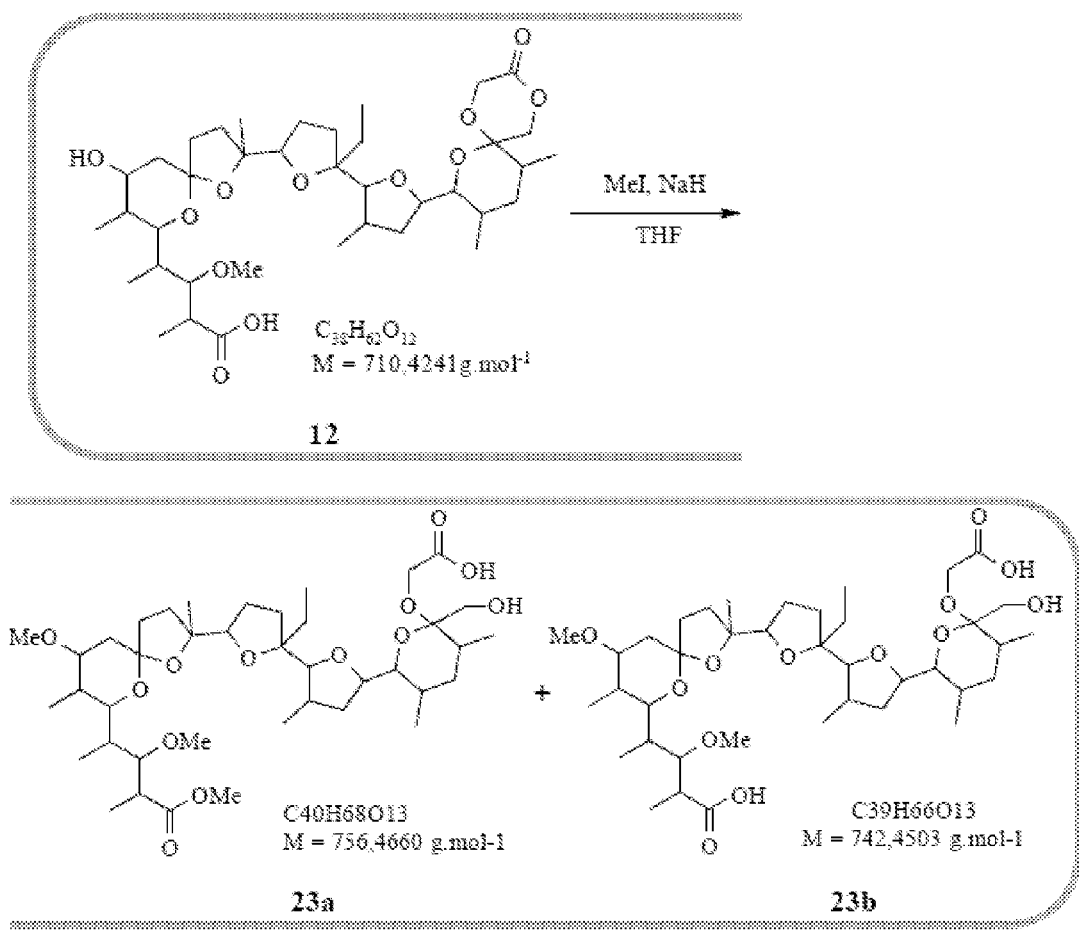
FIG. 20 schematizes etherification of oxodioxane monensin (12) to yield (23a/b)
Figure 21:
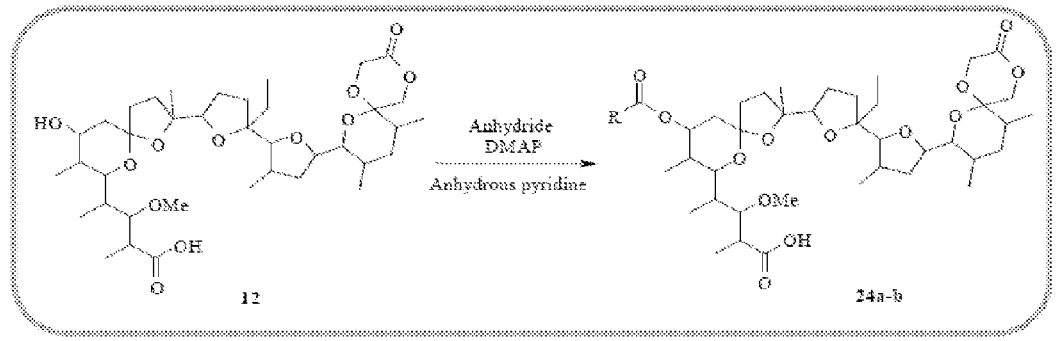
FIG. 21 schematizes esterification of oxodioxane monensin (12) to yield (24a-b)
Figure 22:
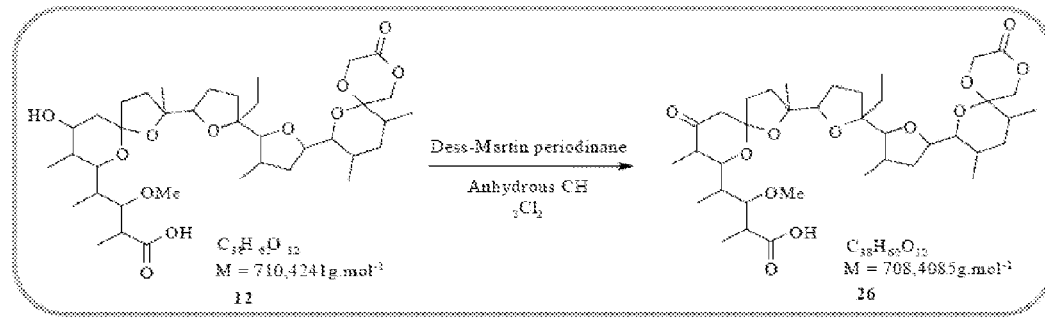
FIG. 22 schematizes oxidation of the oxodioxane monensin (12) to yield (26)
Figure 23:
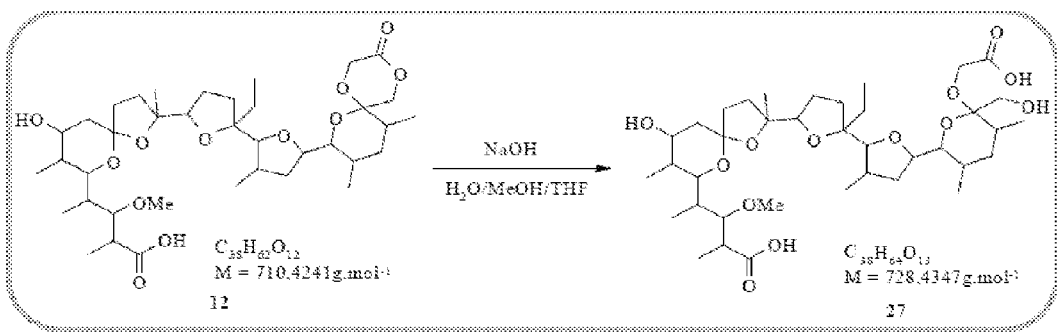
FIG. 23 schematizes saponification of the oxodioxane monensin (12) to yield (27)
Figure 24:
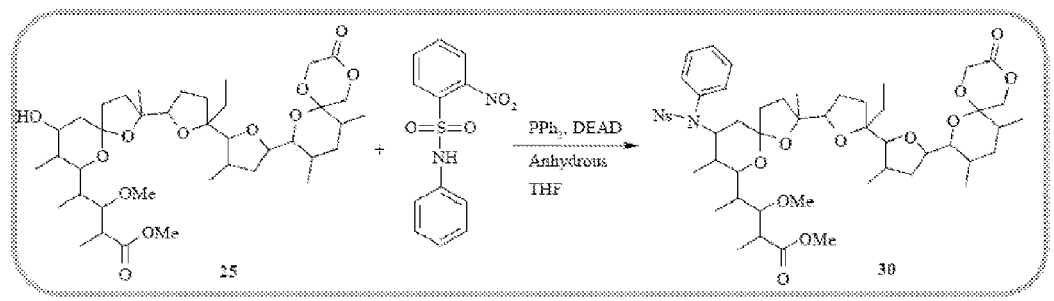
FIG. 24 schematizes Mitsunobu reaction on the methylated oxodioxane monensin (25) in C1 to yield (30)
Figure 25:
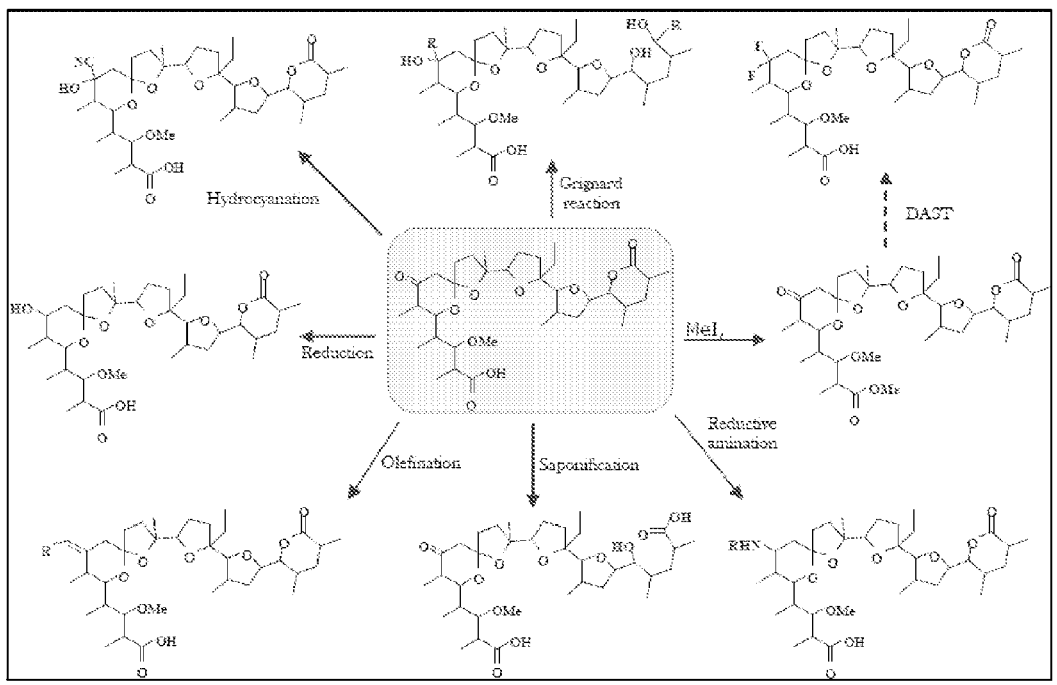
FIG. 25 schematizes multiple synthetic routes beginning with oxidized monensin (19) to arrive at representative members of the families of inventive compounds.

The present invention provides novel polyether ionophore compounds with parasiticidal activity, or pharmaceutically/veterinarily acceptable or pharmaceutically acceptable salts thereof, and compositions comprising the compounds or salts for the treatment or prevention of parasitic infestations and/or infection in an animal or a human. Also provided are methods for the treatment or prevention of parasitic infestations and/or infection in animals or humans, comprising administering an effective amount of the compound of the invention, or a salt thereof, to the animal or human. An important aspect of the invention is to provide polyether ionophore compounds with high potency against parasites, particularly though not solely protists, and improved safety to the user and the environment.

The compounds of the formulae (I) and (II) described herein and their veterinarily acceptable or pharmaceutically acceptable salts are particularly effective for controlling endoparasites, particularly protists such as *Eimeria* spp., *Plasmodia* spp., and the like. Endoparasites include, but are not limited to, nematodes (such as roundworms, hookworms, whipworms and heartworms) and cestodes (tapeworms) and trematodes (flukes). Animal parasites present a serious problem to the health and wellbeing of many animals, including humans, if left uncontrolled. Therefore, the inventive compounds of formulae (I) and (II), veterinarily or pharmaceutically acceptable salts thereof, and compositions comprising the compounds and salts, have substantial utility in controlling and preventing the infestation and/or infection of animals by parasites.

The invention includes at least the following features:

(a) In one embodiment, the invention provides novel compounds of formulae (I) and (II), or veterinarily or pharmaceutically acceptable salts thereof, which are active against animal pests, including parasites;

(b) veterinary and pharmaceutical compositions for combating and controlling parasites comprising parasiticidally effective amount of the compounds of formula (I) or (II), or veterinarily or pharmaceutically acceptable salts thereof, in combination with a veterinarily or pharmaceutically acceptable carrier or diluent;

(c) veterinary and pharmaceutical compositions for combating pests comprising a pesticidally or parasiticidally effective amount of the compounds of the invention, or veterinarily or pharmaceutically acceptable salts thereof, in combination with one more other active agent, including other antiparasitics, and a veterinarily or pharmaceutically acceptable carrier or diluent;

(d) methods for treating a parasitic infestation/infection in or on an animal are provided, which methods comprise administering a parasiticidally effective amount of a compound of formula (I) or (II), or veterinarily acceptable salts thereof, to the animal in need thereof;

(e) methods for the prevention of a parasitic infestation/infection of an animal, which comprise administering a parasiticidally effective amount of a compound of formula (I) or (II), or veterinarily acceptable salts thereof, to the animal in need thereof;

(f) methods for combating or controlling pests at a locus, comprising administering a pesticidally or parasiticidally effective amount of a compound of formula (I) or (II), or veterinarily or pharmaceutically acceptable salts thereof, to the locus;

(g) use of the compounds of formula (I) or (II), or veterinarily acceptable salts thereof, in the manufacture of a veterinary medicament for controlling pests, including parasites; and (h) processes for the preparation of the compounds of formula (I) or (II).

DEFINITIONS

Terms used herein will have their customary meanings in the art unless specified. The organic moieties mentioned in the definitions of the variables of formula (I) or (II) are like the term halogen—i.e., collective terms for individual listings of the individual group members. The prefix $C_n$—$C_m$ indicates in each case the possible number of carbon atoms in the group.

The term "alkyl" refers to saturated straight, branched, cyclic, primary, secondary or tertiary hydrocarbons, including those having 1 to 12 atoms. In some embodiments, alkyl groups will include $C_1$-$C_{10}$, $C_1$-$C_8$, $C_1$-$C_6$ or $C_1$-$C_4$ alkyl groups. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups, which are encompassed by alkyls, may be referred to as "cycloalkyl" and include those with 3 to 10 carbon atoms having single or multiple fused rings. Non-limiting examples of cycloalkyl groups include adamantyl, cyclopropyl, cyclobutyl, cyclopentyl, cyclohexyl, cycloheptyl, cyclooctyl and the like.

The alkyl and cycloalkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamonyl, ester, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the biological activity of the compounds of the invention, either unprotected, or protected as necessary, as known to those skilled in the art, for example, as taught in Greene, et al., Protective Groups in Organic Synthesis, John Wiley and Sons, Third Edition, 1999, hereby incorporated by reference.

The term "alkenyl" refers to both straight and branched carbon chains which have at least one carbon-carbon double bond. In some embodiments, alkenyl groups may include $C_2$-$C_{12}$ alkenyl groups. In other embodiments, alkenyl includes $C_2$-$C_{10}$, $C_2$-$C_8$, $C_2$-$C_6$ or $C_2$-$C_4$ alkenyl groups. In one embodiment of alkenyl, the number of double bonds is 1-3; in another embodiment of alkenyl, the number of double bonds is one. Other ranges of carbon-carbon double bonds and carbon numbers are also contemplated depending on the location of the alkenyl moiety on the molecule. "$C_2$-$C_{10}$-alkenyl" groups may include more than one double bond in the chain. Examples include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Cycloalkenyl" refers to monovalent cyclic alkenyl groups of from 4 to 10 carbon atoms, preferably 5 to 8 carbon atoms, having single or multiple fused rings which fused rings may or may not be cycloalkenyl provided that the point of attachment is to a cycloalkenyl ring atom. Examples of cycloalkenyl groups include, by way of example, cyclopenten-4-yl, cyclooctene-5-yl and the like. Alkenyl and cycloalkenyl groups may be unsubstituted or substituted with one or more substituents as described for alkyl above.

"Alkynyl" refers to both straight and branched carbon chains which have at least one carbon-carbon triple bond. In one embodiment of alkynyl, the number of triple bonds is 1-3; in another embodiment of alkynyl, the number of triple bonds is one. In some embodiments, alkynyl groups include from 2 to 12 carbon atoms. In other embodiments, alkynyl groups may include $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group living 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "haloalkyl" refers to an alkyl group, as defined herein, which is substituted by one or more halogen atoms. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "fluoroalkyl" as used herein refers to an alkyl in which one or more of the hydrogen atoms is replaced with fluorine atoms, for example difluoromethyl, trifluoromethyl, 1-fluoroethyl, 2-fluoroethyl, 2,2-difluoroethyl, 2,2,2-trifluoroethyl, 1,1,2,2-tetrafluoroethyl or pentafluoroethyl.

The term "haloalkenyl" refers to an alkenyl group, as defined herein, which is substituted by one or more halogen atoms.

The term "haloalkynyl" refers to an alkynyl group, as defined herein, which is substituted by one or more halogen atoms.

"Alkoxy" refers to alkyl-O—, wherein alkyl is as defined above. Similarly, the terms "alkenyloxy," "alkynyloxy," "haloalkoxy," "haloalkenyloxy," "haloalkynyloxy," "cycloalkoxy," "cycloalkenyloxy," "halocycloalkoxy," and "halocycloalkenyloxy" refer to the groups alkenyl-O—, alkynyl-O—, haloalkyl-O—, haloalkenyl-O—, haloalkynyl-O—, cycloalkyl-O—, cycloalkenyl-O—, halocycloalkyl-O—, and halocycloalkenyl-O—, respectively, wherein alkenyl, alkynyl, haloalkyl, haloalkenyl, haloalkynyl, cycloalkyl, cycloalkenyl, halocycloalkyl, and halocycloalkenyl are as defined above. Examples of $C_1$-$C_6$-alkoxy include, but are not limited to, methoxy, ethoxy, $OCH_2$—$C_2H_5$, $OCH(CH_3)_2$, n-butoxy, $OCH(CH_3)$—$C_2H_5$, $OCH_2$—$CH(CH_3)_2$, $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

"Aryl" refers to a monovalent aromatic carbocyclic group of from 6 to 14 carbon atoms having a single ring or multiple fused rings. Aryl groups include, but are not limited to, phenyl, biphenyl, and naphthyl. In some embodiments aryl includes tetrahydronapthyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, alkylamino, alkenylamino, alkynylamino, di(alkyl)amino, di(alkenyl)amino, di(alkynyl)amino, or trialkylsilyl.

The term "aralkyl" refers to an aryl group that is bonded to the parent compound through a diradical alkylene bridge, (—$CH_2$—)., where n is 1-12 and where "aryl" is as defined above.

"Heteroaryl" refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple fused rings provided that the point of attachment is through a heteroaryl ring atom. Examples of heteroaryls include pyridyl, piridazinyl, pyrimidinyl, pyrazinyl, triazinyl, pyrrolyl, indolyl, quinolinyl, isoquinolinyl, quinazolinyl, quinoxalinnyl, furanyl, thiophenyl, furyl, pyrrolyl, imidazolyl, oxazolyl, isoxazolyl, isothiazolyl, pyrazolyl benzofuranyl, and benzothiophenyl. Heteroaryl rings may be unsubstituted or substituted by one or more moieties as described for aryl above.

"Heterocyclyl," "heterocyclic" or "heterocyclo" refers to fully saturated or unsaturated, cyclic groups, for example, 3 to 7 membered monocyclic, 7 to 11 membered bicyclic, or 10 to 15 membered tricyclic ring systems, which have one or more oxygen, sulfur or nitrogen heteroatoms in ring, preferably 1 to 4 or 1 to 3 heteroatoms. The nitrogen and sulfur heteroatoms may optionally be oxidized and the nitrogen heteroatoms may optionally be quaternized. The heterocyclic group may be attached at any heteroatom or carbon atom of the ring or ring system and may be unsubstituted or substituted by one or more moieties as described for aryl groups above.

Exemplary monocyclic heterocyclic groups include, but are not limited to, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

The term "alkylthio" or "alkylsulfanyl" refers to alkyl-S—, where "alkyl" is as defined above. In some embodiments, the alkyl component of the alkylthio group will include $C_1$-$C_{10}$, $C_1$-$C_8$, $C_1$-$C_6$ or $C_1$-$C_4$ alkyl groups. For example, $C_1$-$C_4$-alkylthio include, but are not limited to, methylthio, ethylthio, propylthio, 1-methylethylthio, butylthio, 1-methylpropylthio, 2-methylpropylthio or 1,1-dimethylethylthio. Similarly, the terms "haloalkylthio," "cycloalkylthio," "halocycloalkylthio" refer to the groups —S-haloalkyl, —S-cycloalkyl, and —S-halocycloalkyl, respectively, where the terms "haloalkyl," "cycloalkyl," and "halocycloalkyl" are as defined above.

The term "alkylsulfinyl" refers to the group alkyl-S(=O)—, where "alkyl" is as defined above. In some embodiments, the alkyl component in alkylsulfinyl groups will include $C_1$-$C_{12}$, $C_1$-$C_{10}$, $C_1$-$C_6$ or $C_1$-$C_4$ alkyl groups. Examples include, but are not limited to, —SO—$CH_3$, —SO—$C_2H_5$, n-propylsulfinyl, 1-methylethylsulfinyl, n-butylsulfinyl, 1-methylpropylsulfinyl, 2-methylpropylsulfinyl, 1,1-dimethylethylsulfinyl, n-pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, n-hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl.

Similarly, the terms "alkenylfulfinyl," "alkynylsulfinyl," "haloalkylsulfinyl," "haloalkenylsulfinyl," and "haloalkynylsulfinyl" refer to the groups alkenyl-S(=O)—, alkynyl-S(=O)—, and haloalkyl-S(=O)—, haloalkenyl-S(=O)—, and haloalkynyl-S(=O)—, where the terms "alkenyl," "alkynyl," "haloalkyl," "haloalkenyl," and "haloalkynyl" are as defined above. The term "alkylsulfonyl" refers to the group alkyl-S(=O)$_2$—, where the term "alkyl" is as defined above. In some embodiments, the alkyl component in alkylsulfonyl groups will include $C_1$-$C_{12}$, $C_1$-$C_{10}$, $C_1$-$C_8$, $C_1$-$C_6$ or $C_1$-$C_{10}$ alkyl groups. Examples include, but are not limited to, —$SO_2$—$CH_3$, —$SO_2$—$C_2H_5$, n-propylsulfonyl, —$SO_2$—$CH(CH_3)_2$, n-butylsulfonyl, 1-methylpropylsulfonyl, 2-methylpropylsulfonyl, —$SO_2$—$C(CH_3)_3$, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl and the like.

The terms "alkenylfulfonyl," "alkynylsulfonyl," "haloalkylsulfonyl," "haloalkenylsulfonyl," and "haloalkynylsulfonyl" refer to the groups alkenyl-S(=O)$_2$—, alkynyl-S(=O)$_2$—, and haloalkyl-S(=O)$_2$—, haloalkenyl-S(=O)$_2$—, andhaloalkynyl-S(=O)$_2$—, where the terms "alkenyl," "alkynyl," "haloalkyl," "haloalkenyl," and "haloalkynyl" are as defined above. The terms "alkylamino," "dialkylamino," "alkenylamino," "alkynylamino," "di(alkenyl)amino," and "di(alkynyl)amino" refer to the groups —NH(alkyl), —N(alkyl)$_2$, —NH(alkenyl), —NH(alkynyl), —N(alkenyl)$_2$ and —N(alkynyl)$_2$, where the terms "alkyl," "alkenyl," and "alkynyl" are as defined above. In some embodiments, the alkyl component in alkylamino or dialkylamino groups will include $C_1$-$C_{12}$, $C_1$-$C_{10}$, $C_1$-$C_8$, $C_1$-$C_6$ or $C_1$-$C_4$ alkyl groups.

The term "trialkylsilyl" refers to the group —Si(alkyl)$_3$, where the group is bonded to the parent compound at the silicon atom.

Compounds of the Invention

The compounds of the invention are polyether ionophore compounds, which have potent activity against parasites, including protists such as *Eimeria* and *Plasmodia*. In certain embodiments, the compounds of the invention are useful in veterinary applications, including for controlling parasites in or on an animal. In other embodiments, the inventive compounds are useful in pharmaceutical applications for preventing or controlling human pathogens such as *Plasmodium falciparum*.

In one embodiment the invention provides a polyether ionophore compound of formula (I), or a veterinarily or pharmaceutically acceptable salt thereof:

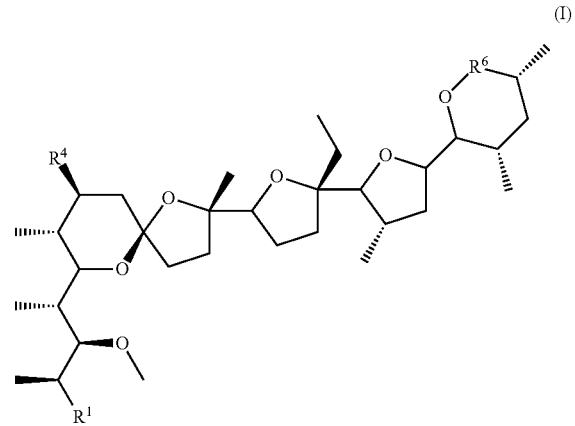

wherein
$R^1$ is C(=O)$OR^2$, C(=O)$NR^2$, C(=O)OH, $CH_2OH$, $CH_2NR_2^2$, $CH_2SR^2$, C(=O)H, halogen, $CH_2OR^2$, alkyl, aryl, aralkyl, heteroaryl, heterocyclyl, or salts of amines and carboxylates;

$R^2$ is H, C, alkyl, aryl, aralkyl, heteroaryl, alcohols, amine, aldehyde, or heterocyclyl;

$R^4$ is $OR^5$, O(C=O)$R^5$, F, (=O), OH, halogen, alkyl, aryl, aralkyl, heteroaryl, or heterocyclyl;

$R^6$ is C($R^7$)$R^8$, C(=O), alkyl, aryl, aralkyl, heteroaryl, or heterocyclyl;

$R^7$ is hydroxyl, methylhydroxyl, alkoxy, alkyl, aryl, aralkyl, heteroaryl, or heterocyclyl;

$R^8$ is hydroxyl, methylhydroxyl, alkoxy, alkyl, aryl, aralkyl, heteroaryl, or heterocyclyl; or $R^7$ and $R^8$ combine to form 3, 4, 5, or 6-membered rings, comprising 0, 1, or 2 oxygen(s).

In another embodiment the invention provides a polyether ionophore compound of formula (II), or a veterinarily or pharmaceutically acceptable salt thereof:

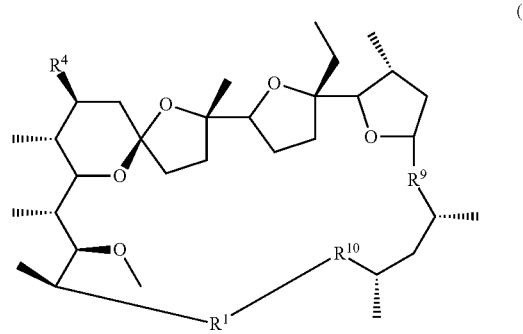

(II)

wherein
$R^1$ is C(=O)O, C(=O)$NR_2^2$, alkyl, aryl, aralkyl, heteroaryl, or heterocyclyl;
$R^4$ is hydroxyl, halogen, (=O), $OR^S$, O(C=O)$R^5$, F, alkyl, aryl, aralkyl, heteroaryl, or heterocyclyl;
$R^9$ is C(=O)O or CHF;
$R^{10}$ is C or C(=O);
or $R^9$ and $R^{10}$ are CH are connected to each other by O.

For convenience, certain terms employed in the Specification, Examples, and appended Claims are collected here.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicates otherwise.

As used herein, the word "about", where it is specifically used to describe a concentration, a mass, a weight, or a volume, is hereby defined to mean "plus or minus 10%" of the stated value.

The following abbreviations shall have the indicated meanings: AcOH=Acetic acid; PTSA=p-Toluenesulphonic acid; DAST=Diethylaminosulphur trifluoride DCC=Dicyclohexylcarbodiimide; DCM=Dichloromethane; DEPT=Distortionless Enhancement by Polarisation Transfer; DIEA=Diisopropylethylamine; DMAP=Dimethylaminopyridine; DMF=Dimethylformamide; DMSO=Dimethyl sulphsulphoxide EtOH=Ethanol; Eq=Equivalent; FDPP=Pentafluorophenyl diphenyl phosphinate; HOBt=Hydroxybenzotriazole; HPLC=High Pressure Liquid Chromatography; MeOH=Methanol; MS=Mass spectrometry; MS4A=Molecular sieves 4 Angstrom; MsCl=Mesyl chloride; NBS=N-Bromosuccinimide; NCS=N-Chlorosuccinimide Pyr=Pyridine; Yld=Yield; Rf=Retardation factor; NMR=Nuclear Magnetic Resonance; XR=X-ray; t=Time; A.T.=Ambient temperature; TBAF=Tetrabutylammonium fluoride; TEA=Triethylamine; THF=Tetrahydrofuran; Rt=Retention time; TsCl=Tosyl chloride; TSA=Toluene sulphsulphonic acid; Vol.=Volume; COSY (Correlation Spectroscopy); $^1H$-$^1H$ homonuclear scalar coupling; NOESY (Nuclear Overhauser Effect Spectroscopy): $^1H$-$^1H$ homonuclear spatial coupling; HMBC (Heteronuclear Multiple Bond Correlation): $^1H$-$^{13}C$ long-distance correlation; HSQC-TOCSY (Heteronuclear Multiple Quantum Correlation-Total Correlation Spectroscopy.

As used herein, the term "animal" includes all vertebrate animals including humans. It also includes an individual animal in all stages of development, including embryonic and fetal stages. In particular, the term "vertebrate animal" includes, but not limited to, humans, canines (e.g., dogs), felines (e.g., cats); equines (e.g., horses), bovines (e.g., cattle), ovine (e.g., sheep), porcine (e.g., pigs), as well as avians. The term "avian" as used herein refers to any species or subspecies of the taxonomic class ava, such as, but not limited to, chickens (breeders, broilers and layers), turkeys, ducks, a goose, a quail, pheasants, parrots, finches, hawks, crows and ratites including ostrich, emu and cassowary, and includes all avians kept as either companion or production animals.

As used herein, the term "aqueous suspension" includes mixtures of insoluble particles in water. Aqueous suspensions may contain the active material in admixture with excipients suitable for the manufacture of aqueous suspensions. Such excipients are suspending agents, for example, colloidal silica, sodium carboxymethylcellulose, methylcellulose, xanthan gum, hydroxy-propylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

It will be understood by those of skill in the art that compounds of formula (I) may also be prepared by derivatization of other compounds (I) or by customary modifications of the synthesis routes described.

When the compounds of formula (I) or (II) contain suitably acidic or basic residues that enable the formation of veterinarily or pharmaceutically acceptable salts, the compounds may be reacted with suitable acids such as hydrochloric acid, hydrobromic acid, hydroiodic acid, sulfuric acid, phosphoric acid, formic acid, acetic acid, oxalic acid, benzene sulfonic acid, p-toluene sulfonic acid, dodecylbenzene sulfonic acid, methyl bromide, dimethyl sulfate or diethyl sulfate, and the like, typically at a temperature range of about −5° C. to about 150° C., preferably about 0 to about 20° C., in a suitable solvent.

Alternatively, compounds of formula (I) or (II) that contain acidic residues may be reacted with suitable bases, including organic amine bases or inorganic bases such as hydroxides, carbonates or bicarbonates of alkali metals or alkaline earth metals.

The formation of the salt is usually conducted in a dissolving or diluting agent. Suitable are e.g. aliphatic hydrocarbons as n-pentane, n-hexane or petrol ether, aromatic hydrocarbons, as toluene or xylenes, or ethers such as diethyl ether, methyl-tert.-butyl ether, tetrahydrofuran or dioxane, further ketones, as acetone, methyl-ethyl-ketone or methyl-isopropyl-ketone, as well as halogenated hydrocarbons as chlorobenzene, methylene chloride, ethylene chloride, chloroform or tetrachloroethylene. Also mixtures of those solvents can be used.

For the preparation of salts of compounds of formula (I) or (II) the compounds and salt forming agents are employed usually in a stoichiometric ratio. The excess of one or the other component can be useful.

If individual compounds cannot be prepared via the above-described routes, they can be prepared by derivatization of other compounds or by customary modifications of the synthesis routes described.

The reaction mixtures are typically worked up in a customary manner, for example by mixing a reaction product mixture containing an organic solvent with water, separating the phases, and, if appropriate, purifying the crude products by chromatography, for example on alumina or silica gel. If the intermediates and end products are obtained as solids, they may be purified by recrystallization or digestion.

Animal Health Applications:

One important aspect of the invention is the use of the compounds of formula (I) or (II) or compositions comprising the compounds for the treatment of parasite infestation/infection in or on animals. The compositions of the invention comprise an effective amount of at least one compound of formula (I) or (II) in combination with a veterinarily acceptable carrier or diluent and optionally other non-active excipients. The compositions may be in a variety of solid and liquid forms which are suitable for various forms of application or administration to an animal. For example, the veterinary compositions comprising the inventive compounds may be in formulations suitable for oral administration, injectable administration, including subcutaneous and parenteral administration, and topical, pour-on, dermal or subdermal administration. The formulations are intended to be administered to an animal including, but is not limited to, mammals, birds and fish. Examples of mammals include but are not limited to humans, cattle, sheep, goats, llamas, alpacas, pigs, horses, donkeys, dogs, cats and other livestock or domestic mammals. Examples of birds include turkeys, chickens, ostriches and other livestock or domestic birds.

Veterinary Compositions:

As discussed above, the compositions of the invention may be in a form suitable for oral use (see, e.g., U.S. Pat. No. 4,564,631, which is hereby incorporated by reference in its entirety), dietary supplements, troches, lozenges, chewables, tablets, hard or soft capsules, bolus, emulsions, aqueous or oily suspensions, aqueous or oily solutions, oral formulations, dispersible powders or granules, premixes, syrups or elixirs, enteric formulations or pastes. Compositions intended for oral use may be prepared according to any method known in the art for the manufacture of pharmaceutical compositions and such compositions may contain one or more sweetening agents, bittering agents, flavoring agents, coloring agents and preserving agents in order to provide pharmaceutically elegant and palatable preparations.

Oral products administered to avians are typically, but not exclusively, premix (powder mixed flour) or liquid. A premix product can comprise corn grits or wheat flour, along with appropriate excipients, including preservatives such as antioxidants, and emollients, oils, texturizers, and the like. Inventive formulations may be administered via drinking water, for example, in a chick hatchery setting. Surfactants may be included in such aqueous formulations, both to encourage the inventive compounds to remain in solution prior to being added to the drinking water, and to facilitate even mixing with same.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874 (all incorporated herein by reference in their entirety) to form osmotic therapeutic tablets for controlled release.

Oral formulations include hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, PEGs and ethanol, or an oil medium, for example peanut oil, liquid paraffin, or olive oil.

The compositions of the invention may also be in the form of oil-in-water or water-in-oil emulsions. The oily phase maybe a vegetable oil, for example, olive oil or arachis oil, or a mineral oil, for example, liquid paraffin or mixtures of these. Suitable emulsifying agents include naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, and/or preservatives.

In one embodiment, the composition of the invention may be in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids.

Microemulsions are composed of stable dispersions of microdroplets of the aqueous phase in the oily phase or conversely of microdroplets of the oily phase in the aqueous phase. The size of these microdroplets may be less than 200 nm (1000 to 100,000 nm for emulsions). The interfacial film may be composed of an alternation of surface-active (SA) and co-surface-active (Co-SA) molecules which, by lowering the interfacial tension, allows the microemulsion to be formed spontaneously.

In one embodiment of the oily phase, the oily phase may be formed from mineral or vegetable oils, from unsaturated polyglycosylated glycerides or from triglycerides, or alternatively from mixtures of such compounds. In one embodiment of the oily phase, the oily phase may be comprised of triglycerides; in another embodiment of the oily phase, the triglycerides are medium-chain triglycerides, for example $C_8$-$C_{10}$ caprylic/capric triglyceride. In another embodiment of the oily phase may represent a % v/v range of about 2 to about 15%; about 7 to about 10%; and about 8 to about 9% v/v of the microemulsion.

The aqueous phase may include, for example water or glycol derivatives, such as propylene glycol, glycol ethers, polyethylene glycols or glycerol. In one embodiment, the glycol may be propylene glycol, diethylene glycol monoethyl ether, dipropylene glycol monoethyl ether or mixtures thereof. Generally, the aqueous phase will represent a proportion from about 1 to about 4% v/v in the microemulsion.

Surfactants for the microemulsion may include diethylene glycol monoethyl ether, dipropyelene glycol monomethyl ether, polyglycolyzed $C_8$-$C_{10}$ glycerides or polyglyceryl-6 dioleate. In addition to these surfactants, the cosurfactants may include short-chain alcohols, such as ethanol and propanol.

Some compounds are common to the three components discussed above, i.e., aqueous phase, surfactant and cosurfactant. However, it is well within the skill level of the practitioner to use different compounds for each component of the same formulation. In one embodiment for the amount of surfactant/cosurfactant, the cosurfactant to surfactant ratio will be from about 1/7 to about 1/2. In another embodiment for the amount of cosurfactant, there will be from about 25 to about 75% v/v of surfactant and from about 10 to about 55% v/v of cosurfactant in the microemulsion.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an anti-oxidant such as ascorbic acid, or other known preservatives.

Aqueous suspensions may contain the active material in admixture with excipients suitable for the manufacture of aqueous suspensions. Such excipients include suspending agents, for example, sodium carboxymethylcellulose, methylcellulose, hydroxy-propylmethylcellulose, sodium alginate, polyinylpyrrolidone, gum tragacanth and gum acacia; dispersing or wetting agents include naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water may provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such formulations may also contain a demulcent, a preservative, flavoring agent(s) and/or coloring agent(s).

In another embodiment of the invention, the composition may be in paste form. Examples of embodiments in a paste form include, but are not limited to, those described in U.S. Pat. Nos. 6,787,342 and 7,001,889 (each of which are incorporated herein by reference). In addition to the compounds of the invention, the paste may further contain fumed silica; a viscosity modifier; a carrier; optionally, an absorbent; and optionally, a colorant, stabilizer, surfactant, or preservative.

In one embodiment of the formulation, the formulation may be a paste containing the compounds of the invention, fumed silica, a viscosity modifier, an absorbent, a colorant; and a hydrophilic carrier which is triacetin, a monoglyceride, a diglyceride, or a triglyceride.

The paste may also include a viscosity modifier. Suitable viscosity modifiers include, but are not limited to, polyethylene glycols (PEG) including, but not limited to, PEG 200, PEG 300, PEG 400, PEG 600; monoethanolamine, triethanolamine, glycerol, propylene glycol, polyoxyethylene (20) sorbitan mono-oleate (polysorbate 80 or Tween 80), or polyoxamers (e.g., Pluronic L 81); an absorbent such as magnesium carbonate, calcium carbonate, starch, and cellulose and its derivatives; and a colorant including, but not limited to, titanium dioxide iron oxide, or FD&C Blue #1 Aluminum Lake.

In some embodiments, the compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol, glycerol formal or polyethylene glycols may also be used. Preservatives, such as phenol or benzyl alcohol, may be used.

In addition, sterile, fixed oils may be conventionally employed as a solvent or suspending medium. For this purpose any bland fixed oil may be employed including synthetic mono- or diglycerides. In addition, fatty acids such as oleic acid find use in the preparation of injectables.

Topical, dermal and subdermal formulations may include, by way of non-limiting example, emulsions, creams, ointments, gels, pastes, powders, shampoos, pour-on formulations, ready-to-use formulations, spot-on solutions and suspensions, dips and sprays. Topical application of an inventive compound or of a composition including at least one inventive compound among active agent(s) therein, in the form of a spot-on, spray-on or pour-on composition, may allow for the inventive composition to be absorbed through the skin to achieve systemic levels, distributed through the sebaceous glands or on the surface of the skin achieving levels throughout the coat. When the compound is distributed through the sebaceous glands, they may act as a reservoir, whereby there may be a long-lasting effect (up to several months) effect. Spot-on formulations are typically applied in a localized region which refers to an area other than the entire animal. In one embodiment, the location may be between the shoulders. In another embodiment it may be a stripe, e.g. a stripe from head to tail of the animal.

Pour-on formulations are described in U.S. Pat. No. 6,010,710, also incorporated herein by reference. Pour-on formulations may be advantageously oily, and generally comprise a diluent or vehicle and also a solvent (e.g. an organic solvent) for the active ingredient if the latter is not soluble in the diluent.

Organic solvents that can be used in the invention include, but are not limited to, acetyltributyl citrate, fatty acid esters such as the dimethyl ester, diisobutyl adipate, acetone, acetonitrile, benzyl alcohol, ethyl alcohol, butyl diglycol, dimethylacetamide, dimethylformamide, dimethyl sulfoxide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol, triacetin, $C_1$-$C_{10}$ esters of carboxylic acids such as butyl or octyl acetate, and diethyl phthalate, or a mixture of at least two of these solvents.

The solvent will be used in proportion with the concentration of the active agent compound and its solubility in this solvent. It will be sought to have the lowest possible volume. The vehicle makes up the difference to 100%.

A vehicle or diluent for the formulations may include dimethyl sulfoxide (DMSO), glycol derivatives such as, for example, propylene glycol, glycol ethers, polyethylene glycols or glycerol. As vehicle or diluent, mention may also be made of plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as $C_8$ to $C_{12}$) triglycerides.

In another embodiment of the invention, an emollient and/or spreading and/or film-forming agent may be added. In one embodiment, the emollient and/or spreading and/or film-forming agent may be:

(a) polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil, (b) anionic surfactants such as alkaline stearates, sodium, potassium or ammonium stearates; calcium stearate, triethanolamine stearate; sodium abietate; alkyl sulphates (e.g. sodium lauryl sulphate and sodium cetyl sulphate); sodium dodecylbenzenesulphonate, sodium dioctylsulphosuccinate; fatty acids (e.g. those derived from coconut oil), (c) cationic surfactants include water-soluble quaternary ammonium salts of formula N$^+$R'R"R'''R'''', Y$^-$ in which the radicals R are optionally hydroxylated hydrocarbon radicals and Y$^-$ is an anion of a strong acid such as the halide, sulphate and sulphonate anions; cetyltrimethylammonium bromide is among the cationic surfactants which can be used, (d) amine salts of formula N$^+$HR'R"R''' in which the radicals R are optionally hydroxylated hydrocarbon radicals; octadecylamine hydrochloride is among the cationic surfactants which can be used, (e) nonionic surfactants such as sorbitan esters, which are optionally polyoxyethylenated (e.g. polysorbate 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (f) amphoteric surfactants such as the substituted lauryl compounds of betaine; or (g) a mixture of at least two of these agents.

In one embodiment of the amount of emollient, the emollient used may be in a proportion of from about 0.1 to 50% or 0.25 to 5%, by volume. In another embodiment, the emollient used may be in a proportion of from about 0.1% to about 30%, about 1% to about 30%, about 1% to about 20%, or about 5% to about 20% by volume.

In another embodiment of the invention, the composition may be in ready-to-use solution form as is described in U.S. Pat. No. 6,395,765, incorporated herein by reference. In addition to the compounds of the invention, the ready-to-use solution may contain a crystallization inhibitor and an organic solvent or a mixture of organic solvents. In some embodiments, water may be included with the organic solvent.

In various embodiments of the invention, the compositions may include a crystallization inhibitor in an amount of about 1 to about 50% (w/v) or about 5 to about 40% (w/v) based on the total weight of the formulation. In other embodiments, the amount of crystallization inhibitor in the inventive formulations may be about 1% to about 30%, about 5% to about 20%, about 1% to about 15%, or about 1% to about 10% (w/w). The type of crystallization inhibitor used in the inventive formulations is not limited as long as it functions to inhibit crystallization of the active or inactive agents from the formulation. For example, in certain embodiments of the invention, a solvent or co-solvent of the formulation may also function as a crystallization inhibitor if it sufficiently inhibits the formation of crystals from forming over time when the formulation is administered.

Crystallization inhibitors which are useful for the invention include, but are not limited to:

(a) polyvinylpyrrolidone, polyvinyl alcohols, copolymers of vinyl acetate and vinylpyrrolidone, polyethylene glycols, benzyl alcohol, dimethylformamide, dimethylacetamide, dimethylsulfoxide, 2-pyrrolidone, N-methylpyrrolidone, mannitol, glycerol, sorbitol or polyoxyethylenated esters of sorbitan; lecithin or sodium carboxymethylcellulose; or acrylic derivatives, such as acrylates or methacrylates or polymers or copolymers thereof, polyethyleneglycols (PEG) or polymers containing polyethyleneglycols, such as glycofurol and the like, and others;

(b) anionic surfactants, such as alkaline stearates (e.g. sodium, potassium or ammonium stearate); calcium stearate or triethanolamine stearate; sodium abietate; alkyl sulphates, which include but are not limited to sodium lauryl sulphate and sodium cetyl sulphate; sodium dodecylbenzenesulphonate or sodium dioctyl sulphosuccinate; or fatty acids (e.g. coconut oil);

(c) cationic surfactants, such as water-soluble quaternary ammonium salts of formula N$^+$R'R"R'''R''''Y$^-$, in which the R radicals are identical or different optionally hydroxylated hydrocarbon radicals and Y$^-$ is an anion of a strong acid, such as halide, sulphate and sulphonate anions; cetyltrimethylammonium bromide is one of the cationic surfactants which can be used;

(d) amine salts of formula N$^+$HR'R"R''', in which the R radicals are identical or different optionally hydroxylated hydrocarbon radicals; octadecylamine hydrochloride is one of the cationic surfactants which can be used;

(e) non-ionic surfactants, such as optionally polyoxyethylenated esters of sorbitan, e.g. Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;

(f) amphoteric surfactants, such as substituted lauryl compounds of betaine;

(g) a mixture of at least two of the compounds listed in (a)-(f) above; or (h) an organic solvent or mixture of solvents which inhibit the formation of crystals or amorphous solid after the formulation is administered.

In one embodiment of the crystallization inhibitor, a crystallization inhibitor pair will be used.

Such pairs include, for example, the combination of a film-forming agent of polymeric type and of a surface-active agent. These agents will be selected from the compounds mentioned above as crystallization inhibitor.

In some embodiments, the organic solvent(s) may have a dielectric constant of between about 10 and about 35 or between about 20 and about 30. In other embodiments, the organic solvent may have a dielectric constant of between about 10 and about 40 or between about 20 and about 30. The content of this organic solvent or mixture of solvents in the overall composition is not limited and will be present in an amount sufficient to dissolve the desired components to a desired concentration. As discussed above, the organic solvent may also function as a crystallization inhibitor in the formulation.

In some embodiments, one or more of the organic solvent(s) may have a boiling point of below about 100° C., or below about 80° C. In other embodiments, the organic solvent(s) may have a boiling point of below about 300° C., below about 250° C., below about 230° C., below about 210° C. or below about 200° C.

In some embodiments where there is a mixture of solvents, i.e. a solvent and a co-solvent, the solvents may be present in the composition in a weight/weight (W/W) ratio of about 1/50 to about 1/1. Typically the solvents will be in a ratio of about 1/30 to about 1/1, about 1/20 to about 1/1, or about 1/15 to about 1/1 by weight. Preferably, the two solvents will be present in a weight/weight ratio of about 1/15 to about 1/2. In some embodiments, at least one of the solvents present may act as to improve solubility of the active agent or as a drying promoter. In particular embodiments, at least one of the solvents will be miscible with water.

The formulation may also comprise an antioxidizing agent intended to inhibit oxidation in air, this agent may be present in a proportion of about 0.005 to about 1% (w/v), about 0.01 to about 0.1%, or about 0.01 to about 0.05%.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants; in another embodiment of the surface active agents, the agent is a polyoxyethylenated esters of sorbitan and in yet another embodiment of the surface-active agent, the agents include the various grades of polysorbate, for example Polysorbate 80.

In another embodiment of the invention, the film-forming agent and the surface-active agent may be incorporated in similar or identical amounts within the limit of the total amounts of crystallization inhibitor mentioned elsewhere.

The crystallization inhibitor inhibits the formation of crystals on the coat, and improves the maintenance of the cosmetic appearance of the skin or fur; that is to say without a tendency towards sticking or towards a sticky appearance, despite the high concentration of active material. Substances other than those mentioned herein may be used as crystallization inhibitors in the present invention. In one embodiment, the effectiveness of the crystallization inhibitor may be demonstrated by a test according to which 0.3 mL of a solution comprising 10% (w/v) of the active agent in an appropriate solvent as defined above, and 10% (w/v) of the compound acting as a crystallization inhibitor are placed on a glass slide at 20° C. for 24 hours, after which fewer than 10 crystals, preferably 0 crystals, are seen with the naked eye on the glass slide.

In one embodiment of the antioxidizing agents, the agents are those conventional in the art and include but are not limited to butylated hydroxyanisole, butylated hydroxytoluene, ascorbic acid, sodium metabisulphite, propyl gallate, sodium thiosulphate or a mixture of at least two compounds with antioxidant properties.

The formulation adjuvants discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients or adjuvants are added.

The volume of the formulation applied will depend on the type of animal and the size of the animal as well as the strength of the formulation and the potency of the active agents. In one embodiment, an amount of about 0.1 to about 20 ml of the formulation may be applied to the animal. In other embodiment for the volume, the volume may be about 0.1 to about 10 ml, about 0.1 to about 5 ml, about 0.5 ml to about 10 ml, or about 0.3 to about 3 ml.

In another embodiment of the invention, application of a spot-on formulation according to the present invention may also provide long-lasting and broad-spectrum efficacy when the solution is applied to the mammal or bird. The spot-on formulations provide for topical administration of a concentrated solution, suspension, microemulsion or emulsion for intermittent application to a spot on the animal, generally between the two shoulders (solution of spot-on type).

For spot-on formulations, the carrier may be a liquid carrier vehicle as described in U.S. Pat. No. 6,426,333 (incorporated herein by reference), which in one embodiment of the spot-on formulation may comprise a solvent or mixture of solvents including, but not limited to, acetone, an aliphatic alcohol such as methanol, ethanol, propanol, butanol, isopropanol, pentanol, hexanol, heptanol, octanol, nonanol, cyclopentanol, cyclohexanol, ethylene glycol, propylene glycol and the like; an aromatic alcohol such as phenol, cresol, naphthol, benzyl alcohol and the like; acetonitrile, butyl diglycol, an organic amide such as dimethylacetamide, dimethylformamide, monomethylacetamide, 2-pyrrolidone, N-methylpyrrolidone, vinylpyrrolidone and the like; dimethylsulfoxide (DMSO), a glycol polymer or an ether thereof, such as polyethylene glycol (PEG) of various grades, polypropylene glycols of various grades, dipropylene glycol n-butyl ether, ethylene glycol monoethyl ether, ethylene glycol monomethyl ether, dipropylene glycol monomethyl ether, diethylene glycol monoethyl ether, ethylene glycol, diethyl phthalate fatty acid esters, such as the diethyl ester or diisobutyl adipate, or a mixture of at least two of these solvents.

The liquid carrier vehicle may optionally contain a crystallization inhibitor including, but not limited to, those described in (a) to (h) above, or a compound that may act both as a solvent and a crystallization inhibitor (as defined above), or a mixture of these crystallization inhibitors.

Spot-on formulations may be prepared by dissolving the active ingredients into the pharmaceutically or veterinary acceptable vehicle. Alternatively, the spot-on formulation may be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host.

Dosage forms may typically contain from about 0.1 mg to about 5 g. In other embodiments, the dosage form may contain about 0.5 mg to about 5 g of an active agent. In one embodiment of the dosage form, the dosage may contain from about 1 mg to about 500 mg of an active agent, typically about 25 mg, about 50 mg, about 100 mg, about 200 mg, about 300 mg, about 400 mg, about 500 mg, about 600 mg, about 800 mg, or about 1000 mg.

In one embodiment of the invention, the active agent may be present in the formulation at a concentration of about 0.05 to about 10% weight/volume. In another embodiment of the invention, the active agent may be present in the formulation as a concentration from about 0.1 to about 2% weight/volume. In yet another embodiment of the invention, the active agent may be present in the formulation as a concentration from about 0.25 to about 1.5% weight/volume. In still another embodiment of the invention, the active agent may be present in the formulation as a concentration about 1% weight/volume.

Methods of Treatment:

As discussed above, the compounds of formulae (I) and (II) are effective against endoparasites and may be used to treat and prevent parasitic infestations in animals or humans. In one embodiment, the invention provides a method for treating or preventing an endoparasitic infection in an animal, comprising administering an endoparasitically effective amount of a compound of formula (I) or (II), or veterinarily or pharmaceutically acceptable salts thereof, or a composition comprising the compounds, to the animal.

In still another embodiment of the invention, a method is provided for the treatment or prevention of a parasitic infestation at a locus, which comprises administering or applying a parasiticidally effective amount of a compound of formula (I) or (II), or veterinarily acceptable salts thereof, to the locus. With respect to animal health applications, "locus" is intended to mean a habitat, breeding ground, area, material or environment in which a parasite is growing or may grow, including in or on an animal.

Mammals which can be treated include but are not limited to humans, cats, dogs, cattle, chickens, cows, deer, goats, horses, llamas, pigs, sheep and yaks. In one embodiment of the invention, the mammals treated are humans, cats or dogs.

When an anthelmintic agent is added to the composition of the invention, the composition can also be used to treat against endoparasites such as those helminths selected from the group consisting of *Anaplocephala, Ancylostoma, Anecator, Ascaris, Capillaria, Cooperia, Dipylidium, Dirofilaria, Echinococcus, Enterobius, Fasciola, Haemonchus, Oesophagostumum, Ostertagia, Oxyuris* spp., *Toxocara, Strongyloides, Strongylus* spp., *Toxascaris, Trichinella, Trichuris*, and *Trichostrongylus*. The inventive compounds are particularly effective against organisms from the class of Protozoa, for example, *Eimeria* spp. and *Plasmodia* spp.

In each aspect of the invention, the compounds and compositions of the invention can be applied against a single organism/parasite or combinations thereof.

Additional pharmaceutical, pesticidal or veterinarily active ingredients, which include, but are not limited to, parasiticidals including acaricides, anthelmintics, endectocides and insecticides, may also be added to the compositions of the invention. Anti-parasitic agents may include both ectoparasiticidal and endoparasiticidal agents. Veterinary pharmaceutical agents are well-known in the art (see e.g. *Plumb' Veterinary Drug Handbook*, 5$^{th}$ Edition, ed. Donald C. Plumb, Blackwell Publishing, (2005) or *The Merck Veterinary Manual*, 9$^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitraz, amitriptyline, amlodipine besylate, ammonium chloride, ammonium molybdenate, amoxicillin, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide +/-clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, dichlorvos, diclofenac sodium, dicloxacillin, diethylcarbamazine citrate, diethylstilbestrol (DES), difloxacin, digoxin, dihydrotachysterol (DHT), diltiazem, dimenhydrinate, dimercaproVBAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fenbendazole, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (OXYGLOBIN®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inaminone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morantel tartrate, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxfendazole, oxibutynin chloride, oxymorphone, oxytretracycline, oxytocin, pamidronate disodium, pancreplipase, pancuronium bromide, paromomycin sulfate, parozetine, pencillamine, penicillins including penicillin G and penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenyloin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, praziquantel, prazosin, prednisolone/prednisone, primidone, procainamide, procarbazine, prochlorperazine, propantheline bromide, propionibacterium acnes injection, propofol, propranolol, protamine sulfate, pseudoephedrine, psyllium hydrophilic mucilloid, pyrantel pamoate, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/1-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiabendazole, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocamide, tolazoline, telfenamic acid, topiramate, tramadol, trimcinolone acetonide, trientine, trilostane, trimepraxine tartrate w/prednisolone, tripelenamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, arylpyrazole compounds may be added to the compositions of the invention. Arylpyrazoles may include but are not limited to those described in U.S. Pat. Nos. 6,001,384; 6,010,710; 6,083,519; 6,096,329; 6,174,540; 6,685,954 and 6,998,131, all of which are hereby incorporated by reference in their entirety, each assigned to Merial, Ltd., Duluth, Ga.). A particularly preferred arylpyrazole compound that may be combined with the compounds of the invention is fipronil (5-amino-1-[2,6-dichloro-4-(trifluoromethyl)phenyl]-4-(trifluoromethylsulfinyl)pyrazole-3-carbonitrile, CAS No. 120068-37-3).

In another embodiment of the invention, nodulisporic acid and its derivatives (a class of known acaricidal, anthelmintic, anti-parasitic and insecticidal agents) may be added to the compositions of the invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety. The compositions may include one or more of the known nodulisporic acid derivatives in the art, including all stereoisomers, such as those described in the literature cited above.

In another embodiment, anthelmintic compounds of the amino acetonitrile class (AAD) of compounds such as monepantel (ZOLVIX) and the like may be added to the compositions of the invention. These compounds are described, for example, in WO 2004/024704; Sager et al., Veterinary Parasitology, 2009, 159, 49-54; Kaminsky et al., Nature vol. 452, 13 Mar. 2008, 176-181.

The compositions of the invention may also be combined with paraherquamide compounds and derivatives of these compounds, including derquantel (see Ostlind et al., *Research in Veterinary Science,* 1990, 48, 260-61; and Ostlind et al., *Medical and Veterinary Entomology,* 1997, 11, 407-408). The paraherquamide family of compounds are known class of compounds that include a spirodioxepino indole core with activity against certain parasites (see *Tet. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and Tet. Lett. 1981, 22, 1977). Further references to the paraherquamide derivatives can be found, for example, in WO 91/09961, WO 92/22555, WO 97/03988, WO 01/076370, WO 09/004,432, U.S. Pat. No. 5,703,078 and U.S. Pat. No. 5,750,695, all of which are hereby incorporated by reference in their entirety.

In another embodiment, the compositions of the invention may be combined with cyclo-depsipeptide anthelmintic compounds including emodepside (see Willson et al., Parasitology, January 2003, 126(Pt 1):79-86).

In another embodiment of the invention, the class of acaricides or insecticides known as insect growth regulators (IGRs) may also be added to the compositions of the invention. Compounds belonging to this group are well known to the practitioner and represent a wide range of different chemical classes. These compounds all act by interfering with the development or growth of the insect pests. Insect growth regulators are described, for example, in U.S. Pat. No. 3,748,356; U.S. Pat. No. 3,818,047; U.S. Pat. No. 4,225,598; U.S. Pat. No. 4,798,837; U.S. Pat. No. 4,751,225; EP 0 179 022 or GB 2 140 010 as well as U.S. Pat. Nos. 6,096,329 and 6,685,954, all of which are hereby incorporated by reference in their entirety. Examples of IGRs suitable for use may include but are not limited to methoprene, pyriproxyfen, hydroprene, cyromazine, fluazuron, lufenuron, novaluron, pyrethroids, formamidines and 1-(2,6-difluorobenzoyl)-3-(2-fluoro-4-(trifluoromethyl)phenylurea.

An anthelmintic agent that may be combined with the compositions of the invention may be a benzenedisulfonamide compound, which includes but is not limited to clorsulon; or a cestodal agent, which includes but is not limited to praziquantel, pyrantel or morantel.

In some embodiments, a parasiticidal agent that may be combined with the compositions of the invention may be a biologically active peptide or protein including, but not limited to, depsipeptides, which act at the neuromuscular junction by stimulating presynaptic receptors belonging to the secretin receptor family resulting in the paralysis and death of parasites. In one embodiment of the depsipeptide, the depsipeptide may be emodepside.

In other embodiments, an insecticidal agent that may be combined with the compositions of the invention may be a spinosyn (e.g. spinosad) or a substituted pyridylmethyl derivative compound such as imidacloprid. Agents of this class are described above, and for example, in U.S. Pat. No. 4,742,060 or in EP 0 892 060, both of which are hereby incorporated by reference in their entirety.

For endoparasites, parasiticides which may be combined include but are not limited to pyrantel, morantel, the benzimidazoles (including albendazole, cambendazole, thiabendazole, fenbendazole, febantel, oxfendazole, oxibendazole, triclabendazole, mebendazole and netobimin), levamisole, closantel, rafoxanide, nitroxynil, disophenol and paraherquamide. For ectoparasites, insecticides which may be combined also include but are not limited to pyrethoids, organophosphates and neonicotinoids such as imidacloprid, as well as compounds such as metaflumizone, amitraz and ryanodine receptor antagonists.

The compositions of the invention may also comprise an antiparasitic macrocyclic lactone compound in combination with the active compound of the invention. The macrocyclic lactones include, but are not limited to, avermectins, such as abamectin, dimadectin, doramectin, eprinomectin, ivermectin, latidectin, lepimectin, selamectin, ML-1,694, 554 and milbemycins, such as milbemectin, milbemycin D, moxidectin and nemadectin. Also included are the 5-oxo and 5-oxime derivatives of said avermectins and milbemycins. Examples of compositions comprising macrocyclic lactones include but are not limited to those described in U.S. Pat. Nos. 6,426,333; 6,482,425; 6,962,713 and 6,998,131, all of which are incorporated by reference in their entirety; —each assigned to Merial, Ltd., Duluth, Ga.

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M.H. Fischer and H. Mrozik, William C. Campbell, published by Springer Verlag., or Albers-Schönberg et al. (1981), "Avermectins Structure Determination", J. Am. Chem. Soc., 103, 4216-4221. For doramectin, "Veterinary Parasitology", vol. 49, No. 1, Jul. 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, *Tetrahedron Lett.*, 24, 5333-5336, U.S. Pat. No. 4,134,973 and EP 0 677 054.

Macrocyclic lactones are either natural products or are semi-synthetic derivatives thereof. The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. patent No. 4,199,569, each of which is incorporated herein by reference. Mention is also made of U.S. Pat. Nos. 4,468,390, 5,824,653, EP 0 007 812 A1, U.K. Patent Specification 1 390 336, EP 0 002 916, and New Zealand Patent No. 237 086, inter alia, all of which are incorporated by reference in their entirety. Naturally occurring milbemycins are described in U.S. Pat. No. 3,950,360 as well as in the various references cited in "The Merck Index" 12$^{th}$ ed., S. Budavari, Ed., Merck & Co., Inc. Whitehouse Station, N.J. (1996). Latidectin is described in the "International Nonproprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054, all of which are incorporated by reference in their entirety.

In yet another embodiment of the invention, adulticide insecticides and acaricides can also be added to the composition of the invention. These include pyrethrins (which include cinerin I, cinerin II, jasmolin I, jasmolin II, pyrethrin I, pyrethrin II and mixtures thereof) and pyrethroids, organophosphate (which included but are not limited to chlorfenvinphos, crotoxyphos, dichlorvos, heptenophos, mevinphos, monocrotophos, naled, TEPP, tetrachlorvinphos) and carbamates (which include but are not limited to benomyl, carbanolate, carbaryl, carbofuran, meththiocarb, metolcarb, promacyl, propoxur, aldicarb, butocarboxim, oxamyl, thiocarboxime and thiofanox).

In addition to the other active agents mentioned above, combinations of two or more active agents may be used with the compounds of the invention in a composition to treat a desired spectrum of pests and parasites. It would be well within the skill level of the practitioner to decide which individual compound can be used in the inventive formulation to treat a particular infection of an insect.

The invention will now be further described by way of the following non-limiting examples.

EXAMPLES

The following examples are provided to illustrate certain embodiments of the invention and are not to be construed in any way as limiting the scope of the invention.

Example 1

Solubility of Monensin in Various Solvents

TABLE 1 solubility of monensin sodium salt in various solvents

| Solvent | Solubility (mg/mL) | Solubility |
|---|---|---|
| H$_2$O | 3.3 | -- |
| Acetone | 15.1 | + |
| Acetonitrile | 7.0 | - |

TABLE 1-continued solubility of monensin sodium salt in various solvents

| Solvent | Solubility (mg/mL) | Solubility |
|---|---|---|
| Methanol | 20 | + + + |
| Ethyl acetate | 11.9 | + |
| Chloroform | 20 | + + + |
| Toluene | 20 | + + + |
| DMSO | 1.1 | - - - |
| THF | 20 | + + + |
| DMF | 18.7 | + + |

Monensin sodium salt (200 g) was mixed with 10 mL of solvent. The solution was stirred for 2 hours and then filtered through sintered glass. The precipitate was then dried and weighed. The difference between the weight of the product initially introduced and the one remaining on the sintered disk after filtration indicated the solubility of the product at ambient temperature in a 10 mL volume. The results are presented in Table 1.

Example 2

Synthesis of Inventive Compounds

Due to their increased lipophilicity, the polyether ionophores have the ability to complex and transfer the cations across the cell membrane. In fact, they have the ability to capture a sodium atom due to electrostatic interactions between the cation and the six oxygen atoms and due to the formation of hydrogen bonds between the carboxylic acid and the two terminal hydroxyl groups. The perfect match between the sodium atom size and that of the receptor cavity can be explained by the closing of the ring due to the formation of these hydrogen bonds. The absence of hydrogen bonds leads to the loss in polyether activity.

Therefore, in order to preserve and strengthen said hydrogen bonds, amidations of the carboxylic acid with amines containing carboxylic acid, whether shielded or not under ester form were performed.

The compounds described below were prepared according to the general synthetic processes described. It will be apparent to those skilled in the art that other compounds of formulae (I) and (II) may be prepared using similar methods by adapting the reagents and conditions to achieve the desired products.

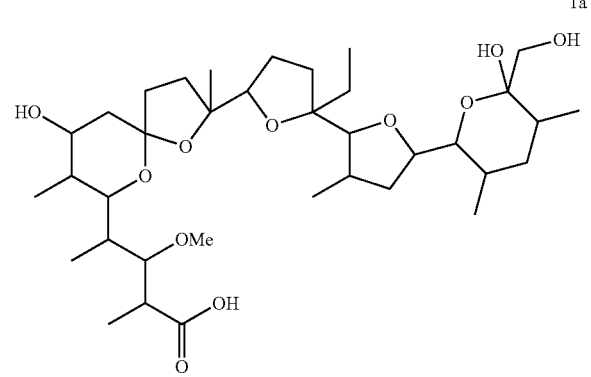

1a

Monensin—the monensin sodium (20.0 g, 29 mmol) was dissolved in methanol (200 mL). Monensin was, then, precipitated by adding slowly water (120 mL) to the methanol solution. The reaction mixture was stirred during 15 minutes. The white salt obtained was dried under vacuum. It was then dissolved in chloroform (100 mL) and stirred vigorously for 1 h at room temperature with a layer of aqueous perchloric acid (1M) to convert the sodium salt into the acid form of monensin. The chloroform layer was washed with distilled water until the washings were neutral, and then evaporated to dryness. The obtained powder (20 g, 100%) was dried under vacuum stored at −20° C.

Compound (3a)—1-benzylamidomonensine

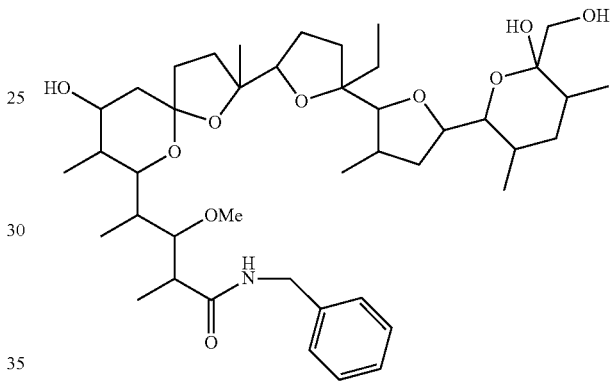

3a

NMR $^1$H (400 MHz, CDCl$_3$) ppm: 7.24 (5H, m), 4.91 (1H, s), 4.58 (1H, s), 4.46-4.34 (2H, m), 4.27 (1H, m), 4.12 (1H, dd, J1=7.8 Hz, J2=2 Hz), 3.91 (1H, d, J=4.28 Hz), 3.86 (1H, dd, J1=9.56 Hz, J2=2.76 Hz), 3.70 (1H, s), 3.50 (1H, m), 3.39-3.35 (5H, m), 2.51 (1H, m), 2.24-2.01 (3H, m), 2.00-1.85 (3H, m), 1.82-1.60 (8H, m), 1.53-1.34 (11H, m), 1.22 (3H, d, J=6.8 Hz), 0.99 (3H, d, J=6.8 Hz), 0.91-0.76 (15H, m).

NMR $^{13}$C (400 MHz, CDCl$_3$) ppm: 176.20, 139.26, 128.57, 128.54, 127.69, 127.06, 107.90, 97.64, 86.57, 86.08, 85.51, 83.24, 82.46, 76.69, 74.97, 71.25, 67.67, 67.43, 58.93, 49.24, 43.25, 42.45, 39.00, 37.47, 36.93, 36.69, 35.08, 34.75, 34.51, 33.37, 33.12, 32.76, 31.13, 30.30, 27.68, 26.65, 17.35, 16.35, 15.52, 14.05, 12.93, 11.00, 8.36.

Exact mass: HR ESIMS: Calculated for $C_{43}H_{69}O_{10}NNa^+$= 782.4819. found=782.4820.

A mixture of monensin acid (500 mg, 0.75 mmol, 1 eq) and HOBt (127 mg, 0.90 mmol, 1.2 eq) in THF (5 mL) was stirred at 5° C. for 30 min and then DCC (186.7 mg, 0.90 mmol, 1.2 eq) was added. After being stirred for 1 h, the reaction mixture was treated with benzylamine (110 μL, 0.98 mmol, 1.3 eq), and stirring was maintained at room temperature during 4 days. The mixture was evaporated to dryness to give a powder, which was suspended in EtOAc (6 mL) and filtered off. The organic phase was washed with 10% citric acid solution (3 mL), saturated NaHCO$_3$ (3 mL) and distilled water (3 mL), successively, dried over MgSO$_4$ and evaporated to dryness to afford 417.5 mg (73%) of the desired amide.

Compound (3b)—1-(4-methylbenzoate)methylene Amidomonensine

Compound (3c)—1-(3-methylbenzoate)methylene Amidomonensin

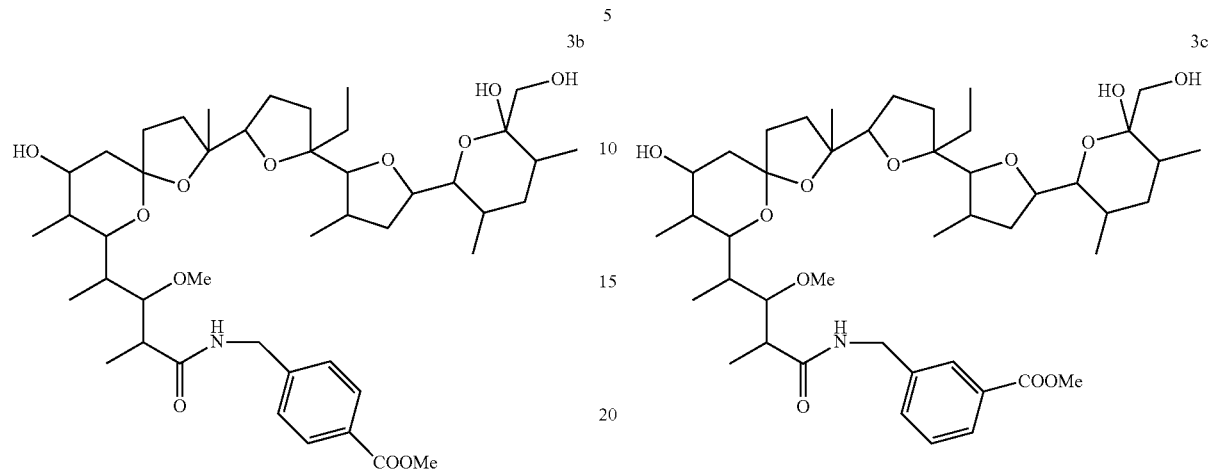

NMR $^1$H (300 MHz, CDCl$_3$) ppm: 7.97 (2H, d, J=8.46 Hz), 7.36 (2H, d, J=8.46 Hz), 4.47 (2H, d, J=5.85 Hz), 4.30 (1H, m), 4.17 (1H, dd, J1=2.07 Hz, J2=7.71 Hz), 3.91 (5H, m), 3.74 (1H, d, J=2.82 Hz), 3.40 (1H, q), 3.39 (6H, m), 2.56 (1H, m), 2.23 (2H, m), 2.04-1.35 (24H, m), 1.26 (5H, m), 1.15 (1H, m), 1.02 (3H, d, J=6.96 Hz), 0.91 (6H, m), 0.83-0.75 (8H, m).

NMR $^1$H (400 MHz, CDCl$_3$) ppm: 7.95 (2H, d, J=8.32 Hz), 7.52 (1H, t, J=5.76 Hz), 7.35 (2H, d, J=8.32 Hz), 4.67 (1H, m), 4.47 (2H, qd, J1=6.32 Hz, J2=15.60 Hz), 4.30 (1H, m), 4.13 (1H, m), 3.96 (1H, d, J=4.28 Hz), 3.90 (5H, m), 3.72 (1H, s), 3.50 (1H, q), 3.39 (6H, m), 2.99 (1H, s), 2.53 (1H, m), 2.25-2.16 (2H, m), 2.13-2.05 (1H, m), 2.04-1.87 (3H, m), 1.86-1.83 (1H, d, J=10.32 Hz), 1.74-1.24 (20H, m), 1.01 (3H, d, J=7.08 Hz), 0.92 (6H, m), 0.83-0.72 (9H, m).

NMR $^{13}$C (400 MHz, CDCl$_3$) ppm: 176.66, 167.18, 144.87, 129.88, 128.83, 127.42, 107.94, 97.85, 86.35, 86.06, 85.39, 83.16, 82.16, 74.53, 71.14, 67.65, 67.37, 59.01, 52.13, 42.90, 42.31, 38.96, 37.57, 36.98, 36.63, 35.08, 34.59, 34.48, 34.07, 33.33, 33.29, 32.73, 31.18, 30.50, 27.63, 26.95, 17.32, 16.41, 15.47, 14.35, 12.92, 10.93, 8.43.

Exact mass: HR ESIMS: Calculated for $C_{45}H_{71}O_{12}NNa^+$= 840.4874. found=840.4873.

A mixture of monensin acid (500 mg, 0.75 mmol, 1 eq) and HOBt (127 mg, 0.90 mmol, 1.2 eq) in THF (4 mL) was stirred at 5° C. for 30 min and then DCC (187.5 mg, 0.90 mmol, 1.2 eq) was added. After being stirred for 1 h, the reaction mixture was treated with a solution of methyl 4-(aminomethyl)benzoate hydrochloride (198.6 mg, 0.98 mmol, 1.3 eq) and N-methylmorpholine (110 µL, 0.98 mmol, 1.3 eq) in THF (1 mL), and stirring was maintained at room temperature during 4 days. The mixture was evaporated to dryness to give a powder, which was suspended in EtOAc (6 mL) and filtered off. The organic phase was washed with 10% citric acid solution (3 mL), saturated NaHCO$_3$ (3 mL) and distilled water (3 mL), successively, dried over MgSO$_4$ and evaporated to dryness to afford 585.9 mg (93%) of the desired amide.

NMR $^1$H (400 MHz, CDCl$_3$) ppm: 7.94 (1H, s), 7.89 (1H, d, J=7.80 Hz), 7.49 (1H, d, J=7.80 Hz), 7.38-7.33 (2H, m), 5.08 (1H, s), 4.63 (1H, d, J=7.52 Hz), 4.51-4.40 (2H, m), 4.30 (1H, m), 4.15 (1H, dd, J1=2 Hz, J2=7.80 Hz), 3.92-3.88 (6H, m), 3.71 (1H, s), 3.52 (1H, dd, J1=5.56 Hz, J2=10.08 Hz), 3.40-3.35 (6H, m), 2.56-2.53 (1H, m), 2.24-2.21 (2H, m), 2.03-1.97 (1H, m), 1.96-1.87 (3H, m), 1.84-1.64 (6H, m), 1.61-1.55 (1H, m), 1.54-1.35 (11H, m), 1.25 (3H, d, J=7.04 Hz), 1.01 (3H, d, J=6.80 Hz), 0.92-0.89 (6H, m), 0.83-0.75 (9H, m).

NMR $^{13}$C (400 MHz, CDCl$_3$) ppm: 176.50, 167.15, 139.83, 132.27, 130.39, 128.66, 128.37, 107.91, 97.64, 86.52, 85.97, 85.60, 83.22, 82.40, 76.62, 74.94, 71.25, 67.63, 67.50, 58.96, 52.17, 42.86, 42.38, 38.96, 37.50, 36.98, 36.60, 35.12, 34.70, 34.45, 33.36, 33.17, 32.70, 31.10, 30.44, 27.69, 26.77, 17.33, 16.31, 15.47, 14.11, 12.92, 10.95, 8.38.

Exact mass: HR ESIMS: Calculated for $C_{45}H_{71}O_{12}NNa^+$= 840.4874. found=840.4873.

A mixture of monensin acid (507.9 mg, 0.75 mmol, 1 eq) and HOBt (124.3 mg, 0.90 mmol, 1.2 eq) in THF (3 mL) was stirred at 5° C. for 30 min and then DCC (190.4 mg, 0.90 mmol, 1.2 eq) was added. After being stirred for 1 h, the reaction mixture was treated with a solution of methyl 3-(aminomethyl)benzoate hydrochloride (199.4 mg, 0.98 mmol, 1.3 eq) and N-methylmorpholine (110 µL, 0.98 mmol, 1.3 eq) in THF (2 mL), and stirring was maintained at room temperature during 3 days. The mixture was evaporated to dryness to give a powder, which was suspended in EtOAc (6 mL) and filtered off. The organic phase was washed with 10% citric acid solution (3 mL), saturated NaHCO$_3$ (3 mL) and distilled water (3 mL), successively, dried over MgSO$_4$ and evaporated to dryness to afford 549.2 mg (90%) of the desired amide.

Compound (4a)-(R)-methyl 2'-(monensinamido)-3'-(1'H-indol-3'-yl)propanoate

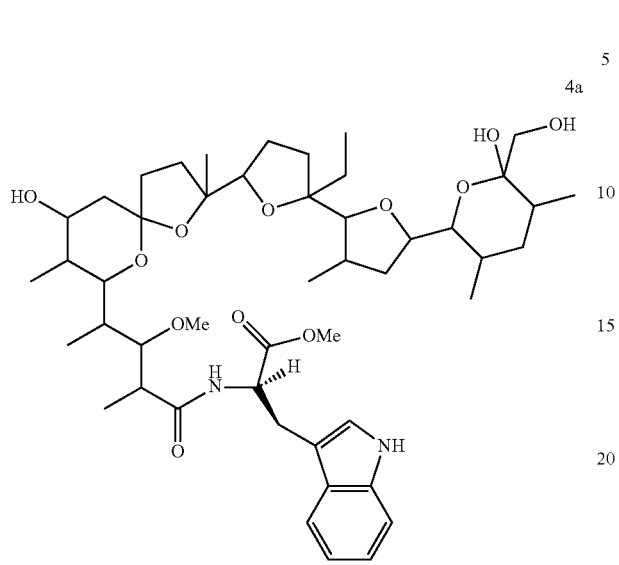

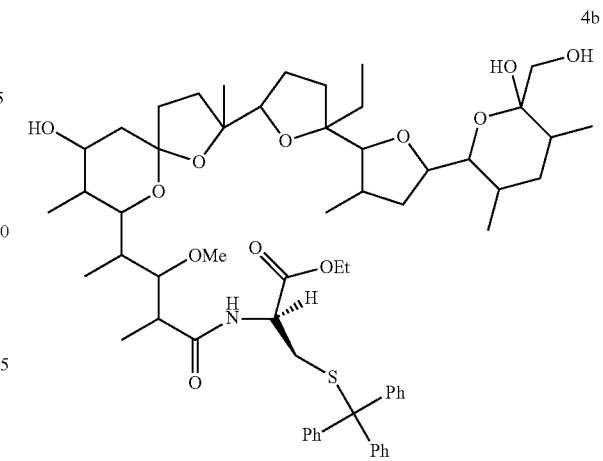

NMR $^1$H (400 MHz, CDCl$_3$) ppm: 9.11 (1H, s), 7.49 (1H, d, J=7.92 Hz), 7.39 (1H, d, J=8.04 Hz), 7.14 (1H, td, J1=1.00 Hz, J2=7.08 Hz), 7.07 (2H, m), 6.80 (1H, d, J=7.44 Hz), 4.83 (1H, m), 4.55 (1H, d, J=9.44 Hz), 4.3 (1H, m), 4.05 (1H, dd, J1=2.40 Hz, J2=6.80 Hz), 3.95 (1H, d, J=4.64 Hz), 3.89 (1H, d, J1=3.04 Hz, J2=10.08 Hz), 3.65 (3H, m), 3.55 (3H, m), 3.35 (2H, dd, J1=5.16 Hz, J2=14.72 Hz), 3.28 (1H, d, J=5.4 Hz), 3.23 (3H, m), 2.69 (1H, m), 2.53 (1H, m), 2.29 (1H, m), 2.16 (2H, m), 1.90 (3H, m), 1.79-1.58 (7H, m), 1.57-1.28 (11H, m), 1.15 (3H, m), 0.98-0.85 (16H, m), 0.56 (3H, d, J=7.04 Hz).

NMR $^{13}$C (400 MHz, CDCl$_3$) ppm: 175.00, 172.69, 136.51, 127.61, 123.59, 122.01, 119.35, 118.67, 111.50, 109.57, 107.83, 97.65, 86.55, 86.39, 85.61, 84.50, 83.56, 83.39, 75.51, 71.35, 67.42, 67.24, 57.78, 52.38, 49.28, 41.75, 38.97, 37.36, 37.11, 36.94, 34.94, 34.38, 34.09, 33.39, 32.93, 31.30, 30.10, 27.86, 27.58, 26.73, 25.75, 25.08, 17.51, 15.80, 13.41, 12.44, 10.90, 8.34.

Exact mass: HR ESIMS: Calculated for C$_{48}$H$_{74}$O$_{12}$N$_2$Na$^+$= 893.5139. found=893.5140.

A mixture of monensin acid (200 mg, 0.30 mmol, 1 eq) and HOBt (49.2 mg, 0.36 mmol, 1.2 eq) in THF (2 mL) was stirred at 5° C. for 30 min and then DCC (74.2 mg, 0.36 mmol, 1.2 eq) was added. After being stirred for 1 h, the reaction mixture was treated with a solution of methyl-2-amino-3-(1H-indol-3-yl)propanoate hydrochloride (99.8 mg, 0.39 mmol, 1.3 eq) and N-methylmorpholine (45 μL, 0.39 mmol, 1.3 eq) in THF (1 mL), and stirring was maintained at room temperature during 4 days. The mixture was evaporated to dryness to give a powder, which was suspended in EtOAc (6 mL) and filtered off. The organic phase was washed with 10% citric acid solution (3 mL), saturated NaHCO$_3$ (3 mL) and distilled water (3 mL), successively, dried over MgSO$_4$ and evaporated to dryness to afford 247.3 mg (95%) of the desired amide. Compound (4b)-(S)-ethyl 2'-(monensinamido)-3'-(tritylthio)propanoate NMR $^1$H (400 MHz, CDCl$_3$) ppm: 7.43-7.35 (6H, m), 7.37-7.18 (9H, m), 4.55-4.50 (1H, m), 4.29-4.24 (1H, m), 4.17-4.11 (2H, m), 4.10-4.05 (1H, m), 3.86 (1H, d, J=4.52 Hz), 3.83-3.75 (1H, m), 3.73-3.65 (1H, m), 3.64-3.57 (1H, m), 3.50-3.47 (3H, m), 3.39-3.36 (3H, m), 2.69 (1H, dd, J1=5.04 Hz, J2=12.08 Hz), 2.58-2.50 (2H, m), 2.35-2.21 (1H, m), 2.19-2.03 (4H, m), 1.99-1.89 (4H, m), 1.87-1.63 (6H, m), 1.62-1.32 (9H, m), 1.28-1.19 (6H, m), 1.04-0.81 (18H, m).

NMR $^{13}$C (400 MHz, CDCl$_3$) ppm: 174.36, 170.23, 147.00, 144.49, 129.88, 128.35, 127.17, 107.70, 97.55, 89.58, 86.95, 86.05, 83.78, 82.01, 77.63, 76.94, 71.61, 68.51, 67.76, 61.96, 58.50, 51.67, 42.65, 39.52, 37.22, 37.09, 36.66, 35.45, 34.92, 34.22, 33.97, 33.23, 32.65, 31.38, 30.02, 28.27, 25.90, 21.48, 17.75, 16.60, 16.05, 14.51, 13.53, 13.04, 11.44, 8.45.

Exact mass: HR ESIMS: Calculated for C$_{60}$H$_{85}$O$_{12}$N$_S$Na$^+$= 1066.5690. found=1066.5691.

A mixture of monensin acid (200 mg, 0.30 mmol, 1 eq) and HOBt (49.0 mg, 0.36 mmol, 1.2 eq) in THF (2 mL) was stirred at 5° C. for 30 min and then DCC (75.9 mg, 0.36 mmol, 1.2 eq) was added. After being stirred for 1 h, the reaction mixture was treated with a solution of trytilated cysteine ethanoate hydrochloride (116.4 mg, 0.27 mmol, 0.91 eq) and N-methylmorpholine (45 μL, 0.39 mmol, 1.3 eq) in THF (1.5 mL), and stirring was maintained at room temperature during 2 days. The mixture was evaporated to dryness to give a powder, which was suspended in EtOAc (6 mL) and filtered off. The organic phase was washed with 10% citric acid solution (3 mL), saturated NaHCO$_3$ (3 mL) and distilled water (3 mL), successively, dried over MgSO$_4$ and evaporated to dryness to afford 204.8 mg (67%) of the desired amide.

Compound (4c)—Methyl 2'-(monensinamido)-2'-(4'-fluorophenyl)acetate

Compound (4d)—(S)-methyl 2'-monensinamido-3'-(tritylthio)propanoate

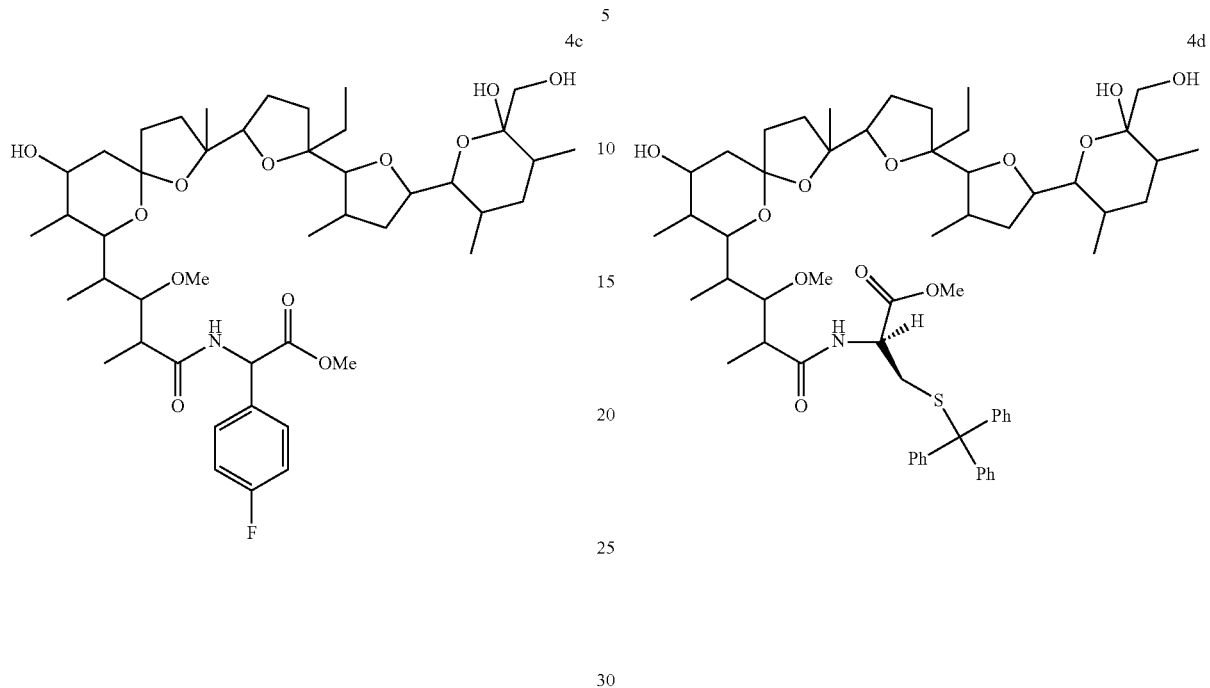

NMR $^1$H (400 MHz, CDCl$_3$) ppm: 8.62-8.58 (1H, m), 7.40-7.31 (2H, m), 7.08-7.00 (2H, td, J1=2.24 Hz, J2=8.8 Hz), 5.55 (1H, dd, J1=7.56 Hz, J2=43.80 Hz), 4.31-4.26 (1H, m), 4.18-4.10 (1H, m), 3.92 (1H, d, J=4.52 Hz), 3.89-3.75 (2H, m), 3.70 (3H, s), 3.69-3.49 (2H, m), 3.45-3.37 (4H, m), 3.29 (1H, m), 2.60-2.57 (1H, m), 2.27-2.20 (1H, m), 2.18-1.62 (12H, m), 1.55-1.30 (8H, m), 1.28-1.18 (3H, m), 1.03-0.73 (21H, m).

NMR $^{13}$C (400 MHz, CDCl$_3$) ppm: 175.05, 171.18, 163.66, 161.25, 129.66 (t, J=8 Hz), 116.15 (dd, J1=4 Hz, J2=22 Hz), 107.58, 97.39, 86.83, 86.32, 85.81, 83.62, 82.59, 76.86, 75.88, 71.69, 68.23, 67.56, 59.20, 58.80, 56.03 (d, J=65.2 Hz), 42.91, 39.40, 37.35, 37.23, 37.00, 35.23, 34.92, 33.75, 33.13, 33.09, 31.33, 30.27, 28.08, 26.30, 17.72, 16.72, 15.96, 14.28, 13.08, 11.46, 11.23, 8.60.

Exact mass: HR ESIMS: Calculated for $C_{45}H_{70}O_{12}NFNa^+$= 858.4780. found=858.4781.

A mixture of monensin acid (370 mg, 0.55 mmol, 1 eq) and HOBt (89.9 mg, 0.66 mmol, 1.2 eq) in THF (3.7 mL) was stirred at 5° C. for 30 min and then DCC (136.8 mg, 0.66 mmol, 1.2 eq) was added. After being stirred for 1 h, the reaction mixture was treated with 4-Fluoro-DL-alpha-phenylglycine methanoate (133.1 mg, 0.72 mmol, 1.3 eq) and stirring was maintained at room temperature during 4 days. The mixture was evaporated to dryness to give a powder, which was suspended in EtOAc (6 mL) and filtered off. The organic phase was washed with 10% citric acid solution (3 mL), saturated NaHCO$_3$ (3 mL) and distilled water (3 mL), successively, dried over MgSO$_4$ and evaporated to dryness to afford 433.9 mg (94%) of the desired amide.

NMR $^1$H (400 MHz, CDCl$_3$) ppm: 7.45-7.20 (15H, m), 6.86 (1H, d, J=7.56 Hz), 4.53 (1H, q, J=6.38 Hz), 4.27 (1H, m), 4.07 (1H, dd, J1=2.04 Hz, J2=8.56 Hz), 3.91 (1H, d, J=4.52 Hz), 3.84-3.80 (1H, m), 3.75-3.65 (5H, m), 3.60-3.56 (1H, m), 3.50-3.44 (4H, m), 3.36 (3H, s), 2.70 (1H, dd, J1=4.76 Hz, J2=12.08 Hz), 2.56-2.48 (2H, m), 2.27 (1H, m), 2.14 (2H, m), 2.00-1.63 (10H, m), 1.60-1.30 (10H, m), 1.27-1.19 (2H, m), 1.01-0.83 (21H, m).

NMR $^{13}$C (400 MHz, CDCl$_3$) ppm: 175.47, 171.10, 144.52, 129.61, 128.07, 126.90, 107.72, 97.34, 87.20, 86.48, 85.54, 83.39, 81.93, 76.80, 75.84, 71.30, 68.06, 67.33, 66.66, 58.35, 52.55, 51.33, 42.34, 39.19, 36.93, 36.55, 35.06, 34.97, 34.64, 34.06, 33.83, 33.57, 32.97, 32.58, 31.15, 27.91, 25.83, 25.08, 23.75, 17.47, 16.38, 15.77, 13.38, 12.81, 11.15, 8.23.

Exact mass: HR ESIMS: Calculated for $C_{59}H_{83}O_{12}NSNa^+$= 1052.5534. found=1052.5535.

A mixture of monensin acid (1.01 g, 1.49 mmol, 1 eq) and HOBt (242.3 mg, 1.79 mmol, 1.2 eq) in THF (8 mL) was stirred at 5° C. for 30 min and then DCC (376.8 mg, 1.79 mmol, 1.2 eq) was added. After being stirred for 1 h, the reaction mixture was treated with a solution of trytilated cysteine methanoate hydrochloride (807.3 mg, 1.95 mmol, 1.3 eq) and N-methylmorpholine (215 µL, 1.95 mmol, 1.3 eq) in THF (2 mL), and stirring was maintained at room temperature during 3 days. The mixture was evaporated to dryness to give a powder, which was suspended in EtOAc (12 mL) and filtered off. The organic phase was washed with 10% citric acid solution (7 mL), saturated NaHCO$_3$ (7 mL) and distilled water (7 mL), successively, dried over MgSO$_4$ and evaporated to dryness to afford 1.44 g (93%) of the desired amide.

Compound (5)-1-trifluoroethanamidomonensine

Compound (6a)-1-(benzoic acid)methylene Amidomonensine

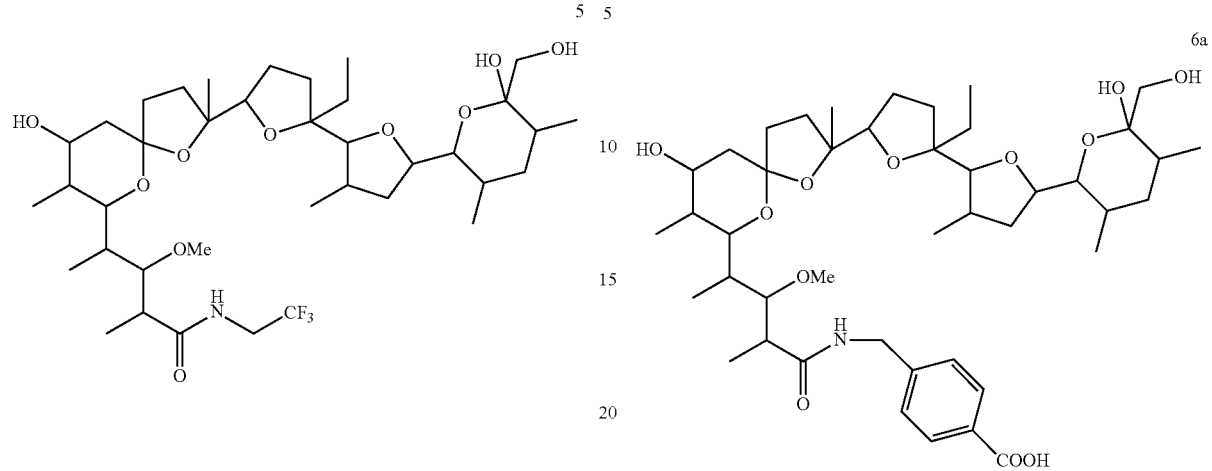

NMR ¹H (400 MHz, CDCl₃) ppm: 7.46 (1H, s), 4.32 (1H, m), 4.14 (1H, d, J=6.76 Hz), 3.97-3.85 (4H, m), 3.78 (1H, d, J=2.24 Hz), 3.50 (3H, s), 3.41 (4H, m), 2.56-2.53 (1H, m), 2.27-2.18 (2H, m), 2.17-2.05 (1H, m), 2.04-1.96 (4H, m), 1.84 (1H, d, J=10.56 Hz), 1.76-1.36 (16H, m), 1.23 (3H, d, J=7.04 Hz), 1.02 (3H, d, J=7.04 Hz), 0.94-0.85 (15H, m).

NMR ¹³C (400 MHz, CDCl₃) ppm: 177.06, 124 (q, J=277 Hz), 107.98, 97.84, 86.45, 86.08, 85.51, 83.20, 81.91, 77.36, 74.68, 71.19, 67.80, 67.38, 58.87, 42.10, 40.59 (q, J=33.54 Hz), 38.98, 37.44, 36.94, 36.62, 35.18, 34.63, 34.48, 33.37, 32.76, 31.16, 30.55, 27.67, 26.98, 25.06, 17.35, 16.35, 15.47, 14.03, 12.89, 10.87, 8.44.

NMR ¹⁹F (400 MHz, CDCl₃) ppm: -72.71 (t, J=9.72 Hz)
Exact mass: HR ESIMS: Calculated for $C_{38}H_{64}O_{10}NF_3Na^+$=774.4375. found=774.4388.

A mixture of monensin acid (502.2 mg, 0.75 mmol, 1 eq) and HOBt (123.1 mg, 0.90 mmol, 1.2 eq) in THF (3 mL) was stirred at 5° C. for 30 min and then DCC (189.5 mg, 0.90 mmol, 1.2 eq) was added. After being stirred for 1 h, the reaction mixture was treated with a solution of trifluoroethanamine hydrochloride (136.0 mg, 0.98 mmol, 1.3 eq) and N-methylmorpholine (110 μL, 0.98 mmol, 1.3 eq) in THF (2 mL), and stirring was maintained at room temperature during 3 days. The mixture was evaporated to dryness to give a powder, which was suspended in EtOAc (6 mL) and filtered off. The organic phase was washed with 10% citric acid solution (3 mL), saturated NaHCO₃ (3 mL) and distilled water (3 mL), successively, dried over MgSO₄ and evaporated to dryness. A purification on silica gel chromatography allows to afford 100 mg (18%) of the desired amide.

NMR ¹H (400 MHz, CDCl₃) ppm: 7.47 (2H, d, J=7.32 Hz), 6.79 (2H, d, J=7.32 Hz), 4.90 (1H, m), 4.69 (1H, m), 4.45-4.20 (2H, m), 4.01 (3H, m), 3.89-3.78 (2H, m), 3.61-3.55 (4H, m), 3.51-3.40 (1H, m), 3.30 (2H, d, J=10.56 Hz), 2.26-2.08 (5H, m), 2.03-1.83 (4H, m), 1.72-1.61 (6H, m), 1.58-1.49 (2H, m), 1.48-1.31 (4H, m), 1.24 (3H, m), 1.17-1.08 (3H, m), 1.04-0.69 (15H, m), 0.54 (3H, m).

NMR ¹³C (400 MHz, CDCl₃) ppm: 176.21, 171.67, 136.93, 129.61, 125.73, 121.20, 108.32, 97.92, 89.94, 86.06, 83.56, 81.35, 75.22, 73.74, 69.08, 67.82, 63.98, 62.70, 43.81, 43.50, 40.41, 39.68, 37.44, 35.62, 35.10, 34.54, 34.46, 33.05, 32.97, 31.52, 29.48, 29.09, 27.86, 26.13, 18.73, 16.35, 16.28, 16.18, 15.54, 14.44, 10.58, 7.99.

Exact mass: HR ESIMS: Calculated for $C_{44}H_{69}O_{12}NNa^+$= 826.4717. found=826.4719.

1-(4-methylbenzoate) methylene amidomonensin 3b (585.9 mg, 0.72 mmol, 1 eq) in 1N NaOH (5 mL) containing THF-MeOH—H₂O (2:2:1) was stirred at room temperature for 6 h. Then the mixture was evaporated to dryness to give a powder, which was suspended in EtOAc (6 mL) and filtered off. The solid was washed several times and the filtrate was evaporated to dryness. The solid was washed with dichloromethane and then filtered. The solid obtained is the product. The two fractions (filtrate and solid) were gathered to afford 332.6 mg (57%) of the desired acid.

Compound (6b)-(R)-2'-(monensinamido)-3'-(1'H-indol-3'-yl)propanoic Acid

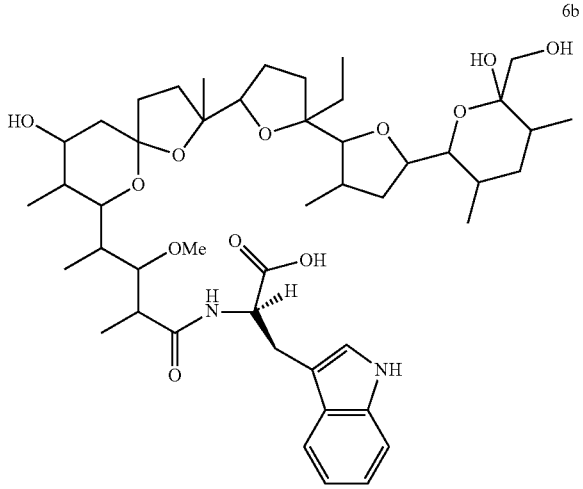

6b

NMR ¹H (400 MHz, D₂O/MeOD) ppm: 7.74 (1H, d, J=7.80 Hz), 7.52 (1H, d, J=8.32 Hz), 7.27 (2H, m), 7.19 (1H, t, J=7.56 Hz), 4.58 (1H, m), 4.45-4.25 (2H, m), 4.08 (2H, m), 3.89 (2H, m), 3.71-3.50 (4H, m), 3.23 (2H, m), 3.02 (3H, m), 2.43 (3H, m), 2.26 (2H, m), 2.15-1.95 (8H, m), 1.90-1.50 (10H, m), 1.37 (4H, d, J=9.32 Hz), 1.16-0.97 (18H, m), 0.85 (2H, d, J=6.80 Hz).

NMR ¹³C (400 MHz, D₂O/MeOD) ppm: 216.32, 188.07, 187.17, 179.18, 178.31, 171.67, 137.10, 128.58, 124.77, 122.58, 120.03, 119.56, 112.53, 111.19, 108.39, 88.83, 88.70, 86.07, 83.00, 81.31, 78.57, 71.23, 69.87, 62.54, 57.92, 56.40, 49.28, 42.58, 41.60, 36.72, 36.44, 36.03, 34.88, 30.86, 30.66, 30.41, 30.22, 28.17, 25.42, 19.88, 17.91, 16.50, 15.79, 13.45, 12.53, 10.78, 8.25.

Exact mass: HR ESIMS: Calculated for $C_{47}H_{72}O_{12}N_2Na^+$ = 879.4983. found=879.4982.

(R)-methyl 2'-(monensinamido)-3'-(1'H-indol-3'-yl)propanoate 4a (95.3 mg, 0.11 mmol, 1 eq) in 1N NaOH (1 mL) containing THF-MeOH—H₂O (2:2:1) was stirred at room temperature for 6 h. Then the mixture was evaporated to dryness to give a powder, which was suspended in dichloromethane (6 mL) and filtered off. The solid was washed several times with dichloromethane and the filtrate was evaporated to dryness to afford 86.6 mg (92%) of the desired acid.

Compound (7)—Monensin Lactone

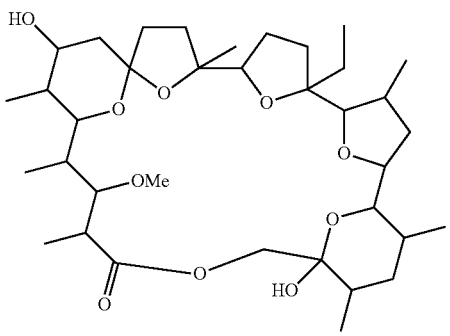

NMR ¹H (300 MHz, CDCl₃) ppm: 4.39 (1H, d, J=11.28 Hz), 4.27 (1H, m), 4.20 (1H, d, J=10.92 Hz), 4.02 (1H, d, J=4.5 Hz), 3.93 (1H, dd, 10.17 Hz), 3.83 (1H, d, J=2.85 Hz), 3.65 (1H, d, J=11.28 Hz), 3.60 (1H, m), 3.40 (1H, s), 3.35 (3H, s), 2.86 (1H, m), 2.18 (5H, m), 1.88 (3H, m), 1.71 (4H, m), 1.43 (15H, m), 1.18 (3H, d, 7.5 Hz), 0.93 (15H, m).

NMR ¹³C (400 MHz, CDCl₃) ppm: 178.19, 108.50, 97.03, 86.75, 85.86, 85.73, 85.69, 83.15, 79.37, 76.99, 74.05, 71.62, 68.68, 68.00, 58.56, 38.84, 38.30, 37.06, 36.01, 35.48, 35.17, 34.32, 33.89, 33.09, 32.90, 31.25, 30.89, 27.69, 25.27, 17.66, 17.00, 15.69, 12.58, 11.11, 10.29, 8.61.

Exact mass: HR ESIMS: Calculated for $C_{36}H_{60}O_{10}Na^+$ = 675.4084. found=675.4084.

In a three-necked round-bottom flask, equipped with reflux condenser, DCC (6.3 g, 30 mmol, 2 eq), DMAP (5.5 g, 45 mmol, 3 eq), DMAP.HCl (4.7 g, 30 mmol, 2 eq) and chloroform (850 mL) were introduced. The resulting solution was brought to reflux, and a solution of monensin acid (10 g, 15 mmol, 1 eq) in THF (150 mL) was slowly added over 2 h. After addition was completed, the reaction mixture was stirred at reflux during 12 h. Then, the reaction mixture was cooled to room temperature and quenched with methanol (20 mL) and acetic acid (3.6 mL). The stirring was continued for 30 min at room temperature. The solvent was removed under vacuum and then, the mixture was diluted with diethylether and filtered. The organic phase was washed with aqueous HCl solution (IN) and with distilled water, dried over MgSO₄ and evaporated over vacuum to afford 7.6 g (78%) of the expected product as a white powder.

Compound (8a)-25-Methoxymonensin

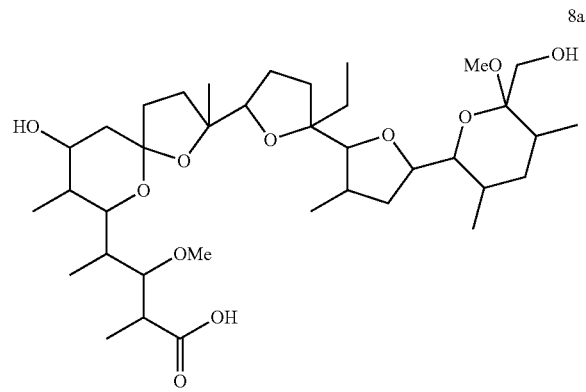 [SMILES: CCC1(C2OC(C3OC(CO)(OC)C(C)CC3C)CC2C)CCC(C2(C)CCC3(CC(O)C(C)C(C(C)C(OC)C(C)C(=O)O)O3)O2)O1]

8a

NMR ¹H (300 MHz, CDCl₃) ppm: 4.32 (1H, m), 4.06-4.03 (1H, m), 3.97-3.91 (1H, m), 3.88-3.85 (1H, m), 3.77-3.74 (1H, m), 3.71-3.61 (1H, m), 3.50-3.46 (1H, m), 3.42-3.36 (4H, m), 3.27-3.22 (4H, m), 2.65-2.60 (1H, m), 2.30-2.00 (5H, m), 1.99-1.80 (3H, m), 1.75-1.40 (8H, m), 1.39-1.21 (11H, m), 1.08 (3H, d, J=6.80 Hz), 1.04-0.83 (15H, m).

NMR ¹³C (300 MHz, CDCl₃) ppm: 177.17, 107.91, 86.45, 86.08, 85.62, 83.40, 83.62, 81.90, 77.31, 71.90, 71.52, 68.67, 67.52, 58.51, 48.95, 41.13, 38.69, 37.29, 36.72, 36.22, 35.06, 34.90, 34.07, 33.96, 33.15, 32.90, 31.57, 31.56, 28.28, 17.68, 16.05, 15.92, 12.67, 12.38, 11.19, 10.94, 8.92.

Exact mass: HR ESIMS: Calculated for $C_{37}H_{64}O_{11}Na^+$ = 707.4346. found=707.4346.

A mixture of monensin acid (3.07 g, 4.48 mmol, 1 eq), LiBr.H2O (49.8 mg, 0.45 mmol, 0.1 eq) and n-Bu₄NBr (75.8 mg, 0.22 mmol, 0.05 eq) in MeOH was stirred at room temperature. After 3 days, the reaction mixture was concentrated under vacuum. The residue was purified on silica gel chromatography (AcOEt/Cyclohexane: 60/40) to give the expected product (1.95 g, 68%).

Compound (8b)—25-Ethoxymonensin

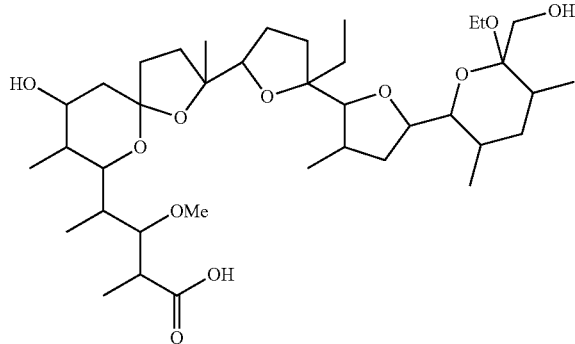

NMR $^1$H (400 MHz, CDCl$_3$) ppm: 4.33 (1H, m), 4.06 (1H, dd, J1=2.07 Hz, J2=11.28 Hz), 3.96 (1H, dd, J1=3.04 Hz, J2=10.32 Hz), 3.86 (1H, m), 3.74 (1H, d, J=15.36 Hz), 3.65-3.53 (2H, m), 3.48 (1H, d, J=10.92 Hz), 3.41 (2H, q, J=4.8 Hz), 3.36 (3H, s), 3.22 (1H, dd, J1=1.89 Hz, J2=10.17 Hz), 2.62 (2H, m), 2.25-2.04 (5H, m), 1.98-1.86 (4H, m), 1.70-1.46 (11H, m), 1.45-1.20 (7H, d, J=4.89 Hz), 1.14 (1H, t, J=6.80 Hz), 1.00 (2H, d, J=7.08 Hz), 0.97-0.83 (17H, m).

NMR $^{13}$C (400 MHz, CDCl$_3$) ppm: 177.36, 107.93, 86.45, 85.28, 85.08, 83.59, 81.72, 73.95, 71.69, 70.85, 68.02, 67.26, 67.17, 58.53, 58.15, 42.10, 38.51, 36.84, 35.75, 34.69, 34.21, 33.88, 32.96, 32.71, 31.62, 31.28, 27.98, 27.83, 27.05, 18.51, 17.68, 16.49, 15.89, 15.75, 10.89, 10.48, 8.71, 8.26.

Exact mass: HR ESIMS: Calculated for $C_{38}H_{66}O_{11}Na^+$= 721.4503. found=721.4503.

A mixture of monensin acid (1.04 g, 1.50 mmol, 1 eq), LiBr.H$_2$O (16.6 mg, 0.15 mmol, 0.1 eq) and n-Bu$_4$NBr (26.0 mg, 0.08 mmol, 0.05 eq) in EtOH was stirred at room temperature. After 2 days, the reaction mixture was concentrated under vacuum. The residue was purified on silica gel chromatography (AcOEt/Cyclohexane:50/50) to give the expected product (420 mg, 40%).

Compound (8c)—25-propoxymonensin

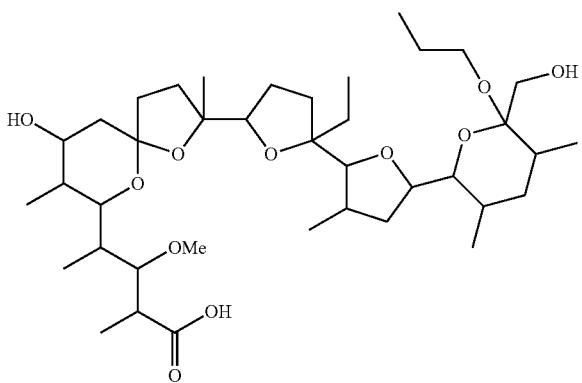

NMR $^1$H (400 MHz, CDCl$_3$) ppm: 4.40-4.31 (1H, m), 4.20-4.00 (2H, m), 3.998-3.3.91 (1H, m), 3.89-3.83 (1H, m), 3.70-3.59 (3H, m), 3.54-3.44 (1H, m), 3.42-3.36 (4H, m), 3.24 (1H, dd, J1=2.0 Hz, J2=9.8 Hz), 2.66-2.62 (1H, m), 2.29-2.03 (5H, m), 1.99-1.87 (3H, m), 1.72-1.46 (13H, m), 1.45-1.31 (4H, m), 1.28-1.21 (4H, m), 1.10-1.0.98 (3H, m), 0.97-0.88 (18H, m).

NMR $^{13}$C (400 MHz, CDCl$_3$) ppm: 177.32, 107.94, 97.19, 86.45, 85.66, 85.29, 83.79, 81.96, 77.32, 74.34, 71.21, 68.42, 67.44, 65.07, 58.42, 42.27, 38.75, 37.15, 36.94, 36.18, 34.94, 34.89, 34.36, 34.09, 33.14, 33.02, 31.81, 31.56, 28.26, 28.03, 26.27, 17.88, 16.63, 16.10, 16.04, 11.15, 10.80, 10.54, 8.97.

Exact mass: HR ESIMS: Calculated for $C_{39}H_{68}O_{11}Na^+$= 735.4659. found=735.4658.

A mixture of monensin acid (505.5 mg, 0.75 mmol, 1 eq), LiBr.H2O (10.0 mg, 0.08 mmol, 0.1 eq) and n-Bu$_4$NBr (15.0 mg, 0.04 mmol, 0.05 eq) in PrOH was stirred at room temperature. After 3 days at room temperature and 2 days at 50° C., the reaction mixture was concentrated under vacuum. The residue was purified on silica gel chromatography (Cyclohexane/AcOEt:60/40) to give the expected product (85 mg, 16%).

Compound (8d)—25-O-methoxyethanol Monensin

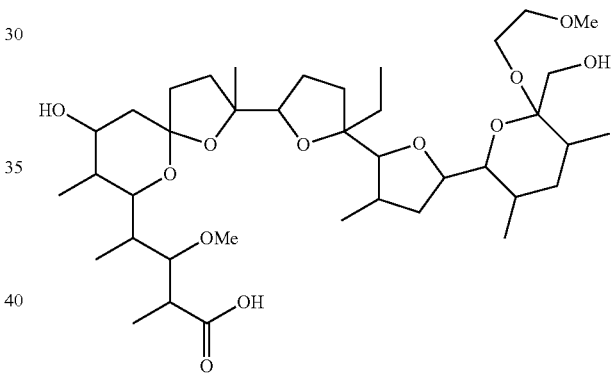

NMR $^1$H (400 MHz, CDCl$_3$) ppm: 4.27-4.21 (1H, m), 4.04 (1H, dd, J1=1.76 Hz, J2=9.32 Hz), 3.89 (1H, d, J=4.28 Hz), 3.76 (1H, d, J=2.8 Hz), 3.72-3.63 (2H, m), 3.61-3.53 (4H, m), 3.50-3.41 (3H, m), 3.39 (3H, s), 3.36 (3H, s), 2.64-2.61 (1H, m), 2.27-2.13 (3H, m), 2.12-1.86 (7H, m), 1.84-1.76 (1H, m), 1.73-1.60 (3H, m), 1.59-1.46 (4H, m), 1.41-1.25 (6H, m), 1.21 (3H, d, J=6.80 Hz), 1.00 (3H, d, J=7.04 Hz), 0.96 (15H, m).

NMR $^{13}$C (400 MHz, CDCl$_3$) ppm: 176.44, 107.50, 99.31, 88.13, 86.76, 83.53, 81.88, 76.62, 74.91, 74.07, 71.65, 68.84, 67.54, 62.11, 60.52, 59.28, 58.44, 41.85, 39.52, 38.67, 37.33, 36.74, 36.62, 34.90, 33.98, 33.88, 32.84, 31.55, 31.47, 28.28, 27.68, 24.46, 17.61, 16.16, 16.01, 15.86, 11.21, 11.02, 8.89.

Exact mass: HR ESIMS: Calculated for $C_{39}H_{68}O_{12}Na^+$= 751.4608. found=751.4607.

A mixture of monensin acid (509.0 mg, 0.75 mmol, 1 eq), LiBr.H$_2$O (10.5 mg, 0.08 mmol, 0.1 eq) and n-Bu$_4$NBr (12.2 mg, 0.04 mmol, 0.05 eq) in 2-methoxyethanol was stirred at room temperature. After 3 days at room temperature and 7 days at 50° C., the reaction mixture was concentrated under vacuum. The residue was purified on silica gel chromatography (AcOEt) to give the expected product (286.4 mg, 52%).

Compound (8e)—25-O-Glycidol Monensin

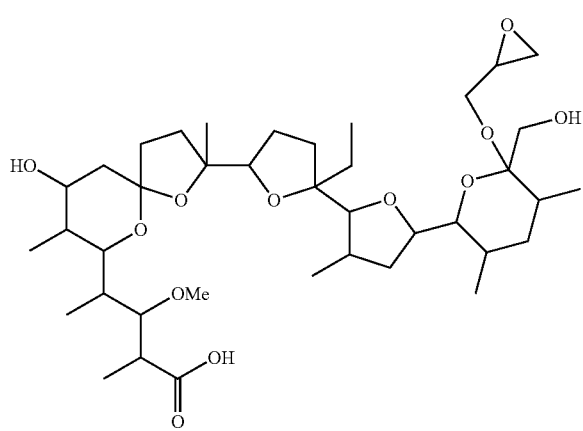

8e

NMR $^1$H (400 MHz, CDCl$_3$) ppm: 4.47-4.42 (1H, m), 4.42 (1H, m), 3.99-3.96 (3H, m), 3.87-3.76 (3H, m), 3.59 (2H, m), 3.47 (2H, s), 3.34 (3H, s), 3.23 (1H, m), 2.83 (1H, s), 2.71-2.65 (2H, m), 2.27 (1H, m), 2.14-1.61 (13H, m), 1.53-1.38 (9H, m), 1.22 (3H, d, J=6.04 Hz), 1.00-0.85 (18H, m).

NMR $^{13}$C (400 MHz, CDCl$_3$) ppm: 175.37, 107.70, 97.12, 87.27, 86.40, 85.71, 83.53, 81.56, 76.62, 76.17, 71.36, 68.07, 67.48, 65.13, 58.39, 49.49, 44.79, 41.06, 39.16, 37.14, 36.87, 36.20, 35.19, 34.88, 34.50, 33.56, 32.87, 32.54, 31.14, 29.77, 27.99, 25.92, 17.45, 16.26, 15.79, 12.35, 12.03, 11.22, 8.19.

Exact mass: FIR ESIMS: Calculated for C$_{39}$H$_{66}$O$_{12}$Na$^+$= 749.4452. found=749.4450.

A mixture of monensin acid (506.6 mg, 0.75 mmol, 1 eq), LiBr.H2O (10.5 mg, 0.08 mmol, 0.1 eq) and n-Bu$_4$NBr (17.2 mg, 0.04 mmol, 0.05 eq), glycidol (500 µL, 7.5 mmol, 10 eq) in dichloromethane was stirred at room temperature. After 4 days, the reaction mixture was heated to 31° C. After 4 days, the reaction mixture was concentrated under vacuum. The residue was purified on silica gel chromatography (Cyclohexane/AcOEt:60/40) to give the expected product (100 mg, 14%).

Compound (8f)—25-o-trifluoroethanol Monensin

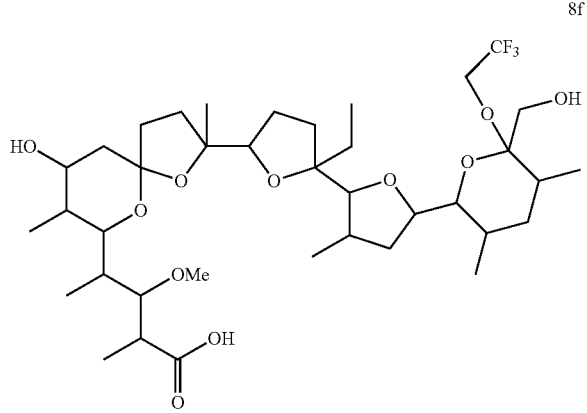 [SMILES: CCC1(C2OC(C3OC(CO)(OCC(F)(F)F)C(C)CC3C)CC2C)CCC(C2(C)CCC3(CC(O)C(C)C(C(C)C(OC)C(C)C(=O)O)O3)O2)O1]

8f

NMR $^1$H (400 MHz, CDCl$_3$) ppm: 4.30 (1H, m), 4.05-3.95 (3H, m), 3.86 (1H, d, J=4.56 Hz), 3.76 (1H, s), 3.68 (2H, dd, J=11.8 Hz), 3.58 (2H, m), 3.50 (1H, m), 3.36 (3H, s), 2.63 (1H, m), 2.33 (1H, m), 2.17 (1H, m), 2.09-1.83 (9H, m), 1.75-1.56 (6H, m), 1.51-1.42 (1H, m), 1.50-1.20 (9H, m), 0.99 (6H, d, J=5.04 Hz), 0.92-0.82 (12H, m).

NMR $^{13}$C (400 MHz, CDCl$_3$) ppm: 179.31, 124.45 (q, J=275.61 Hz), 107.68, 99.65, 88.00, 86.38, 86.09, 83.33, 81.45, 78.06, 77.36, 71.71, 68.20, 65.32, 59.75 (q, J=34.27 Hz), 58.27, 40.91, 39.12, 36.95, 36.44, 36.07, 35.82, 35.21, 34.80, 33.48, 32.46, 32.14, 28.71, 27.37, 27.05, 24.45, 21.19, 17.54, 16.34, 15.48, 12.09, 11.14, 8.00.

NMR $^{19}$F (400 MHz, CDCl$_3$) ppm: −74.46 (t, J=10.24 Hz)

Exact mass: FIR ESIMS: Calculated for C$_{38}$H$_{63}$O$_{11}$F$_3$Na$^+$= 775.4215. found=775.4196.

A mixture of monensin acid (501.0 mg, 0.75 mmol, 1 eq), LiBr.H2O (8.8 mg, 0.08 mmol, 0.1 eq) and n-Bu$_4$NBr (13.1 mg, 0.04 mmol, 0.05 eq) in trifluoroethanol was stirred at room temperature. After 4 days, the reaction mixture was heated to 31° C. After 22 days, the reaction mixture was concentrated under vacuum. The residue was purified on silica gel chromatography (AcOEt/Cyclohexane: (50/50) to give the expected product (61.5 mg, 11%)).

Compound (9)—25-methyllactone

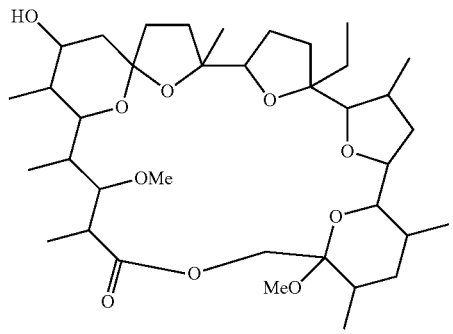

9

NMR $^1$H (400 MHz, CDCl$_3$) ppm: 4.30-4.18 (1H, m), 4.14-4.08 (1H, m), 4.04-3.95 (2H, m), 3.90 (1H, d, J=4.24 Hz), 3.78-3.55 (1H, m), 3.51-3.39 (3H, m), 3.34-3.29 (3H, m), 3.26 (3H, s), 2.63 (1H, m), 2.27-2.15 (3H, m), 2.11-1.70 (7H, m), 1.69-1.40 (4H, m), 1.37-1.25 (9H, m), 1.23-1.11 (4H, m), 1.00-0.79 (18H, m).

NMR $^{13}$C (400 MHz, CDCl$_3$) ppm: 175.01, 107.64, 98.49, 88.21, 86.70, 85.76, 85.33, 78.01, 77.62, 71.76, 68.60, 68.00, 66.26, 59.18, 48.81, 41.64, 39.75, 37.53, 37.46, 37.33, 36.11, 35.85, 35.44, 35.22, 34.38, 34.00, 30.72, 25.87, 25.18, 24.27, 18.02, 16.22, 12.89, 11.75, 11.48, 8.62, 8.42.

Exact mass: HR ESIMS: Calculated for C$_{37}$H$_{62}$O$_{10}$Na$^+$= 689.4241. found=689.4241.

In a three-necked round-bottom flask, equipped with reflux condenser, DCC (120 mg, 0.58 mmol, 2 eq), DMAP (108.1 mg, 0.87 mmol, 3 eq), DMAP.HCl (98.7 mg, 0.58 mmol, 2 eq) and chloroform (20 mL) were introduced. The resulting solution was brought to reflux, and a solution of 25-methylated monensin 8a (201 mg, 0.29 mmol, 1 eq) in THF (4 mL) was slowly added over 2 h. After addition was completed, the reaction mixture was stirred at reflux during 16 h. Then, the reaction mixture was cooled to room temperature and quenched with methanol (0.5 mL) and acetic acid (85 µL). The stirring was continued for 30 min at room temperature. The solvent was removed under vacuum and then, the mixture was diluted with diethylether and filtered. The organic phase was washed with aqueous HCl solution (1N) and with distilled water, dried over MgSO$_4$ and evaporated over vacuum to afford 173.1 mg (90%) of the expected product as a white powder.

Compound (12)—Oxo-dioxane Monensin

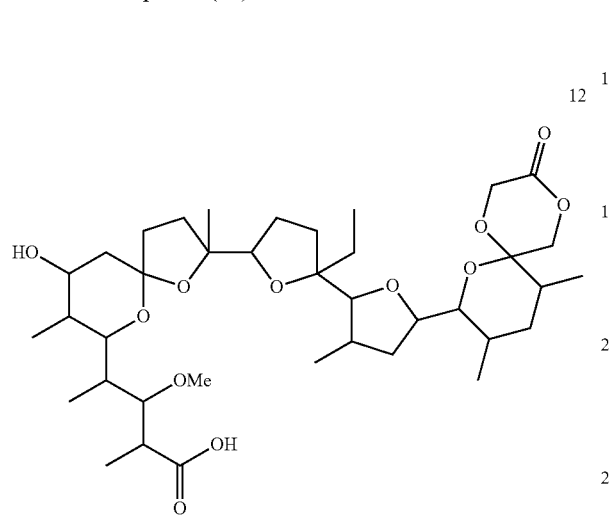

NMR $^1$H (400 MHz, CDCl$_3$) ppm: 4.47 (1H, d, J=11.32 Hz), 4.38 (1H, d, J=16.88 Hz), 4.26 (1H, d, J=17.12 Hz), 4.09 (1H, d, J=11.32 Hz), 4.01 (1H, d, J=8.8 Hz), 3.87 (1H, d, J=4.52 Hz), 3.77 (1H, m), 3.62 (1H, dd, J1=8.56 Hz, J2=9.04 Hz), 3.55 (1H, t, J=4.8 Hz), 3.39 (1H, m), 3.36 (3H, s), 2.66-2.60 (1H, m), 2.28 (1H, m), 2.16-1.85 (9H, m), 1.80-1.73 (2H, m), 1.69-1.48 (10H, m), 1.35-1.20 (6H, m), 1.03-0.86 (18H, m).

NMR $^{13}$C (400 MHz, CDCl$_3$) ppm: 178.69, 167.53, 107.43, 94.34, 88.09, 86.34, 85.29, 82.83, 81.27, 78.84, 77.36, 72.57, 71.64, 67.94, 59.64, 58.16, 40.86, 39.26, 36.96, 35.74, 35.53, 34.91, 34.58, 34.43, 33.18, 32.18, 32.01, 30.29, 28.84, 27.65, 24.33, 17.57, 16.45, 16.08, 12.92, 11.95, 11.03, 8.05.

Exact mass: HR ESIMS: Calculated for $C_{38}H_{62}O_{12}Na^+$= 733.4133. found=733.4102.

A mixture of monensin acid (500 mg, 0.75 mmol, 1 eq), LiBr.H2O (9.1 mg, 0.08 mmol, 0.1 eq) and n-Bu$_4$NBr (13.2 mg, 0.04 mmol, 0.05 eq), methyl glycolate (571 µL, 7.5 mmol, 10 eq) in dichloromethane was stirred at room temperature. After 3 days, the reaction mixture was heated to 40° C. After 6 days, the reaction mixture was concentrated under vacuum. The residue was chromatographed on silica gel (Cyclohexane/AcOEt:60/40) to give the expected product (212.1 mg, 40%).

Compound (13)—Acetylene Monensin

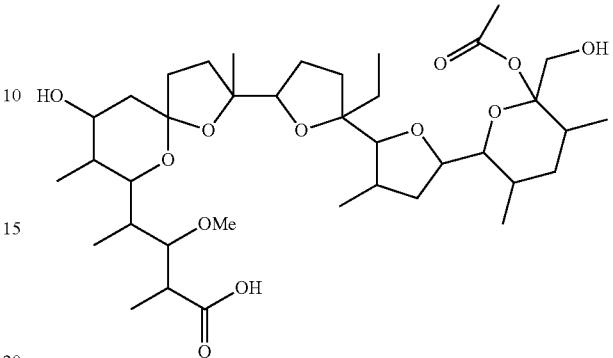

NMR $^1$H (400 MHz, CDCl$_3$) ppm: 4.30-4.24 (2H, m), 4.11 (2H, t, J=12.08 Hz), 4.01-3.98 (2H, m), 3.75 (1H, m), 3.47 (1H, m), 3.36 (3H, s), 3.26 (1H, dd, J1=2.04 Hz, J2=9.32 Hz), 2.66-2.2.62 (1H, m), 2.22-2.12 (6H, m), 2.05-1.86 (5H, m), 1.77-1.59 (6H, m), 1.56-1.30 (7H, m), 1.24 (3H, d, J=6.76 Hz), 1.09 (3H, d, J=6.80 Hz), 0.96-0.85 (18H, m).

NMR $^{13}$C (400 MHz, CDCl$_3$) ppm: 176.58, 171.10, 108.00, 97.00, 86.43, 85.80, 84.72, 83.33, 81.97, 77.36, 77.04, 74.94, 71.03, 67.41, 67.20, 58.18, 40.83, 38.71, 36.92, 36.34, 35.24, 34.86, 34.71, 34.59, 33.75, 32.77, 31.27, 30.58, 27.61, 27.43, 21.31, 17.71, 16.39, 16.01, 15.32, 10.90, 10.76, 8.54.

Exact mass: HR ESIMS: Calculated for $C_{38}H_{64}O_{12}Na^+$= 735.4295. found=735.4293.

A mixture of monensin acid (1.07 g, 1.50 mmol, 1 eq), LiBr.H$_2$O (18.0 mg, 0.15 mmol, 0.1 eq) and n-Bu$_4$NBr (24.6 mg, 0.08 mmol, 0.05 eq) in anhydride acetic was stirred at room temperature. After 3 days, the reaction mixture was concentrated under vacuum. The residue was chromatographed on silica gel (Cyclohexane/AcOEt:60/40) to give the expected product (182.7 mg, 17%).

Compound (14a)—7,25-dimethoxylactone

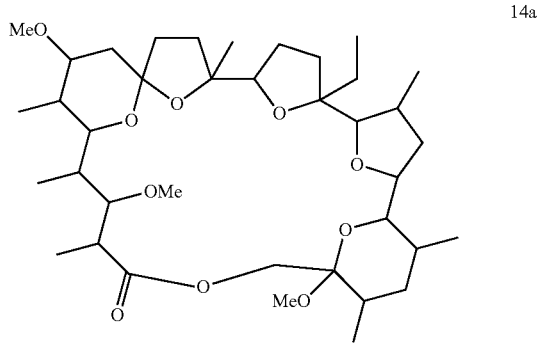

Exact mass: HR ESIMS: Calculated for $C_{38}H_{64}O_{10}Na^+$= 703.4397. found=703.4396.

Compound (14b)—7,25-diethoxylactone

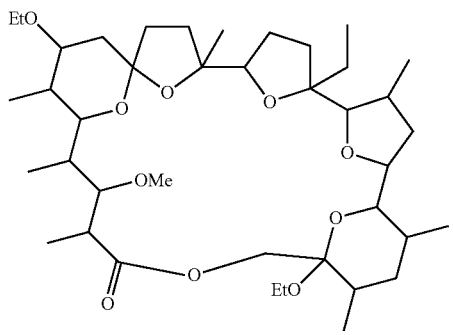

Exact mass: HR ESIMS: Calculated for $C_{40}H_{68}O_{10}Na^+=$ 731,4709. found=731.4709.

Compound (14c)—7,25-dipropoxylactone

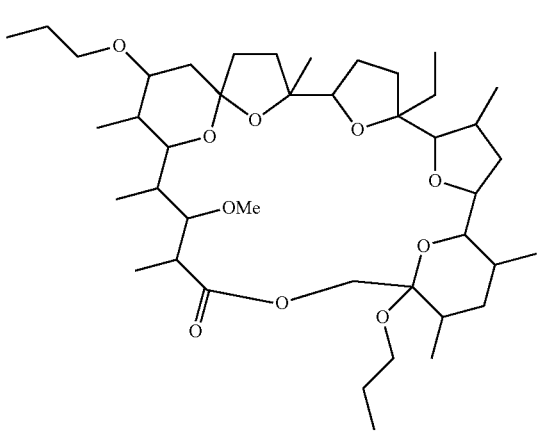

Exact mass: HR ESIMS: Calculated for $C_{42}H_{72}O_{10}Na^+=$ 759.5023. found=759.5020.

Compound (14d)—7,25-dibutylactone

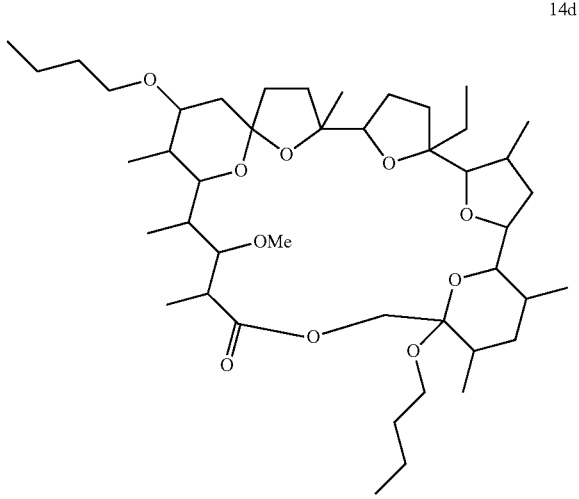 [SMILES: CCCCOC1CC23CCC(C)(O2)C2CCC(CC)(O2)C2OC(CC2C)C2OC(OCCCC)(COC(=O)C(C)C(OC)C(C)C(O3)C1C)C(C)CC2C]

Exact mass: HR ESIMS: Calculated for $C_{44}H_{76}O_{10}Na^+=$ 787.5336. found=787.5339.

Compound (14e)—7,25-diphenoxylactone

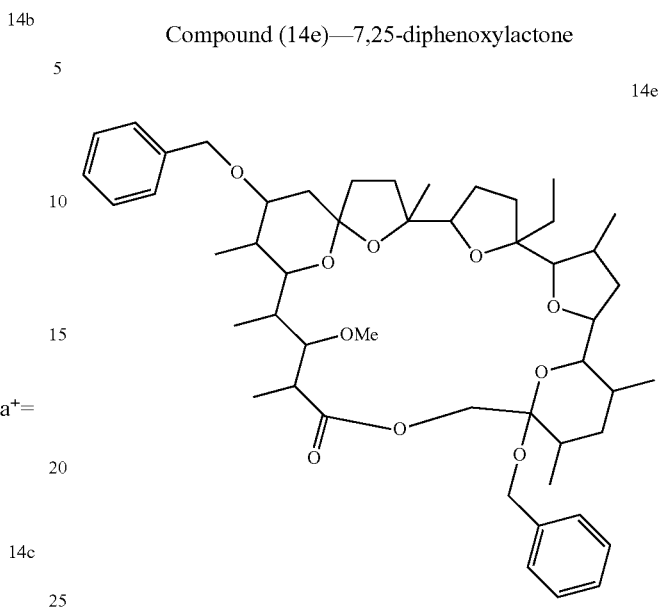

Exact mass: HR ESIMS: Calculated for $C_{50}H_{72}O_{10}Na^+=$ 855.5023. found=855.5021

Compound (14f)—25-methyl Monensin Methanoate

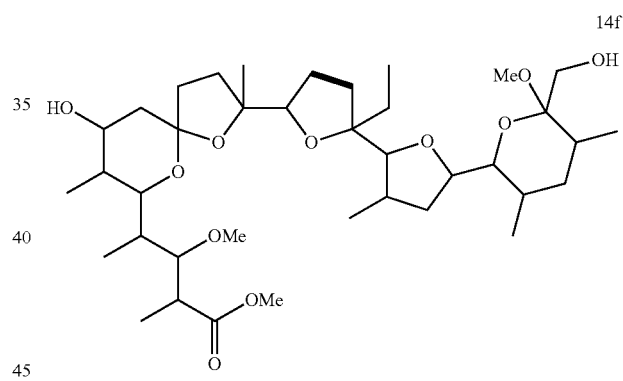

NMR $^1$H (400 MHz, CDCl$_3$) ppm: 4.29-4.27 (1H, m), 4.00 (1H, dd, J1=9.32 Hz, J2=2.04 Hz), 3.94 (1H, dd, J1=9.04 Hz, J2=2.24 Hz), 3.90 (1H, d, J=4.28 Hz), 3.83 (1H, d, J=4.80 Hz), 3.77 (1H, m), 3.73 (1H, m), 3.70 (3H, s), 3.52 (1H, m), 3.33 (4H, m), 3.26 (3H, s), 2.65-2.63 (1H, m), 2.32-2.22 (1H, m), 2.15-1.48 (16H, m), 1.38-1.21 (4H, m), 1.21-1.19 (3H, m), 1.10-0.85 (21H, m).

NMR $^{13}$C (400 MHz, CDCl$_3$) ppm: 176.00, 107.70, 107.42, 99.49, 97.55, 89.59, 86.44, 85.38, 81.70, 75.76, 71.56, 68.05, 63.89, 61.43, 58.33, 52.03, 43.32, 41.14, 39.15, 37.28, 37.20, 37.13, 36.16, 34.91, 32.79, 32.57, 31.16, 29.76, 28.71, 28.41, 17.62, 17.44, 15.78, 12.56, 12.23, 11.20, 8.18, 7.60.

Exact mass: HR ESIMS: Calculated for $C_{38}H_{66}O_{11}Na^+=$ 721.4503. found=721.4502.

Monensin acid (1.02 g, 1.50 mmol, 1 eq) was dissolved in MeOH (10 mL). The reaction mixture was cooled at −10° C. and BF$_3$-Et$_2$O (195 μL, 1.58 mmol, 1.05 eq) was added very slowly.

After 5 min stirring, the reaction mixture was stirred at room temperature. After 1 h30 stirring, the reaction medium was diluted with diethyl ether (5 mL) and dichloromethane (5 mL). The solution was neutralised by the addition of NH$_4$OH, extracted with dichloromethane and distilled water, dried over MgSO$_4$ and evaporated to dryness. A purification on silica gel column chromatography (Cyclohexane/AcOEt:70/30) allows to afford 133.0 mg (22%) of the expected compound.

Compound (17)—7,8-ene-21-fluoro-25-one Lactone Monensin

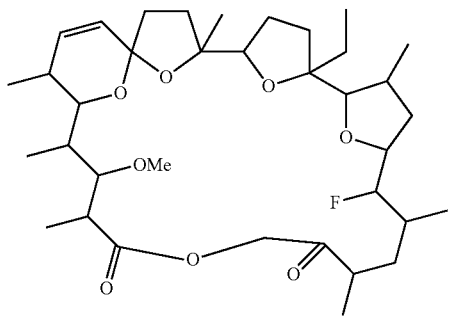

17

NMR $^1$H (400 MHz, CDCl$_3$) ppm: 5.87 (1H, m), 5.47 (1H, d, J=9.56 Hz), 5.19 (1H, d, J=17.36 Hz), 4.63 (1H, m, J=50.6 Hz), 4.34 (1H, d, J=17.60 Hz), 4.18 (1H, s), 3.97 (1H, m), 3.58 (3H, s), 3.54 (3H, d, J=11.04 Hz), 3.27 (1H, d, J=8.80 Hz), 2.73 (2H, m), 2.17-1.68 (14H, m), 1.50-0.90 (27H, m).

NMR $^{13}$C (400 MHz, CDCl$_3$) ppm: 206.16, 175.60, 135.28, 128.25, 105.10, 86.70, 85.67, 85.10 (d, J=174.3 Hz), 82.90, 82.89 (d, J=47.4 Hz), 82.45, 77.36, 70.11, 67.88, 60.08, 39.28, 39.11 (d, J=17.50 Hz), 38.88, 38.32, 37.20, 35.31, 34.34, 33.86, 30.90 (d, J=10.21 Hz), 30.83, 30.76, 29.87, 27.86, 22.34, 18.07, 16.39, 14.42, 13.83, 11.33, 8.60, 8.11.

NMR $^{19}$F (400 MHz, CDCl$_3$) ppm: −190.22.

Exact mass: HR ESIMS: Calculated for C$_{36}$H$_{57}$O$_8$FNa$^+$= 659.3935. found=659.3937.

In a dry three-neck round-bottomed flask, lactone monensin (200 mg, 0.31 mmol, 1 eq) was dissolved in anhydrous dichloromethane (20 mL) under argon. The mixture was cooled at −78° C. and DAST (80 μL, 0.62 mmol, 2 eq) was added very slowly. At the end of the addition, the reaction was stirring at room temperature during 50 min. The reaction mixture was washed several times with distilled water, dried over MgSO$_4$ and evaporated to dryness to afford 65.5 mg (33%) of the desired lactone.

Compound (18)—Triacetone Lactone

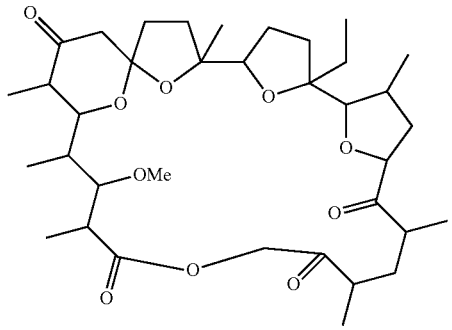

18

NMR $^1$H (400 MHz, CDCl$_3$) ppm: 5.13 (1H, d, J=17.12 Hz), 4.52 (1H, dd, J1=10.08 Hz, J2=9.84 Hz), 4.42 (1H, d, J=16.84 Hz), 4.30 (1H, t, J=3.52 Hz), 3.94 (1H, d, J=4.28 Hz), 3.90 (1H, dd, J1=8.56 Hz, J2=2.28 Hz), 3.59 (1H, m), 3.51 (3H, m), 3.24 (1H, m), 2.75 (3H, m), 2.41 (1H, dd, J1=7.32 Hz, J2=3.28 Hz), 2.34 (1H, d, J=15.60 Hz), 2.30-2.21 (1H, m), 2.20-2.01 (6H, m), 1.97-1.82 (5H, m), 1.76-1.70 (1H, m), 1.55-1.48 (2H, m), 1.45-1.39 (1H, m), 1.36 (3H, m), 1.18-1.11 (9H, m), 0.99-0.90 (12H, m).

NMR $^{13}$C (400 MHz, CDCl$_3$) ppm: 217.29, 210.69, 205.36, 175.47, 107.27, 87.35, 87.24, 87.12, 83.09, 81.56, 81.16, 77.35, 70.25, 66.84, 59.14, 49.81, 47.23, 39.73, 39.22, 39.02, 38.71, 38.48, 37.94, 35.62, 35.07, 33.89, 30.58, 30.10, 28.26, 22.29, 18.08, 15.68, 15.40, 11.71, 8.99, 8.25.

Exact mass: HR ESIMS: Calculated for C$_{36}$H$_{56}$O$_{10}$Na$^+$= 671.3766. found=671.3794.

A solution of lactone monensin (103.0 mg, 0.15 mmol, 1 eq) in dichloromethane (2 mL) was added to a stirred solution of Dess-Martin periodinane in dichloromethane 15% wt (360 μL, 0.17 mmol, 1.14 eq) over 5 min at room temperature under argon. After 4 h Dess-Martin periodinane (150 μL, 0.5 eq) was added to the reaction mixture. After 12 h, Dess-Martin periodinane (50 μL, 1.5 eq) was added to the reaction mixture. After 1 day, the reaction mixture was extracted with diethyl ether and NaOH (1N), washed with distilled water, dried over MgSO$_4$ and evaporated to dryness to afford 70.0 mg (72%) of the trioxydated lactone.

Compound (19)—oxo-lactone Monensin

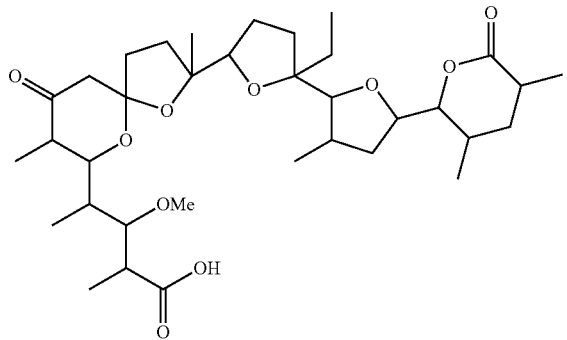

19

NMR $^1$H (400 MHz, CDCl$_3$) ppm: 4.24 (1H, m), 4.14 (2H, m), 3.98 (1H, m), 3.64 (1H, m), 3.55 (1H, m), 3.37 (3H, s), 2.74 (2H, m), 2.63 (1H, m), 2.50-241 (2H, m), 2.29-2.01 (7H, m), 1.95-1.85 (1H, m), 1.75 (2H, m), 1.69-1.40 (7H, m), 1.33-1.17 (9H, m), 1.15-1.06 (6H, m), 0.97-0.89 (9H, m).

NMR $^{13}$C (400 MHz, CDCl$_3$) ppm: 211.14, 197.35, 174.56, 107.82, 88.34, 88.23, 86.44, 86.37, 83.69, 82.30, 77.36, 71.42, 59.04, 47.34, 46.73, 40.87, 39.73, 37.49, 37.02, 36.15, 35.11, 35.07, 31.92, 31.68, 31.08, 29.97, 29.14, 25.22, 18.37, 17.27, 15.86, 11.98, 11.22, 10.91, 8.24.

Exact mass: HR ESIMS: Calculated for C$_{35}$H$_{56}$O$_{10}$Na$^+$= 659.3771. found=659.3772.

A solution of monensin acid (1.0 g, 1.49 mmol, 1 eq) in dichloromethane (20 mL) was added to a stirred solution of Dess-Martin periodinane in dichloromethane 15% wt (9.5 mL, 4.48 mmol, 3 eq) over 5 min at room temperature under argon. After 1 day, the reaction mixture was extracted with diethyl ether and NaOH (1N), washed with distilled water, dried over MgSO$_4$ and evaporated to dryness. A purification on silica gel column chromatography (Cyclohexane/AcOEt: 50/50) allows to afford 230.0 mg (24%) of the oxydated monensin.

Compound (20a)—Monensin Methanoate

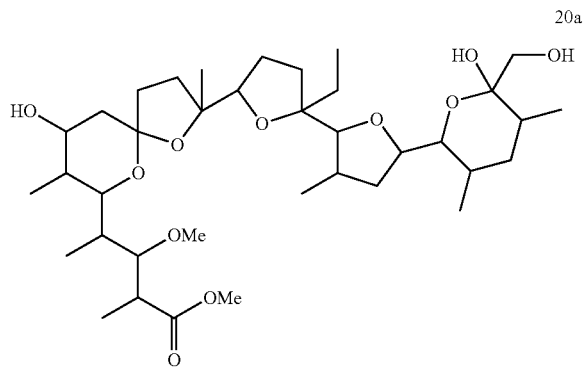 [SMILES: CCC1(C2OC(C3OC(O)(CO)C(C)CC3C)CC2C)CCC(C2(C)CCC3(CC(O)C(C)C(C(C)C(OC)C(C)C(=O)OC)O3)O2)O1]

20a

NMR $^1$H (400 MHz, CDCl$_3$) ppm: 4.29-4.25 (1H, m), 3.98 (1H, dd, J1=2.24 Hz, J2=9.32 Hz), 3.86 (1H, d, J=4.56 Hz), 3.81 (1H, dd, J1=2.28 Hz, J2=9.84 Hz), 3.76 (1H, d, J=3.04 Hz), 3.70 (3H, s), 3.60-3.53 (2H, m), 3.47 (2H, s), 3.32 (3H, s), 2.66 (1H, m), 2.27 (1H, m), 2.16-2.08 (2H, m), 2.07-1.94 (3H, m), 1.90-1.78 (4H, m), 1.68-1.60 (4H, m), 1.57-1.20 (10H, m), 1.19 (3H, d, J=7.04 Hz), 0.99 (7H, dd, J1=7.04 Hz, J2=16.60 Hz), 0.91-0.81 (11H, m).

NMR $^{13}$C (400 MHz, CDCl$_3$) ppm: 176.11, 107.71, 97.19, 87.10, 86.43, 85.70, 83.55, 81.76, 77.36, 77.08, 71.36, 68.11, 67.43, 58.36, 52.03, 41.02, 39.13, 37.17, 36.88, 36.10, 35.18, 34.89, 34.49, 33.51, 32.87, 32.67, 31.17, 29.77, 27.93, 25.92, 17.44, 16.29, 15.77, 12.32, 12.25, 11.20, 8.20.

Exact mass: HR ESIMS: Calculated for $C_{37}H_{64}O_{11}Na^+$= 707.4346. found=707.4347. Monensin acid (1.0 g, 1.50 mmol, 1 eq) was dissolved in anhydrous toluene (6 mL) under argon. 1,8-diazabicyclo[5.4.0]undec-7-ene (DBU) (250 µL, 1.65 mmol, 1.1 eq) and methyl iodide (122 µL, 1.95 mmol, 1.3 eq) were added. The reaction mixture was stirred at room temperature during 5 days. The reaction mixture was extracted with AcOEt and HCl (1N), washed with saturated NaHCO$_3$ and distilled water, dried over MgSO$_4$ and evaporated to dryness. A purification on silica gel column chromatography allows to afford 538.1 mg (52%) of the desired ester.

Compound (20b)—Monensin Glycidolate

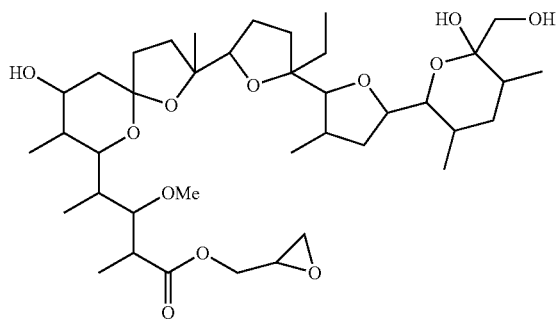

20b

NMR $^1$H (400 MHz, CDCl$_3$) ppm: 4.47-4.40 (2H, m), 4.34-4.25 (1H, m), 4.04-3.94 (3H, m), 3.83 (1H, d, J=4.52 Hz), 3.81-3.75 (2H, m), 3.62-3.57 (2H, m), 3.46 (2H, d, J=6.80 Hz), 3.34 (3H, s), 3.27-3.20 (1H, m), 2.83 (1H, t, J=4.76 Hz), 2.74-2.65 (2H, m), 2.28-2.22 (1H, m), 2.18-2.04 (2H, m), 1.99-1.80 (6H, m), 1.75-1.31 (13H, m), 1.27-1.20 (3H, m), 1.02-0.84 (18H, m).

NMR $^{13}$C (400 MHz, CDCl$_3$) ppm: 175.37, 107.73, 97.01, 87.45, 86.33, 85.92, 83.60, 81.59, 77.36, 76.53, 71.45, 68.12, 67.64, 65.37, 65.13, 58.38, 49.50, 44.80, 41.07, 39.21, 37.13, 36.90, 36.17, 35.26, 34.94, 34.55, 32.90, 32.41, 31.14, 29.80, 28.07, 25.82, 17.47, 16.23, 15.79, 12.35, 12.03, 11.24, 8.19.

Exact mass: HR ESIMS: Calculated for $C_{39}H_{66}O_{12}Na^+$= 749.4452. found=749.4452.

In a three-necked round-bottom flask, monensin acid (506.6 mg, 0.75 mmol, 1 eq), DCC (318 mg, 1.50 mmol, 2 eq), DMAP (277.8 mg, 2.25 mmol, 3 eq), DMAP.HCl (239.9 mg, 1.50 mmol, 2 eq) and dichloromethane (5 mL) were introduced. The resulting solution was stirring at room temperature and glycidol (251 µL, 3.75 mmol, 5 eq) was added. The reaction mixture was stirred at room temperature during 17 h. The solvent was removed under vacuum and then, the mixture was suspended in AcOEt and filtered off. The organic phase was washed with aqueous HCl solution (1N) and with distilled water, dried over MgSO$_4$ and evaporated over vacuum. A purification on silica gel column allows to afford 148.2 mg (27%) of the expected product as a white powder.

Compound (20c)—Monensin Methoxyethanoate

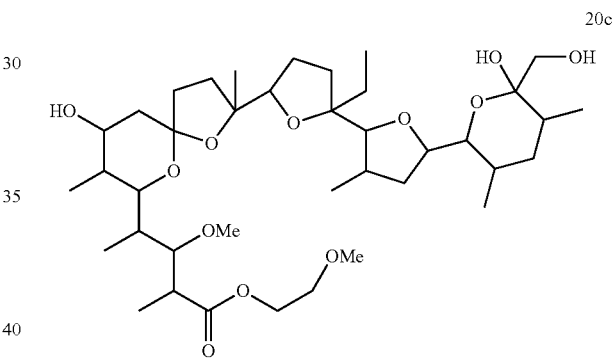

20c

NMR $^1$H (400 MHz, CDCl$_3$) ppm: 4.26 (3H, d, J=4.8 Hz), 4.15-3.95 (1H, m), 3.85-3.74 (3H, m), 3.67-3.59 (4H, m), 3.51-3.43 (2H, m), 3.37 (3H, s), 3.33 (3H, s), 2.76-2.60 (1H, m), 2.39-2.21 (1H, m), 2.14-2.11 (2H, m), 2.01-1.85 (6H, m), 1.81-1.60 (5H, m), 1.55-1.48 (3H, m), 1.38-1.21 (8H, m), 1.15-1.05 (2H, m), 1.00-0.86 (18H, m).

NMR $^{13}$C (400 MHz, CDCl$_3$) ppm: 175.69, 107.72, 97.06, 87.40, 86.40, 86.08, 83.88, 82.03, 76.86, 76.67, 71.72, 70.86, 68.43, 67.79, 63.95, 59.28, 58.71, 49.59, 41.28, 39.48, 37.61, 37.18, 36.51, 35.52, 35.16, 34.83, 34.34, 31.42, 29.98, 26.00, 25.34, 24.04, 17.73, 16.51, 16.06, 12.75, 12.11, 11.51, 8.43.

Exact mass: FIR ESIMS: Calculated for $C_{39}H_{68}O_{12}Na^+$= 751.4603. found=751.4589.

Monensin acid (499.0 mg, 0.75 mmol, 1 eq), DCC (313 mg, 1.50 mmol, 2 eq), DMAP (276.9 mg, 2.25 mmol, 3 eq) and THF (5 mL) were introduced in a round-bottomed flask. The resulting solution was stirring at room temperature during 30 minutes and methoxyethanol (100 µL, 1.26 mmol, 1.7 eq) was added. The reaction mixture was stirred at room temperature during 19 h. The solvent was removed under vacuum and then, the mixture was suspended in AcOEt and filtered off. The organic phase was washed with aqueous HCl solution (1N) and with distilled water, dried over MgSO$_4$ and evaporated over vacuum. A purification on silica gel column (Cyclohexane/AcOEt:50/50) allows to afford 114.3 mg (21%) of the expected product as a white powder.

Compound (21) 26-C-nosylaniline Monensin-25-ene

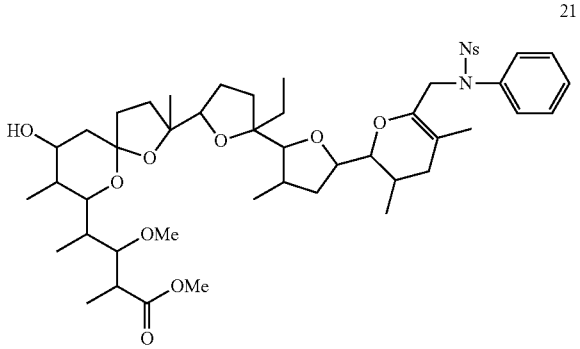

NMR ¹H (400 MHz, CDCl₃) ppm: 7.60 (2H, d, J=3.52 Hz), 7.49 (1H, d, J=7.80 Hz), 7.43 (1H, m), 7.26 (3H, m), 7.15 (2H, m), 4.51 (1H, d, J=14.36 Hz), 4.30 (1H, d, J=14.36 Hz), 4.08 (1H, m), 3.93 (1H, dd, J1=9.56 Hz, J2=2.0 Hz), 3.81 (1H, d, J=4.28 Hz), 3.75 (1H, d, J=3.0 Hz), 3.70 (3H, s), 3.66 (1H, m), 3.52 (1H, t, J=5.04 Hz), 3.33 (4H, m), 2.66-2.63 (1H, m), 2.24-2.11 (2H, m), 2.10-1.98 (4H, m), 1.88-1.84 (4H, m), 1.74-1.45 (10H, m), 1.43-1.37 (3H, m), 1.28-1.19 (6H, m), 1.00 (3H, d, J=7.08 Hz), 0.95-0.85 (12H, m).

NMR ¹³C (400 MHz, CDCl₃) ppm: 176.01, 148.16, 141.13, 137.98, 133.35, 132.86, 132.22, 131.09, 130.26, 129.07, 128.42, 123.95, 107.66, 107.43, 88.82, 86.65, 85.83, 83.58, 82.05, 81.67, 76.39, 71.67, 68.04, 60.54, 58.29, 53.57, 52.03, 51.75, 41.16, 39.86, 37.10, 36.19, 35.83, 35.04, 34.70, 31.73, 31.08, 30.12, 29.34, 29.30, 27.06, 24.80, 17.70, 17.14, 15.99, 12.72, 12.19, 11.19, 8.26.

Exact mass: HR ESIMS: Calculated for $C_{49}H_{70}O_{13}N_2SNa^+$=949.4491. found=949.4464.

A solution of the methanoate monensin 20a (50.7 mg, 0.08 mmol, 1 eq), triphenylphosphine (41.2 mg, 0.15 mmol, 2 eq) and nosylated aniline (42.1 mg, 0.15 mmol, 2 eq) in anhydrous tetrahydrofuran (1 mL) was stirred at room temperature under anhydrous conditions. Diethylazadicarboxylate DEAD (26 µL, 0.17 mmol, 2.2 eq) was added slowly at room temperature. After 3 days, the solution was concentrated under reduced pressure and then diluted with a small quantity of ether and filtered. After evaporation, the concentrated filtrate was chromatographed on silica gel (Cyclohexane/AcOEt:70/30). The expected compound was obtained with 61% isolated yield (45.3 mg).

Compound (23b)—Monensin 0-7-methyl, 0-25-glycolic Acid

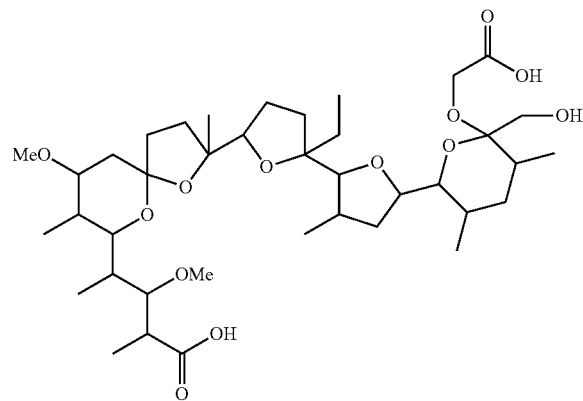

NMR ¹H (400 MHz, MeOD) ppm: 4.30-4.24 (1H, m), 4.13-4.04 (4H, m), 3.77 (1H, d, J=2.76 Hz), 3.73-3.68 (1H, m), 3.60-3.56 (2H, m), 3.48 (1H, dd, J1=3.28 Hz, J2=9.84 Hz), 3.40-3.35 (7H, m), 2.60-2.57 (1H, m), 2.39-2.37 (1H, m), 2.33-2.22 (1H, m), 2.16-1.79 (10H, m), 1.72-1.55 (5H, m), 1.50-1.25 (7H, m), 1.18 (3H, d, J=7.04 Hz), 1.03-1.00 (6H, m), 0.98-0.90 (12H, m).

NMR ¹³C (400 MHz, MeOD) ppm: 179.70, 176.29, 108.66, 101.56, 88.75, 87.86, 86.22, 84.15, 83.46, 79.19, 79.08, 75.73, 72.48, 69.00, 60.87, 59.96, 58.83, 42.50, 40.43, 38.48, 37.59, 37.56, 36.46, 36.39, 35.55, 35.39, 34.42, 32.91, 32.62, 30.48, 28.99, 25.97, 18.06, 16.55, 16.30, 12.87, 12.74, 11.34, 8.52.

Exact mass: HR ESIMS: Calculated for $C_{39}H_{66}O_{13}Na^+$=765.4427. found=765.4396.

A solution of monensin oxodioxane 12 (50.7 mg, 0.07 mmol, 1 eq) in anhydrous tetrahydrofuran (1.5 mL) was stirred in the presence of NaH (60% in oil) (15 mg, 0.35 mmol, 5 eq) at 50° C. for 30 min. The mixture was cooled to room temperature and methyl iodide (22 µL, 0.35 mmol, 5 eq) was added. The reaction mixture was stirred at room temperature for 18 h, quenched by the addition of a saturated NH₄Cl solution and diluted with AcOEt. The organic layer was washed with a saturated NaCl solution, dried over MgSO₄, filtered and evaporated to dryness. The residue was chromatographed on the silica gel (AcOEt/MeOH:90/10) to give the expected product as a powder (22.1 mg, 43%).

Compound (24a)—C-7-Acetate Monensin Oxodioxane

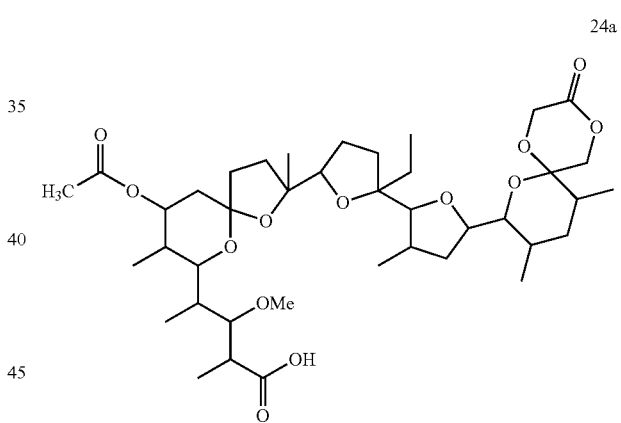

NMR ¹H (400 MHz, C₆D₆) ppm: 4.85 (1H, s), 4.38-3.35 (2H, m), 4.17 (1H, m), 4.08 (1H, d, J=5.04 Hz), 4.01 (1H, d, J=17.03 Hz), 3.88 (1H, d, J=11.36 Hz), 3.71-3.69 (2H, m), 3.61 (1H, d, J=11.03 Hz), 3.31 (1H, m), 3.22 (3H, s), 2.73 (1H, m), 2.23-1.98 (12H, m), 1.95-1.76 (4H, m), 1.64-1.41 (7H, m), 1.29 (3H, d, J=7.04 Hz), 1.17 (3H, d, J=7.08 Hz), 1.09 (4H, m), 1.01 (3H, t, J=7.32 Hz), 0.95 (3H, d, J=7.04 Hz), 0.86 (3H, d, J=7.04 Hz), 0.73 (3H, d, J=5.76 Hz), 0.60 (3H, d, J=5.52 Hz).

NMR ¹³C (400 MHz, C₆D₆) ppm: 179.86, 170.23, 166.23, 106.08, 94.34, 87.21, 86.66, 85.46, 83.16, 82.33, 79.17, 77.46, 73.60, 72.00, 68.34, 59.92, 58.33, 41.15, 40.00, 37.67, 37.12, 35.81, 35.07, 34.82, 34.13, 33.51, 33.32, 32.98, 32.47, 28.93, 27.86, 23.95, 21.53, 17.52, 16.58, 15.96, 12.52, 12.03, 10.63, 8.13.

Exact mass: FIR ESIMS: Calculated for $C_oH_{64}O_{13}Na^+$=775.4239. found=775.4219.

To a solution of monensin oxodioxane 12 (397 mg, 0.56 mmol, 1 eq) in dry pyridine (4 mL) were added acetic anhydride (1 mL, 10.08 mmol, 18 eq) and DMAP (10 mg, 0.07 mmol, 0.13 eq). The mixture was stirred at room temperature. After one day, the reaction was quenched with 10% Na₂CO₃ solution, then extracted with AcOEt. The extract was washed with 1N HCl, saturated NaHCO₃ and NaCl solution, dried over MgSO₄ and evaporated to dryness. The residue was chromatographed on silica gel (Cyclohexane/AcOEt:70/30) to give the expected product as a powder (87 mg, 21%).

Compound (25)—Monensin Oxodioxane Methanoate

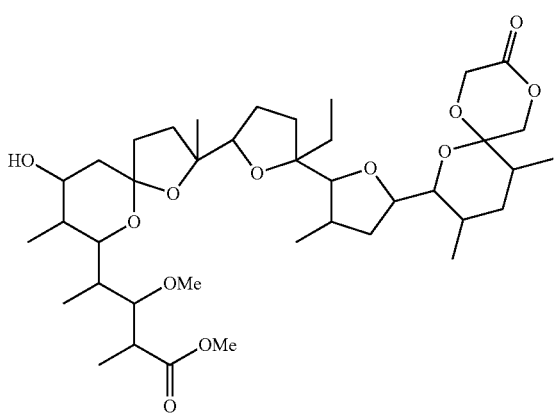

NMR $^1$H (400 MHz, CDCl₃) ppm: 4.47 (1H, d, J=11.36 Hz), 4.38 (1H, d, J=16.84 Hz), 4.22 (2H, d, J=17.12 Hz), 4.09 (1H, d, J=11.32 Hz), 3.92 (1H, dd, J1=1.76 Hz, J2=9.56 Hz), 3.86 (1H, d, J=4.56 Hz), 3.70 (4H, s), 3.62 (1H, m), 3.51 (1H, t, J=4.80 Hz), 3.37 (1H, dd, J1=3.76 Hz, J2=10.04 Hz), 3.33 (3H, s), 2.64 (1H, m), 2.29 (1H, m), 2.17-2.09 (1H, m), 2.08-1.90 (6H, m), 1.87-1.74 (4H, m), 1.69-1.52 (7H, m), 1.50-1.39 (1H, m), 1.36-1.25 (4H, m), 1.20 (3H, d, J=6.80 Hz), 1.10-0.85 (18H, m).

NMR $^{13}$C (400 MHz, CDCl₃) ppm: 175.98, 167.16, 107.50, 94.37, 88.02, 86.36, 85.42, 82.93, 81.72, 78.92, 77.36, 77.25, 72.54, 71.55, 67.99, 59.68, 58.33, 52.00, 41.13, 39.29, 37.12, 37.01, 36.16, 35.59, 34.92, 34.80, 34.51, 33.23, 32.22, 28.80, 27.63, 24.22, 17.59, 16.47, 16.09, 12.69, 12.22, 11.19, 8.05.

Exact mass: HR ESIMS: Calculated for C₃₉H₆₄O₁₂Na⁺=747.4303. found=747.4275.

Monensin oxodioxane 12 (132 mg, 0.18 mmol, 1 eq) was dissolved in anhydrous toluene (1.3 mL) under argon. 1,8-diazabicyclo[5.4.0]undec-7-ene (DBU) (30 µL, 0.20 mmol, 1.1 eq) and methyl iodide (15 µL, 0.24 mmol, 1.3 eq) were added. The reaction mixture was stirred at room temperature during 2 days. The reaction mixture was evaporated to dryness. A purification on silica gel column chromatography allows to afford 90.0 mg (69%) of the desired ester.

Compound (26)-7-oxo-monensin Oxodioxane

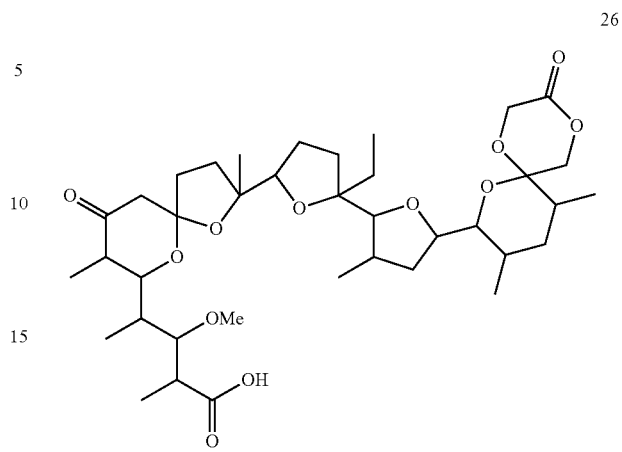

NMR $^1$H (400 MHz, CDCl₃) ppm: 4.48 (1H, d, J=11.32 Hz), 4.38 (1H, d, J=17.12 Hz), 4.26 (1H, d, J=17.12 Hz), 4.22 (1H, m), 4.18-4.12 (2H, m), 3.84 (1H, d, J=4.52 Hz), 3.64-3.56 (2H, m), 3.40-3.37 (4H, m), 2.79-2.72 (2H, m), 2.65-2.62 (1H, m), 2.40 (1H, d, J=15.36 Hz), 2.31-2.26 (1H, m), 2.16-1.93 (6H, m), 1.86-1.66 (3H, m), 1.62-1.42 (7H, m), 1.34-1.25 (4H, m), 1.18 (3H, d, J=6.76 Hz), 1.12 (3H, d, J=7.08 Hz), 0.97-0.84 (15H, m).

NMR $^{13}$C (400 MHz, CDCl₃) ppm: 210.92, 179.68, 167.62, 107.61, 94.34, 87.84, 86.24, 85.53, 83.28, 82.35, 78.79, 77.26, 72.57, 71.56, 59.69, 59.13, 47.40, 46.76, 40.78, 39.33, 37.11, 36.99, 35.55, 34.90, 34.39, 33.24, 32.87, 32.25, 28.79, 27.80, 24.72, 17.61, 16.48, 16.11, 12.02, 11.01, 10.90, 8.12.

Exact mass: HR ESIMS: Calculated for C₃₈H₆₀O₁₂Na⁺=731.3977. found=731.3950.

A solution of monensin oxodioxane 12 (172.4 mg, 0.28 mmol, 1 eq) in dichloromethane (4 mL) was added to a stirred solution of Dess-Martin periodinane in dichloromethane 15% wt (872 µL, 0.42 mmol, 1.5 eq) over 5 min at room temperature under argon. After 1 day, the reaction mixture was diluted with diethyl ether and then stirred 5 min with a saturated Na₂S₂O₃ solution, extracted and washed with distilled saturated NaHCO₃, NaCl solution, dried over MgSO₄ and evaporated to dryness. A purification on silica gel column chromatography (Hexane/Acetone:70/30) allows to afford 51.6 mg (26%) of the oxydated product.

Compound (27)—O-25-glycolic Acid Monensin

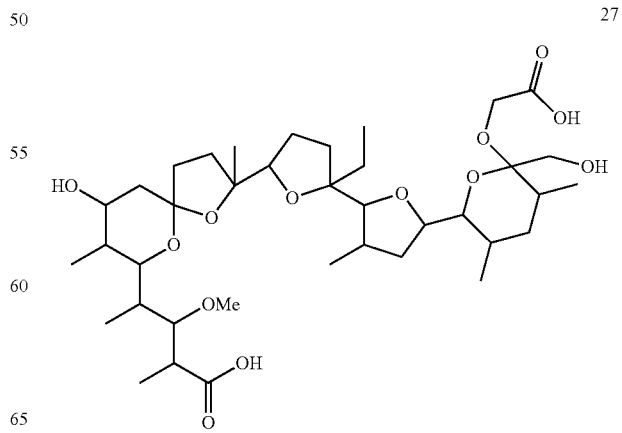

NMR $^1$H (400 MHz, MeOD) ppm: 4.27-4.21 (1H, m), 4.12-4.04 (3H, m), 3.95 (1H, d, J=15.6 Hz), 3.76 (1H, d, J=2.52 Hz), 3.64-3.55 (2H, m), 3.51-3.48 (1H, m), 3.47-3.43 (2H, m), 3.32 (3H, s), 2.40-2.31 (2H, m), 2.20-2.13 (2H, m), 1.98-1.88 (5H, m), 1.84-1.73 (4H, m), 1.68-1.50 (6H, m), 1.46-1.32 (6H, m), 1.08-1.03 (6H, m), 0.99-0.94 (6H, m), 0.91-0.79 (9H, m).

NMR $^{13}$C (400 MHz, MeOD) ppm: 184.16, 179.37, 108.65, 101.50, 87.55, 87.52, 86.12, 85.48, 83.99, 79.81, 78.40, 71.89, 69.07, 65.35, 62.94, 58.98, 45.50, 40.42, 39.08, 39.02, 38.43, 37.42, 36.24, 36.04, 34.93, 34.65, 33.23, 32.56, 30.47, 28.67, 27.37, 17.94, 16.96, 16.06, 14.49, 13.29, 11.44, 8.44.

Exact mass: HR ESIMS: Calculated for $C_{38}H_{64}O_{13}Na^+$= 751.4239. found=751.4215.

Monensin oxodioxane 12 (50.3 mg, 0.07 mmol, 1 eq) was stirred in a mixture of THF-MeOH—H2O (2:2:1) at room temperature. NaOH 1N (250 µL) was added slowly. The mixture was stirred for 17 h. Then the mixture was evaporated to dryness to give a powder, which was suspended in dichloromethane (6 mL) and filtered off. The solid was washed several times with dichloromethane and the filtrate was evaporated to dryness to afford 39.0 mg (77%) of the desired acid.

Compound (28)—Monensin-7-ene Oxodioxane Flouric Acid

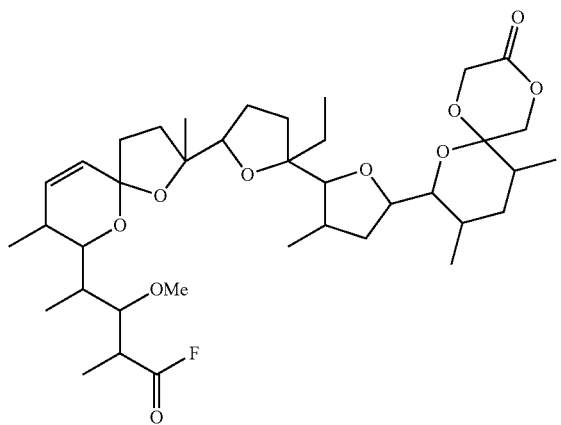

28

NMR $^1$H (300 MHz, CDCl$_3$) ppm: 5.95 (1H, dd, J1=9.48 Hz, J2=9.87 Hz), 5.55 (1H, d, J=9.66 Hz), 4.48 (1H, d, J=11.34 Hz), 4.38 (1H, d, J=17.13 Hz), 4.26 (1H, d, J=17.10 Hz), 4.21-4.15 (1H, m), 4.08 (1H, d, J=11.34 Hz), 3.88 (2H, m), 3.70-3.66 (2H, m), 3.39 (3H, s), 3.36-3.28 (1H, m), 2.84-2.79 (1H, m), 2.30-2.17 (2H, m), 2.14-1.80 (7H, m), 1.75-1.40 (9H, m), 1.39-1.19 (7H, m), 1.00-0.88 (18H, m).

NMR $^{13}$C (400 MHz, CDCl$_3$) ppm: 167.26, 165.93 (d, J=363.1 Hz), 134.91, 128.11, 104.58, 94.43, 86.81, 86.27, 85.57, 83.10, 81.29, 78.92, 77.65, 72.56, 71.14, 59.81, 59.04, 39.93 (d, J=44.48 Hz), 39.30, 37.43, 37.01, 35.40, 35.11, 35.06, 33.76, 33.11, 32.14, 32.03, 29.09, 28.29, 24.84, 17.68, 16.33, 16.07, 13.38, 12.11, 9.73, 8.21.

NMR $^{19}$F (400 MHz, CDCl$_3$) ppm: 36.89 ppm

Exact mass: HR ESIMS: Calculated for $C_{38}H_{59}O_{10}FNa^+$= 717.3984. found=717.3984.

In a dry three-neck round-bottomed flask, monensin oxodioxane 12 (300 mg, 0.42 mmol, 1 eq) was dissolved in anhydrous dichloromethane (30 mL) under argon. The mixture was cooled at −78° C. and DAST (110 µL, 0.84 mmol, 2 eq) was added very slowly. At the end of the addition, the reaction was stirring at room temperature during 1 day. The reaction mixture was washed several times with distilled water, dried over MgSO$_4$ and evaporated to dryness. The residue was chromatographed on silica gel (Cyclohexane/ AcOEt:80/20) to afford 91.1 mg (32%) of the desired product.

Compound (29)—Monensin-7-ene Oxodioxane Methanoate

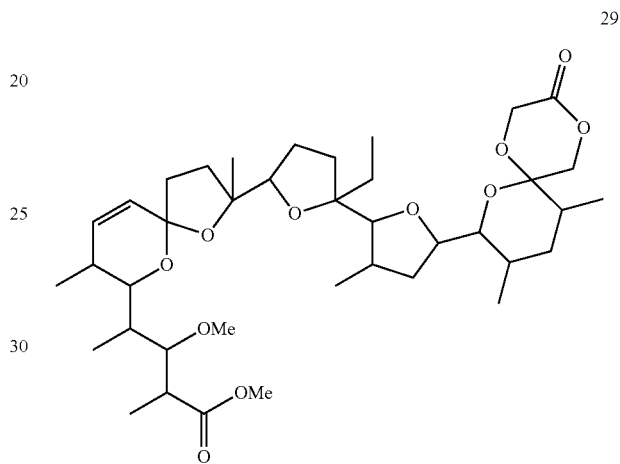

29

NMR $^1$H (400 MHz, CDCl$_3$) ppm: 5.95-5.90 (1H, dd, J1=9.56 Hz, J2=9.56 Hz), 5.51 (1H, d, J=9.56 Hz), 4.48 (1H, d, J=11.32 Hz), 4.36 (1H, d, J=17.12 Hz), 4.24 (1H, d, J=17.12 Hz), 4.20-4.18 (1H, m), 4.07 (1H, d, J=11.32 Hz), 3.87 (1H, d, J=4.52 Hz), 3.75 (1H, dd, J1=2.28 Hz, J2=8.04 Hz), 3.67 (4H, m), 3.59 (1H, m), 3.32 (4H, m), 2.63-2.60 (1H, m), 2.29-2.26 (1H, m), 2.19-2.16 (1H, m), 2.09-1.98 (5H, m), 1.93-1.75 (3H, m), 1.73-1.40 (8H, m), 1.35-1.27 (4H, m), 1.17 (3H, d, J=7.04 Hz), 1.01-0.86 (18H, m).

NMR $^{13}$C (400 MHz, CDCl$_3$) ppm: 176.40, 167.22, 135.10, 128.02, 104.50, 94.40, 86.52, 86.21, 85.59, 83.19, 82.29, 78.92, 77.62, 72.54, 71.46, 59.81, 58.70, 51.87, 40.66, 39.26, 37.41, 37.01, 35.42, 35.09, 35.03, 33.73, 33.18, 32.23, 31.32, 29.03, 28.20, 24.63, 17.67, 16.34, 16.07, 13.15, 12.17, 11.37, 8.18.

NMR $^{19}$F (400 MHz, CDCl$_3$) ppm: none.

Exact mass: HR ESIMS: Calculated for $C_{39}H_{62}O_{11}Na^+$= 729.4184. found=729.4160.

In a dry three-neck round-bottomed flask, monensin oxodioxane 12 (200 mg, 0.28 mmol, 1 eq) was dissolved in anhydrous dichloromethane (20 mL) under argon. The mixture was cooled at −78° C. and DAST (69 µL, 0.56 mmol, 2 eq) was added very slowly. At the end of the addition, the reaction was stirring at room temperature during 1 day. The reaction mixture was washed several times with distilled water, dried over MgSO$_4$ and evaporated to dryness. The residue was chromatographed on silica gel (Cyclohexane/ AcOEt:80/20) to afford 128.0 mg (66%) of the desired product.

Compound (31)—7-oxo, 21-hydroxy, 25-acid Monensin

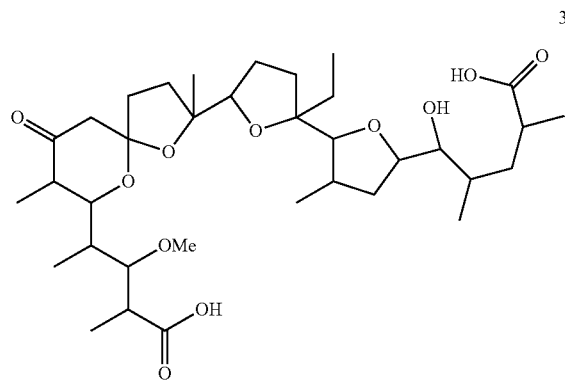

NMR $^1$H (400 MHz, MeOD) ppm: 4.36 (1H, d, J=13.32 Hz), 4.25-4.20 (1H, m), 4.15-4.05 (1H, m), 3.95-3.90 (1H, m), 3.74-3.56 (1H, m), 3.51-3.39 (4H, m), 2.50-2.38 (3H, m), 2.37-2.27 (2H, m), 2.25-2.06 (3H, m), 2.01 (4H, m), 1.88 (5H, m), 1.77-1.72 (1H, m), 1.70-1.38 (4H, m), 1.30-1.20 (5H, m), 1.19-1.04 (3H, m), 1.03-0.90 (16H, m).

NMR $^{13}$C (400 MHz, MeOD) ppm: 198.59, 180.40, 170.38, 103.35, 88.72, 88.10, 86.91, 84.73, 84.54, 84.39, 79.64, 78.56, 60.73, 44.87, 42.28, 42.24, 39.46, 38.87, 36.36, 36.29, 36.20, 35.76, 34.08, 33.36, 30.78, 28.16, 27.76, 24.23, 23.70, 20.29, 17.00, 16.93, 10.77, 9.67, 8.28.

Exact mass: HR ESIMS: Calculated for $C_{35}H_{58}O_{11}Na^+$= 677.3871. found=677,3854.

Monensin oxolactone 19 (48.9 mg, 0.08 mmol, 1 eq) was stirred in a mixture of THF-MeOH—H$_2$O (2:2:1) at room temperature. NaOH 1N (250 μL) was added slowly. The mixture was stirred for 5 h. Then the mixture was evaporated to dryness to give a powder, which was suspended in dichloromethane (6 mL) and filtered off. The solid was washed several times with dichloromethane and the filtrate was evaporated to dryness to afford 50.0 mg (96%) of the desired acid.

Example 3

Evaluation of Compound Toxicity and Efficacy Against E. Tennela

*Eimeria* sp is a unicellular sporozoan (protozoan) of the phylum Apicomplexa which has a monoxenous intracellular life cycle in which the presence of the host is necessary for its development and which consists of two phases: an asexual phase (schizogony) and a sexual phase (gamogony). Infection of the host by the *Eimeria* parasite can cause a serious disease of the intestine known as coccidiosis, which has a very wide set of hosts (poultry, rabbits, ruminants, feline species, etc.).

In the poultry case, coccidiosis is responsible for enormous damage, the cost of which can be estimated at millions euros a year. This disease is regarded as a scourge that the poultry industry has to cope with throughout the rearing period, regardless the category of the age of the bird and the season. The coccidial parasites affecting chickens belong to the genus *Eimeria* of the family Eimeriidae; there are currently nine species and the pathogenicity varies according to species (*Eimeria tenella, E. necatrix, E. acervulina*, and *E. maxima* are highly pathogenic. *E. praecox, E. mitis, E. brunetti, E. hagani*, and *E. mivati* are less pathogenic). During the infection by *Eimeria*, the localization of the parasite in the intestine of the host is species dependent. Because of its frequency, its pathogenicity and its virulence, which cause enormous losses on poultry farms, *Eimeria tenella* is the most studied species globally. Importantly, studies have shown that rather than using exclusively in vivo models to study the parasite, it is also possible to cultivate *Eimeria* in vitro. However, it is crucial to precisely control the culture conditions, including using specific permissive cells for amplification of the parasite.

By using in-vitro culture, it was possible to control the environment and to observe how environmental changes and manipulation (medium, temperature, pH, etc.) affected the development of the parasite. In contrast, working in vivo would have added uncontrollable variables in the form of complex growth medium/environmental conditions (e.g. intestinal microbial flora, hormones, and the like). Host sensitivity can also play a role.

MDBK Model for Screening 10 Compounds in Vitro

For culturing and screening in vitro, the choice of cell line is one of the key factors for proper infection and treatment. In addition to an appropriate choice of cell line, the culture conditions are also crucial in order to be able to visualize the various stages of the life cycle of *Eimeria tenella*. Visualizing the various phases (gamogony and schizogony) of the development of *Eimeria* in vitro makes it possible to test compounds and to determine exactly how they are able to act and at what stage of the parasite's development.

In-vivo screening tests have shown their limits, owing to the toxicity of certain compounds in addition to other host-related factors. Work undertaken in this field using the in-vivo model for the screening of anticoccidials has shown that the efficacy cannot be increased by increasing the concentration, because of the toxicity that can be caused by very high concentrations, such as the case of the Monensin. This shows the need to find an alternative whereby the doses (of anticoccidials/coccidiostats) can be increased without the fear of fatal effects that are a problem in vivo, and to survey the parasite's development daily using microscopic observations. This allows facile evaluation of resistance using the in vitro test.

MDBK, and Method of Screening (Treatment)

For screening tests, the in vitro model offers a wide range of possibilities that may help in determining the stage at which the compound is most effective.

Treatment of cells before infection
Treatment of parasite before infection
Treatment of cells after infection
Treatment and infection of cells at the same time
Treatment of cells 24 h after infection
Treatment of cells after first schizogony It should also be pointed out that for screening tests it is not important to complete the cycle because the most critical stages for the host during infection with *Eimeria* are sporozoite release and the first schizogony; these are the stages at which the sporozoites and merozoites destroy the host's intestinal wall, causing bloody diarrhea, and at which point food absorption becomes impaired, leading to weight loss and ultimately the death of the host if the infection is highly virulent (and not controlled).

In order to stimulate the host immune system in developing protection against any reinfection by the same species, the new anticoccidial molecules may permit the infection of the sporozoite into the cell host, but prevent illness by impairing/inhibiting the progression of the parasite to the schizogeny stage.

Cytotoxicity testing. For the prevention and the treatment, a compound is considered effective when it is non toxic or its toxicity is low for host cells but high for the target (parasite).

For cytotoxicity testing and determination of the $IC_{50}$, the in vitro model is one of the best methods, enabling this type of testing to be carried out directly on cells alone without fear of fatal consequences as in vivo. The $IC_{50}$ is the maximum concentration at which at least 50% of cells survive following a treatment. All concentrations above it are excluded for the test; values below it, on the other hand, can be tested in order to determine the concentration that will totally or partially eliminate the parasite or inhibit its development. This test consists in testing several concentrations on cell culture in 96-well plate; the concentrations are tested in duplicate, and the cytotoxicity of the molecules is evaluated with special kits based on an oxidation-reduction reaction at the cell-machinery level (mitochondria).

As in the MTT kit (Promega), the reagent used is the tetrazolium salt MTT (3-[4,5-dimethylthiazol-2-yl]-2,5-diphenyltetrazolium bromide). The tetrazolium ring that it contains is reduced to formazan by the mitochondrial succinate dehydrogenase of active living cells. The color of the medium thus changes from yellow to purplish-blue. The intensity of this color is proportional to the number of living cells present at the time of testing but also to their metabolic activity. The percentage of living cells is determined from the ratio between the absorbance for the test well and the absorbance for the control well (cells alone).

Monensin, a compound which has been used for a number of years to combat coccidiosis, was used as a positive control.

The in vitro test made it possible to evaluate the efficacy of new synthesised polyether ionophores against coccidia. This test enabled an initial selection of active molecules in anticipation of in vivo tests in poultry.

Initially, the inhibitory concentration $IC_{50}$ was determined. It corresponded to the concentration of polyether ionophore allowing the viability of 50% of cells. Bovine cells were cultured and incubated for 24 hrs at 40° C. in the wells of a 96-well plate. Then, a fixed concentration (50 g/µL-0.4 g/µL) of polyether ionophore was added to each well. The cells were incubated at 40° C. for 24 hrs. 20 µL, of "Cell Titer" was added to each well. The cells were again incubated for 30 min to 1 hour at 40° C. before the plate was read in a plate reader at a wavelength of 490 nm (maximum absorption of the formazan). This reading determined the optical density (OD) of each well and allowed access to the percentage of inhibition.

$$I50 = (OD_{treated}/OD_{control}) \times 100$$

$$\% \text{ viability} = [1-(OD_{treated}/OD_{control})] \times 100.$$

Figure 26:
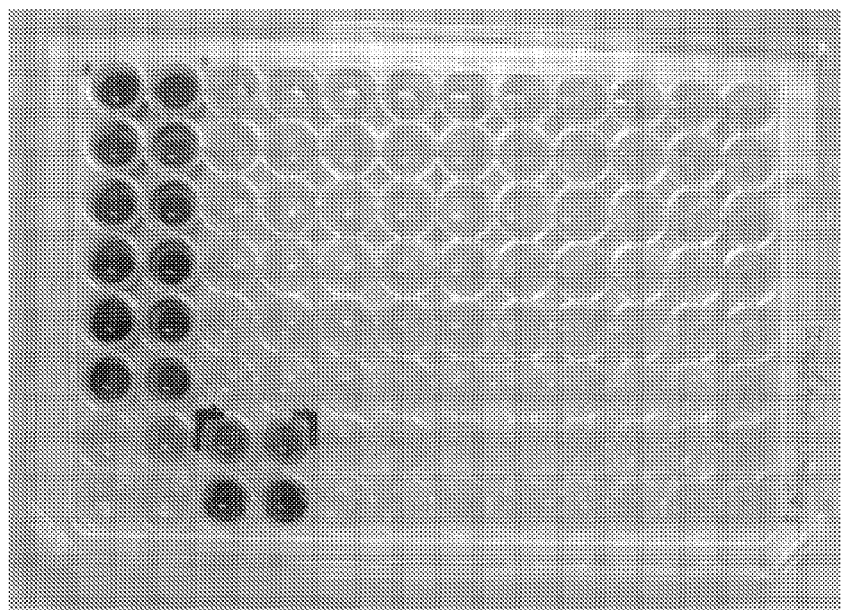
FIG. 26 provides results for 96-well ionophore toxicity assay and schematizes the reaction whereby MTS Tetrazolium is converted to Formazan, resulting in the observed color change.
Figure 26:
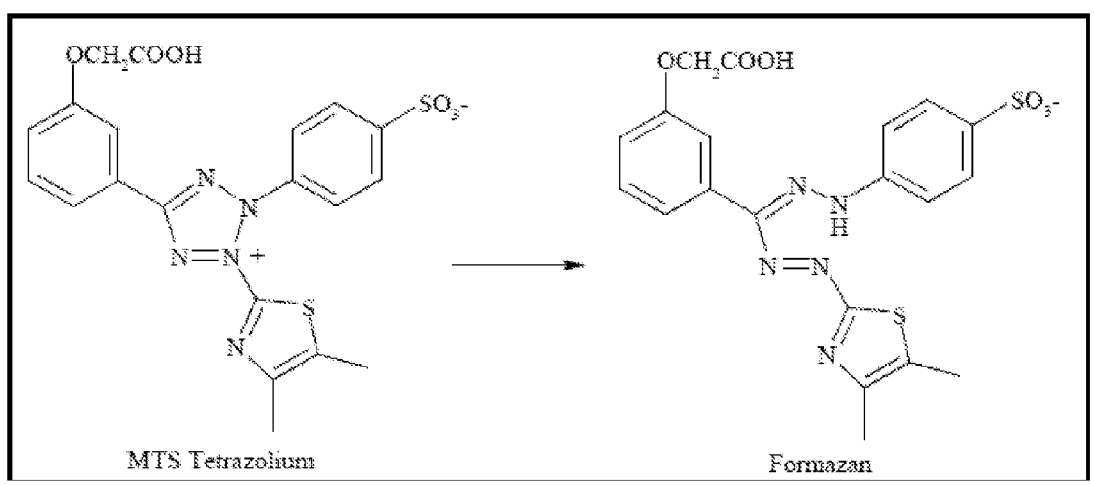
Figure 27:
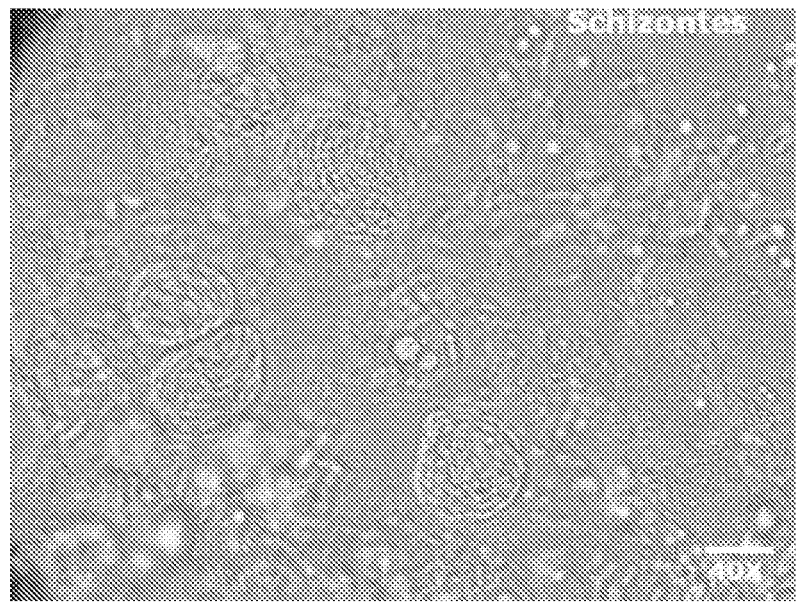
FIG. 27 provides pictures of developing schizonts and mature schizonts (release of merozoites)
Figure 27:
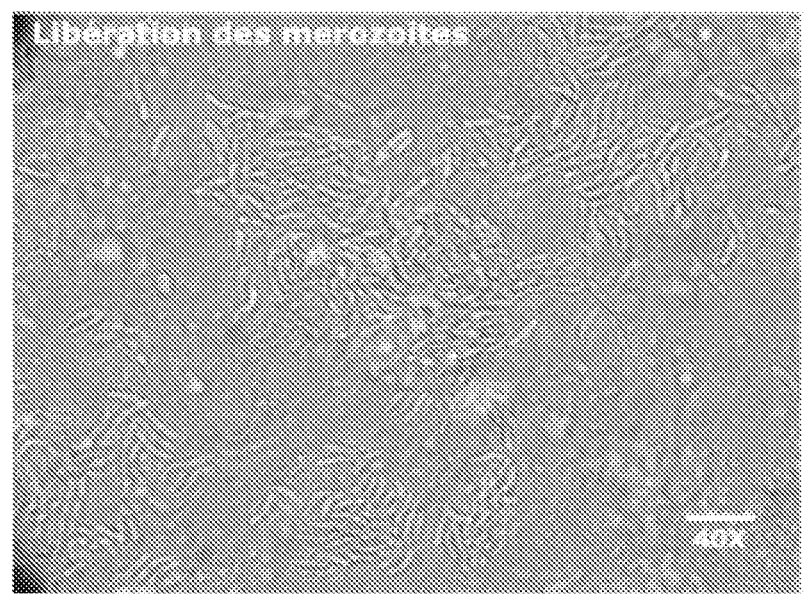

FIG. 26 represents a 96-well plate after adding "Cell Titer". The intensity of colours depends on the toxicity of the polyether ionophore tested. Increasing color intensity corresponded to increasing number of living cells. The principle of "Cell Titer" is based on oxidation-reduction reactions that occur at the level of mitochondria in living cells, the tetrazolium contained in the "Cell Titer" is reduced to formazan (FIG. 26).

Once the $IC_{50}$ concentration was determined, the test was performed on infected cells. The working concentration chosen was always lower than $IC_{50}$.

Figure 30:
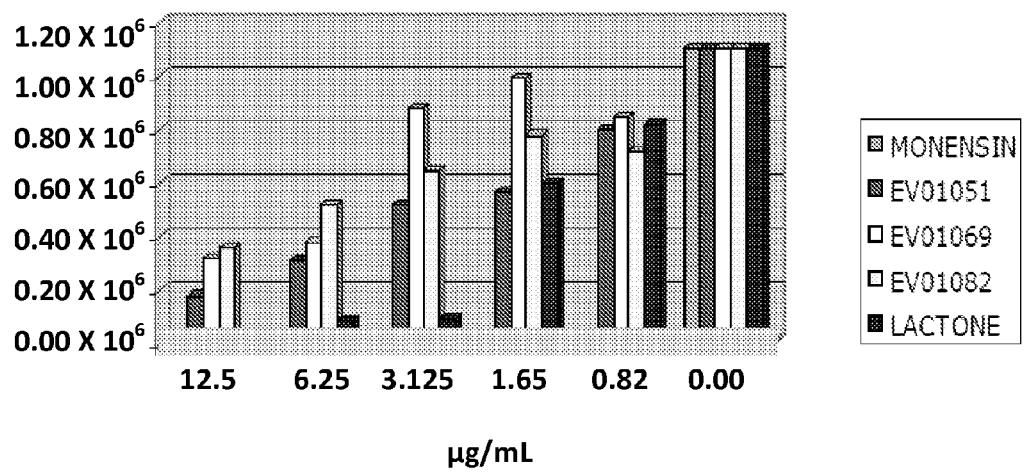
FIG. 30 provides a graph of number of merozoites plotted against concentrations of the indicated inventive compounds.
Figure 30A:
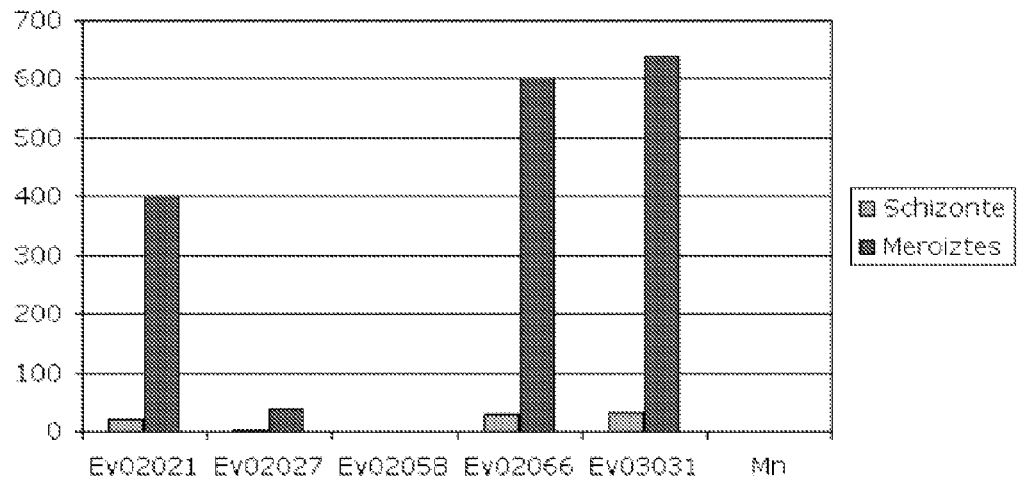
FIG. 30A provides a graph of number schizonts/merozoites versus indicated compounds (monensin as control) at 3.125 µg/mL.
Figure 30B:
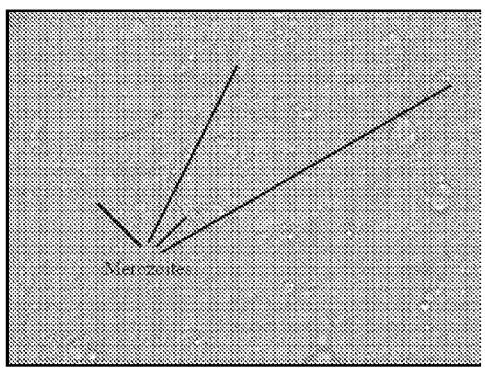
FIG. 30B provides picture showing merozoites present for EV 021121.

After having cultured cells at 40° C. in each well of a 96-well plate, they were treated with a specific concentration (<$IC_{50}$, allowing the inhibition of parasites in over 50% of cells) of polyether ionophore. Then, the sporozoites of *Eimeria tenella* were excysted and the cells infected with purified sporozoites. After incubation for 24 hrs at 40° C., the medium was changed. The efficiency of molecules was evaluated microscopically after 40 hrs and 48 hrs. The release of merozoites was noted (FIG. 30B). Thus, in explicit cases, the merozoites released were counted; in ambiguous cases, the quantitative PCR (Poly Chain Reaction) will be used. For each test, a positive control of treatment (with monensin 1a) and a positive control of infection was made.

Figure 29:
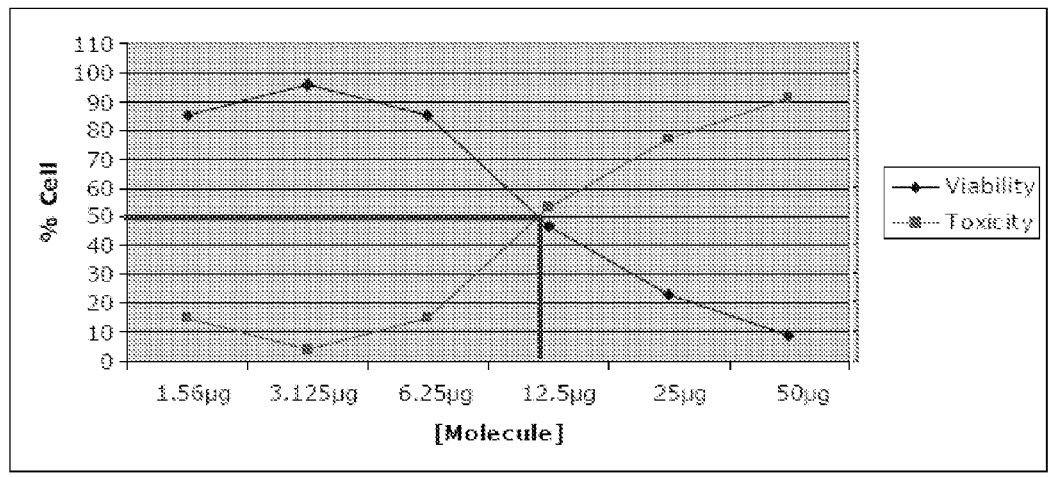
FIG. 29 presents IC$_{50}$ determination for EV 01051.

Fifteen synthesised molecules were tested in vitro. Firstly, the toxicity towards the cells of the first ten was evaluated. The results are summarised in FIGS. 28-30. Toxicity was determined by as described above. The graph (FIG. 29) shows the graphical determination of the $IC_{50}$ of EV 01051. Secondly, the molecules of the first round of analysis, 1a, 3a, 3b, 6a and 7 were tested at five different concentrations in the presence of the parasite. The results obtained are shown in FIG. 30. According to the graph, the polyether ionophores 3a (EV 01051), 3b (EV 01069) and 6a (EV 01082) did not appear to significantly inhibit the development of the parasite *Eimeria tenella* in cell culture. In contrast, at high concentrations, greater than or equal to 12.5 g/µL, the lactone 7 (EV 01060) inhibited the formation of merozoites. The monensin acid 1a inhibited the formation of merozoites at very low concentrations.

Figure 30C:
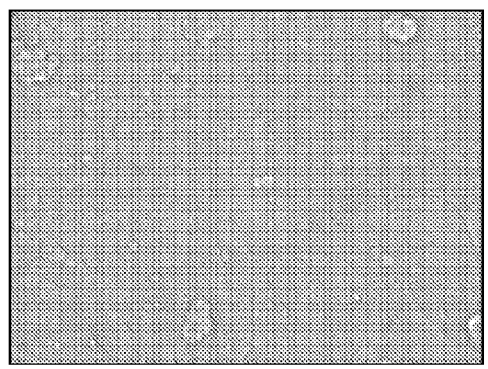
FIG. 30C provides picture showing merozoites not present for EV 02058.

The molecules of the second series, 3c, 4c, 8a, 14a and 19 showed no toxicity for the MDBK cells at a high concentration (>50 g/µL). They were tested only at one concentration of 3.125 g/µL, reference concentration (FIG. 30A). The number of schizonts and merozoites was evaluated in each case. At this concentration, the molecules 3c (EV 03031), 4c (EV 02066) and 14a (EV 02121) showed no significant activity in inhibiting the development of the parasite *Eimeria tenella* in vitro, as indicated by the observation schizonts and merozoites. Promisingly, molecule 8a (EV 02058) showed a very high efficacy against the parasite. It was able to block the development of the parasite *Eimeria tenella* in vitro. Indeed, an absence of schizonts and merozoites was observed (FIG. 30C).

Figure 31A:
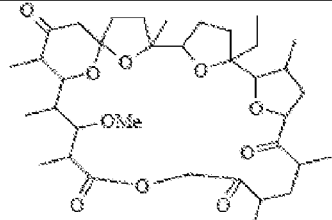
FIG. 31A depicts compounds (18, 12, 27, 31, 26)
Figure 31A:
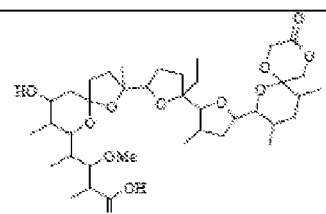
Figure 31A:
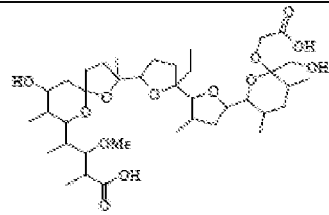
Figure 31A:
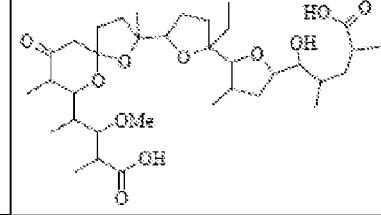
Figure 31A:
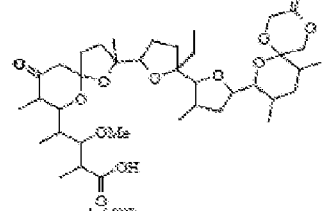
Figure 31B:
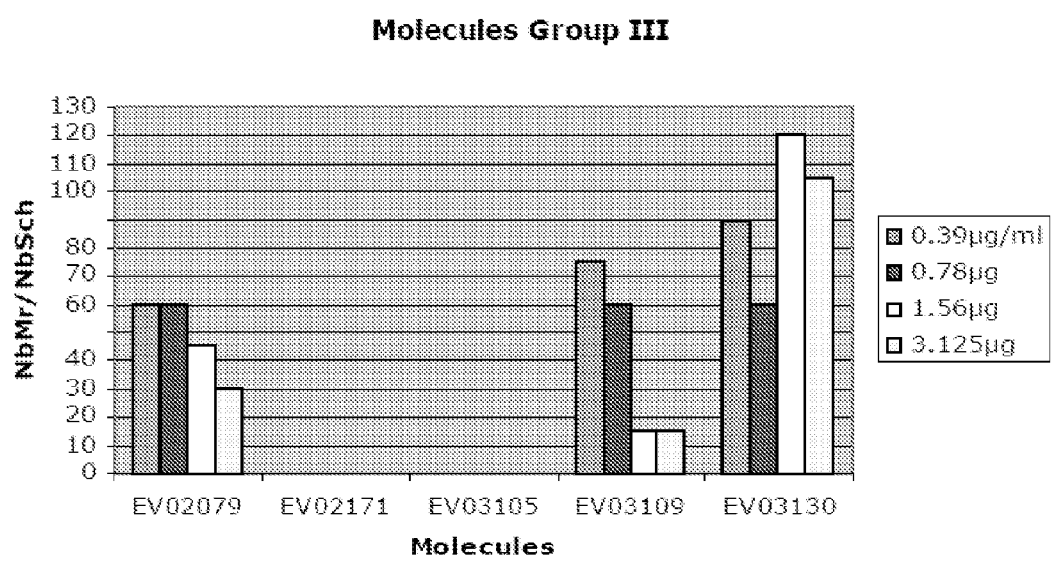
FIG. 31B provides a graph showing efficacy of the compounds of FIG. 30A against *E. tenella*, at the indicated concentrations.

Though the compound did not completely inhibit the development of the parasite, molecule 19 (EV 02127) showed significant efficacy against the parasite (FIG. 30A). This can be important, for example, in the context of promoting a natural immunity during a secondary infection. The molecules of the third series, 12, 18, 26, 27 and 31 (FIG. 31A) were tested on *Eimeria tenella* in different concentrations ranging from 3.125 to 0.78 g/µL. The number of merozoites and the number of schizonts were determined for each molecule at four concentrations (FIG. 31B).

At very low concentrations (<0.39 µg/µL), the molecules 12 and 27 showed significant efficacy against *Eimeria tenella*. Indeed, these two molecules completely inhibited its development in vitro (FIG. 31B). The results obtained for the molecules 18, 31 and 26 show that they did not inhibit the parasite at low concentrations. However, at concentrations greater than 1.56 g/µL, the saponified oxidised monensin 31 was significantly effective against the parasite.

Fifteen new polyether ionophores were submitted for additional in vitro testing. Among these compounds, three (8a, 12 and 27) showed a significant activity towards the parasite *Eimeria tenella*. The molecule 8a had already been synthesised by Sakakibara, whereas compounds 12 and 27 were completely new. Another polyether that showed satisfactory and encouraging results was oxo-lactone monensin 19. Together, these four molecules offer very low cytotoxicities with significant efficacy against *E. tenella*. Other compounds according to the instant invention are being evaluated for toxicity (human and animal cells) and efficacy against *Eimeria* spp. and *Plasmodia* spp.

Prophetic Example

Male broilers aged 7 days are divided into 9 groups each having 10 birds and allowed to take feeds differing in the content of the inventive compounds, monensin, or control (0, 0.1. 0.2 or 0.4% by weight) ad libitum. On the age of 10 days, $1\times10^4$ or $1\times10^5$ oocysts of *E. tenella* are administered to the birds. On the age of 17 days, the cecal length, the lesion index, and the cecal oocyst count are examined. On average, birds given the inventive compounds exhibit significantly improved clinical signs over birds given control or monensin.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A compound according to formula (II):

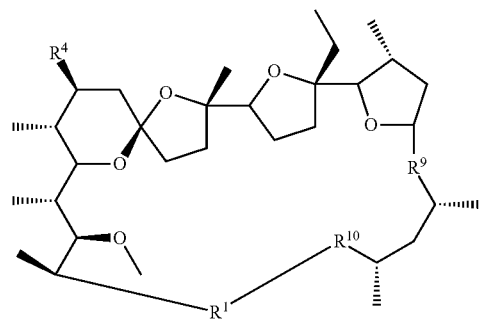

(II)

wherein
$R^1$ is C(=O)O, C(=O)OR$^2$, alkyl, aralkyl, or heterocyclyl;
$R^2$ is CH$_2$
$R^4$ is hydroxyl, halogen, (=O), OR$^5$, O(C=O)R$^5$, F, alkyl, aryl, aralkyl, heteroaryl, or heterocyclyl;
$R^5$ is H, alkyl, or alkyl aryl; and wherein either
$R^9$ is C(=O)O or CHF and $R^{10}$ is CH$_2$ or C(=O);
or $R^9$ and $R^{10}$ are CH and are connected to each other by O.

2. A method for treating or preventing a protozoal infestation comprising the step of administering to an animal in need thereof the compound of claim 1, thereby treating the animal.

3. The method of claim 2 wherein the animal is an avian and the compound is administered to treat or prevent coccidiosis.

4. The method of claim 2 wherein the compound is administered orally via drinking water or as an additive to feedstuffs.

5. The method of claim 2 wherein the compound is administered in the amount of about 0.1 to 10 mg/kg animal body weight.

6. The method of claim 2 further comprising administering an effective amount of a vaccine which is effective in protecting avians against protozoal infestations.

7. The method of claim 2 which is effective in reducing or eliminating babesiosis in bovines.

8. The method of claim 2 which is effective in reducing, preventing, or eliminating protozoal infestations in humans or non-human animals.

9. The method of claim 2 which is effective in reducing, preventing, or eliminating malaria in humans.

10. A method of treating coccidiosis in a bovine animal by administering, when clinical signs of coccidiosis infection exist, to an animal an effective amount of the compound of claim 2.

11. The method according to claim 10 wherein the compound is administered in an amount that increases weight gain in the bovine animal.

12. The method according to claim 10 wherein the coccidiosis results from infection from *Eimeria bovis, E. aubemensis*, or *Eimeria zuemii*.

13. The method according to claim 10 wherein said administration reduces *Eimeria oocyte* shedding and diarrhea.

\* \* \* \* \*